US012740742B2

(12) United States Patent
Swertfager et al.

(10) Patent No.: US 12,740,742 B2
(45) Date of Patent: Sep. 22, 2026

(54) THERAPEUTIC METHODS FOR SLEEP RESPIRATORY ISSUES VIA A POSITIONAL THERAPY DEVICE THAT MONITORS A USERS'S HEAD POSITION

(71) Applicant: SleepDev, Inc., Aptos, CA (US)

(72) Inventors: Michael McNeil Swertfager, Aptos, CA (US); James Barry Gartrell, San Monica, CA (US)

(73) Assignee: SleepDev, Inc., Aptos, CA (US)

( * ) Notice: Subject to any disclaimer, the term of this patent is extended or adjusted under 35 U.S.C. 154(b) by 194 days.

(21) Appl. No.: 18/777,408

(22) Filed: Jul. 18, 2024

(65) Prior Publication Data

US 2025/0204849 A1 Jun. 26, 2025

Related U.S. Application Data

(60) Provisional application No. 63/614,263, filed on Dec. 22, 2023.

(51) Int. Cl.
*A61B 5/00* (2006.01)
*A61B 5/024* (2006.01)
(Continued)

(52) U.S. Cl.
CPC ........ *A61B 5/4818* (2013.01); *A61B 5/02405* (2013.01); *A61B 5/0816* (2013.01);
(Continued)

(58) Field of Classification Search
None
See application file for complete search history.

(56) References Cited

U.S. PATENT DOCUMENTS

| | | | |
|---|---|---|---|
| 4,220,142 | A | 9/1980 | Rosen |
| 4,715,367 | A | 12/1987 | Crossley |

(Continued)

FOREIGN PATENT DOCUMENTS

| | | |
|---|---|---|
| AU | 768822 | 4/2001 |
| CN | 101053538 | 10/2007 |

(Continued)

OTHER PUBLICATIONS

Summer, Jay, "At-Home Sleep Tests and Studies", May 8, 2023, https://www.sleepfoundation.org/sleep-studies/at-home-sleep-study, downloaded May 18, 2023, 10 pages.

(Continued)

*Primary Examiner* — Thomas S McCormack
(74) *Attorney, Agent, or Firm* — Jaffery Watson Hamilton & DeSanctis LLP

(57) ABSTRACT

Systems, devices, and methods for facilitating diagnosis of sleep respiratory issues and/or delivering therapy for such issues are provided. According to one embodiment, a positional therapy device may be integrated with a PAP mask system to provide an effective and more sleep conducive method for positional sleep therapy for PAP system users. In some examples, positional therapy may be implemented through notifications delivered by a speaker associated with the positional therapy device to reduce symptoms of positional sleep respiratory issues. A positional sensor within the positional therapy device facilitates recognition regarding when a user (sleeper) is out of their programmed sleep position. The sleeper can then be notified via the speaker to adjust themselves to a more optimal sleep position for reduced snoring and/or sleep obstruction. The positional therapy device may alternatively or additionally capture user sleep data to facilitate diagnosis of a sleep respiratory issue by a medical professional.

37 Claims, 28 Drawing Sheets

(51) Int. Cl.

| | |
|---|---|
| ***A61B 5/08*** | (2006.01) |
| ***A61B 5/11*** | (2006.01) |
| ***A61B 5/145*** | (2006.01) |
| ***A61B 5/369*** | (2021.01) |
| ***A61B 5/398*** | (2021.01) |
| ***A61M 16/06*** | (2006.01) |
| ***G16H 15/00*** | (2018.01) |

(52) U.S. Cl.

CPC ........ *A61B 5/1116* (2013.01); *A61B 5/14542* (2013.01); *A61B 5/369* (2021.01); *A61B 5/398* (2021.01); *A61B 5/7405* (2013.01); *A61B 5/746* (2013.01); *A61M 16/06* (2013.01); *G16H 15/00* (2018.01)

(56) References Cited

U.S. PATENT DOCUMENTS

| | | | |
|---|---|---|---|
| 4,788,533 | A | 11/1988 | Mequignon |
| 4,802,485 | A | 2/1989 | Bowers |
| 4,830,008 | A | 5/1989 | Meer |
| 4,848,360 | A | 7/1989 | Palsgard |
| 5,081,447 | A | 1/1992 | Echols |
| 5,265,624 | A | 11/1993 | Bowman |
| 5,381,801 | A | 1/1995 | McShane |
| 5,447,161 | A | 9/1995 | Blazek |
| 5,555,891 | A | 9/1996 | Eisenfeld |
| 6,057,767 | A | 5/2000 | Barnoach |
| 6,306,088 | B1 | 10/2001 | Krausman et al. |
| 6,544,199 | B1 | 4/2003 | Morris |
| 6,600,949 | B1 | 7/2003 | Turcott |
| 6,641,571 | B2 | 11/2003 | Redmond |
| 6,935,335 | B1 | 8/2005 | Lehrman |
| 6,970,792 | B1 | 11/2005 | Diab |
| 7,081,095 | B2 | 7/2006 | Lynn |
| 7,117,028 | B2 | 10/2006 | Bardy |
| 7,118,534 | B2 | 10/2006 | Ward |
| 7,311,666 | B2 | 12/2007 | Stupp |
| 7,331,349 | B2 | 2/2008 | Brady |
| 7,575,005 | B2 | 8/2009 | Mumford |
| 7,599,892 | B1 | 10/2009 | Berger |
| 7,691,067 | B2 | 4/2010 | Westbrook |
| 7,717,848 | B2 | 5/2010 | Heruth |
| 7,956,756 | B2 | 6/2011 | Kubey |
| 8,213,670 | B2 | 7/2012 | Lai |
| 8,493,220 | B2 | 7/2013 | Virtanen |
| 8,784,293 | B2 | 7/2014 | Popovic |
| 8,803,682 | B2 | 8/2014 | Wong |
| 9,734,815 | B2 | 8/2017 | DeFranks, II |
| 9,906,636 | B2 | 2/2018 | Lee |
| 10,470,719 | B2 | 11/2019 | Shimol |
| 10,638,973 | B2 | 5/2020 | Levendowski |
| 10,653,366 | B2 | 5/2020 | Levine |
| 10,964,195 | B1 | 3/2021 | Huang et al. |
| 11,503,396 | B2 | 11/2022 | Sandanger |
| 12,551,164 | B2 | 2/2026 | Swertfager et al. |
| 2002/0184050 | A1 | 12/2002 | Papageorge |
| 2002/0188205 | A1 | 12/2002 | Mills |
| 2003/0002705 | A1 | 1/2003 | Boessen |
| 2003/0199945 | A1 | 10/2003 | Ciulla |
| 2004/0015337 | A1 | 1/2004 | Richard |
| 2005/0197588 | A1 | 9/2005 | Freeberg |
| 2005/0234313 | A1 | 10/2005 | Rowlandson |
| 2006/0074334 | A1 | 4/2006 | Coyle |
| 2006/0100538 | A1 | 5/2006 | Genger |
| 2007/0084470 | A1 | 4/2007 | Sarazen |
| 2007/0208269 | A1 | 9/2007 | Mumford |
| 2007/0214013 | A1 | 9/2007 | Silverman |
| 2007/0239225 | A1 | 10/2007 | Saringer |
| 2007/0282177 | A1 | 12/2007 | Pilz |
| 2008/0023011 | A1 | 1/2008 | Zohlmann |
| 2008/0127978 | A1 | 6/2008 | Rubin |
| 2008/0146890 | A1 | 6/2008 | Leboeuf |
| 2008/0234598 | A1 | 9/2008 | Snyder |
| 2008/0264426 | A1 | 10/2008 | Walker |
| 2009/0120446 | A1 | 5/2009 | Vaska |
| 2009/0198145 | A1 | 8/2009 | Chow |
| 2009/0250070 | A1 | 10/2009 | Pfeifer |
| 2011/0295083 | A1* | 12/2011 | Doelling .................. A61B 5/11 600/407 |
| 2012/0097156 | A1 | 4/2012 | Bowman et al. |
| 2012/0229634 | A1 | 9/2012 | Laett |
| 2015/0150498 | A1 | 6/2015 | George |
| 2016/0367203 | A1 | 12/2016 | Lyons |
| 2019/0224050 | A1 | 7/2019 | Kurzweil |
| 2019/0388024 | A1* | 12/2019 | Goldstein ............ A61B 5/7405 |
| 2020/0051415 | A1 | 2/2020 | Grubbs et al. |
| 2020/0297955 | A1 | 9/2020 | Shouldice |
| 2020/0383633 | A1* | 12/2020 | Su .......................... A61B 5/742 |
| 2021/0007669 | A1 | 1/2021 | Jin |
| 2021/0169417 | A1 | 6/2021 | Burton |
| 2022/0203063 | A1 | 6/2022 | Kahlert et al. |
| 2023/0284973 | A1 | 9/2023 | Swertfager et al. |
| 2025/0204849 | A1 | 6/2025 | Swertfager |

FOREIGN PATENT DOCUMENTS

| | | | |
|---|---|---|---|
| EP | 1578251 | | 7/2004 |
| JP | 0349748 | A | 3/1991 |
| JP | 07213546 | A | 8/1995 |
| JP | 2005185650 | A | 7/2005 |
| JP | 2005270627 | | 10/2005 |
| JP | 2005312901 | | 11/2005 |
| JP | 2005318907 | | 11/2005 |
| JP | 2007294143 | A | 11/2007 |
| JP | 2008011865 | | 1/2008 |
| JP | 2007199025 | A | 12/2012 |
| JP | 6697035 | B2 | 5/2020 |
| JP | 6993320 | B2 | 2/2022 |
| KR | 20210042227 | A | 4/2021 |
| WO | 2002065901 | | 8/2002 |
| WO | 2006133548 | | 12/2006 |
| WO | 2007072390 | | 6/2007 |
| WO | 2007100959 | | 9/2007 |
| WO | 2008008915 | | 1/2008 |
| WO | 2011139141 | | 11/2011 |
| WO | 2016153359 | A2 | 9/2016 |
| WO | 2023230012 | | 11/2023 |
| WO | 2023230012 | A1 | 11/2023 |
| WO | 2025019710 | A1 | 1/2025 |

OTHER PUBLICATIONS

Goyal, Munish, et al., "Obstructive Sleep Apnea Diagnosis and Management", Science of Medicine, Mar./Apr. 2017, pp. 120-124.

"What to Know About an At-Home Sleep Test", https://www.hopkinsmedicine.org/health/wellness-and-prevention/what-to-know-about-an-at-home-test, downloaded May 18, 2023, 4 pages.

PCT Search Report and Written Opinion for PCT/US23/23133, mailing date of Oct. 10, 2023, 11 pages.

PCT International Search Report and Written Opinion for International Application No. PCT/US2024/038608, mailing date Dec. 10, 2024, 30 pages, USPTO.

Extended European Search Report for EP Application No. 23812426.7-1113, mailing date Apr. 13, 2026, 9 pages. EPO.

* cited by examiner

900

910 920 930

| Name | Related Config | Description |
|---|---|---|
| LED brightness | standbyLedLevel | The user can set the brightness of the LED on the device. |
| Alert Hold Off | alertHoldoffCount | After rolling into the alert zone, how many seconds does the user want to wait until the alert set start |
| Squelch | alertSquelchLevel | After how many alerts in an alert set does the user want to hear before it stops and waits for the next time the user is alerted? Can range from 1 to infinity. |
| Alert Ramp | alertMode<br>alertStartValue<br>alertScaleFactor<br>alertGrowthFactor | Each alert in an alert set can ramp in volume. Does the user want the volume to increase between alerts exponentially or arithmetically? Or, stay constant? |
| Start Volume | alertStartValue | What is the volume of the 1st alert in an alert set? |
| End Volume | alertMode<br>alertStartValue | What is the volume of the last alert in an alert set? |
| Alert Angle | alertAngle | From the set alert point, how many degrees from that point does the user want to set the alert zone. |
| Snooze | alertSnoozeTime | When the user taps the device, how long does they want the device to not notify them if they roll into the alert zone. |
| Alert Delays | alertDelayTime | In an alert sec, how many seconds does the user want between alert sounds. |
| Tone Duration | alertDurationTime | A user can use a sampled sound or a tone. If the user is using a tone for alerts, they can set how long each tone alert lasts. |
| Tone or Sample | alertPattern | A user can use a sampled sound or a tone. This allows them to choose which. |

| | Data Type | Name | Description |
|---|---|---|---|
| 1501 | time_t | timestamp | 32-bit seconds since the epoch 1970-01-01 |
| 1502 | uint32_t | stateTime | milliseconds that we have been in the current state |
| 1503 | uint8_t | state | current state from state machine |
| | uint8_t | hwFlags | (Accel Int 1, Accel Int 2, MIC Int, Chg-En Int, D4, D19 ) |
| | uint8_t | swFlags | (Valid Accel, Accel SoftInt 1, Accel Soft Int2, MIC SoftInt, Snoring Int, Flat Int, REM Int ) |
| 1504 | uint8_t | alertLevel | Current Alert Level |
| 1505 | uint16_t | alertCount | Total Alerts for this sleep session |
| 1506 | uint16_t | motionCount | Total Accel motion interrupts for this sleep session |
| 1507 | uint16_t | micCount | Total Mic auditory interrupts for this sleep session |
| | uint16_t | vDDH | converted to mV |
| | uint16_t | vBat | converted to mV |
| | uint16_t | vSys | converted to mV |
| | uint16_t | vIn | converted to mV |
| | uint16_t | iChg | permyriad of programmed max charge (2.5mA), 50.25% = 5025 |
| | int16_t | tempCore | converted to signed 16-bit degC * 100 |
| | int16_t | tempAlt | converted to signed 16-bit degC * 100 |
| 1511 | int16_t | X | captured as 14-bit 2's complement, current absolute pointing angle |
| 1512 | int16_t | Y | captured as 14-bit 2's complement, current absolute pointing angle |
| 1513 | int16_t | Z | captured as 14-bit 2's complement, current absolute pointing angle |
| 1514 | int16_t | tareX | captured as 14-bit 2's complement, set during calibration, specifies alert angle |
| 1515 | int16_t | tareY | captured as 14-bit 2's complement, set during calibration, specifies alert angle |
| 1516 | int16_t | tareZ | captured as 14-bit 2's complement, set during calibration, specifies alert angle |
| 1521 | uint8_t | heartRate | Beats per minute extrapolated from IMU or microphone |
| 1522 | uint8_t | breathRate | Breaths per minute extrapolated from IMU or microphone |
| | uint8_t | chargeStat | Current charge status (bit6 = Constant Voltage, bit5 = Charge Done, bit1 = Power Good) |
| 1523 | uint8_t | oxygenSat | Current oxygen saturation reading, stored as percent 0-100 |
| 1524 | float | zAngle | computed from (current X,Y,Z + calibrated Tare) |
| 1525 | float | zPitch | computed from (current X,Y,Z + calibrated Tare) |
| 1526 | float | zRoll | computed from (current X,Y,Z + calibrated Tare) |

| Ref. | Data Type | Name | Default Value | Details |
|---|---|---|---|---|
| | uint8_t | versionID | 0 | 0-254, 255 is off limits, increments when config structure changes |
| 1601 | uint8_t | disableTSD | 0 | Do not write Time-Series data to file, 1 = TSD writes disabled |
| | uint8_t | standbyLedLevel | 1 | Ranges from 0-255, 0 = 100% off and 255 = 100% on |
| 1602 | uint8_t | alertHoldoffCount | 1 | Ranges from 0-6, Number of levels to skip before alerting the first time |
| 1603 | uint8_t | alertSquelchLevel | 0 | Ranges from 0-255, 0 = No Squelch, N = Alert level to begin SQUELCH |
| 1604 | uint8_t | alertMode | 2 | The formula used to determine alert strength, 0 = No Alert, 1 = Arithmetic Progression (mx+b) , 2 = Geometric Progression (mr^x+b) |
| 1605 | uint8_t | alertStartValue | 0 | Ranges from 0-100, b in "mx + b" or "mr^x + b" |
| 1606 | int8_t | timezoneOffset | -28 | 15 minute increments from utc |
| 1607 | int16_t | accelTareX | 0x0000 | Alert angle vector captured as 14-bit 2's complement, set during calibration |
| 1608 | int16_t | accelTareY | 0x0000 | Alert angle vector captured as 14-bit 2's complement, set during calibration |
| 1609 | int16_t | accelTareZ | 0x4000 | Alert angle vector captured as 14-bit 2's complement, set during calibration |
| 1610 | float | alertScaleFactor | 1 | Any float from 0.0 - 100.0, m in "mx + b" or "mr^x + b" |
| 1611 | float | alertGrowthFactor | 2 | Any float from 0.0 - 100.0, r in "mr^x + b", mode 2 only |
| 1612 | float | alertAngle | 44.8 | The width of the alert zone, any float from 0.0 - 44.8 degrees, negative indicates inverse alertNotification angle (alert if outside the alert zone) |
| 1613 | uint32_t | alertSnoozeTime | 180000 | The amount of time the device will pause notifications after snoozeTaps, ranges from 1000 - 4294967295 ms, 180000 = 180s = 3min |
| 1614 | uint32_t | alertDelayTime | 8000 | The amount of time between alerts, ranges from 1000 - 4294967295 ms, 8000 = 8s |
| 1615 | uint32_t | standbyDelayTime | 5000 | The about of time to wait during each cycle of the state machine task loop, ranges from 1000 - 4294967295 ms, 5000 = 5s |
| 1616 | uint32_t | alertDurationTime | 2000 | The length of time to play an audible alert tone, any value from 25ms to 5000ms, 2000 = 2.0s (valid for tone only) |
| 1617 | uint32_t | alertPattern | 0xFFFFFFFF | The pattern of audible notification to play, any pattern of 32 bits, 0xFFFFFFFF = solid tone, 0x0 = play digital sampled sound file |

| Condition | Definition | Data captured for device reporting and doctor diagnosis |
|---|---|---|
| Snoring | the hoarse vibratory sound that occurs when air flows past relaxed tissues in your throat, causing the tissues to vibrate as you breathe during sleep. | - sound<br>- head vibration |
| Positional Snoring | snoring that increases or decreases in severity or frequency based on sleeping position | - sound<br>- head vibration<br>- sleeping position |
| Upper Airway Resistance Syndrome (UARS) | form of sleep-disordered breathing in which repetitive increases in resistance to airflow within the upper airway lead to brief arousals and daytime somnolence. | - respiratory rate<br>- blood oxygen saturation<br>- heart rate |
| Positional UARS | UARS that increases or decreases in severity or frequency based on sleeping position | - respiratory rate<br>- blood oxygen saturation<br>- heart rate<br>- sleeping position |
| Sleep Apnea (SA) | condition in which your breathing stops and restarts many times while you sleep | - respiratory rate<br>- blood oxygen saturation<br>- heart rate |
| Positional SA | sleep apnea that increases or decreases in severity or frequency based on sleeping position | - respiratory rate<br>- blood oxygen saturation<br>- heart rate<br>- sleeping position |

FIG. 22

THERAPEUTIC METHODS FOR SLEEP RESPIRATORY ISSUES VIA A POSITIONAL THERAPY DEVICE THAT MONITORS A USERS'S HEAD POSITION

CROSS-REFERENCE TO RELATED APPLICATIONS

This application claims the benefit of priority of U.S. Provisional Application No. 63/514,263, filed Jul. 18, 2023, the contents of which are hereby incorporated by reference in their entirety for all purposes.

BACKGROUND

Field

Various embodiments of the present disclosure generally relate to facilitating treatment of sleep respiratory issues. In particular, some embodiments relate to the use of a positional therapy device that may be integrated with a positive airway pressure (PAP) mask system for monitoring a user's sleep position to determine when the user is sleeping in a position outside of a configured positional therapy range to train the user to sleep in a position that reduces their symptoms by providing notifications (e.g., audible and/or haptic notifications) to prompt the sleeper to reposition themselves accordingly.

Description of the Related Art

Nearly half of the adult population snores, indicating a reduction of airflow and increased noise for both the person sleeping and their partner, affecting their quality of their sleep. Many of these snorers suffer from the more serious condition: sleep apnea. When a sleeper has moderate to severe sleep apnea their physician may prescribe the use of a PAP machine (e.g., a continuous PAP (CPAP, auto-adjusting PAP (APAP), and bilevel PAP (BiPAP)). A PAP machine generally uses air pressure to keep a user's breathing airways open during sleep.

Alternatively to a PAP machine, a doctor may suggest positional therapy. Positional therapy is a behavioral strategy to treat sleep respiratory issues, including sleep apnea. For example, if a person's breathing is interrupted primarily when they are sleeping in a particular position (usually on their back), and normal when sleeping in other positions (e.g., on their side or stomach), positional therapy may be used to reduce the amount of time the person sleeps in the particular position in which their nasopharynx, soft palate, and/or tongue collapse and interfere with airflow.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

FIG. 9 is a table illustrating user-configured sleep profile attributes in accordance with an embodiment of the present disclosure.

FIG. 15 is a table illustrating various types of data that may be stored in an in-memory time-series data structure in accordance with an embodiment of the present disclosure.

FIG. 16 is a table illustrating various types of data that may be stored in an in-memory configuration parameters data structure in accordance with an embodiment of the present disclosure.

FIG. 22 is a table illustrating various types of sleep respiratory issues, corresponding definitions, and data captured for positional therapy device reporting and facilitation of diagnosis of a given sleep respiratory issue by a medical professional in accordance with an embodiment of the present disclosure.

DETAILED DESCRIPTION

Figure 1:
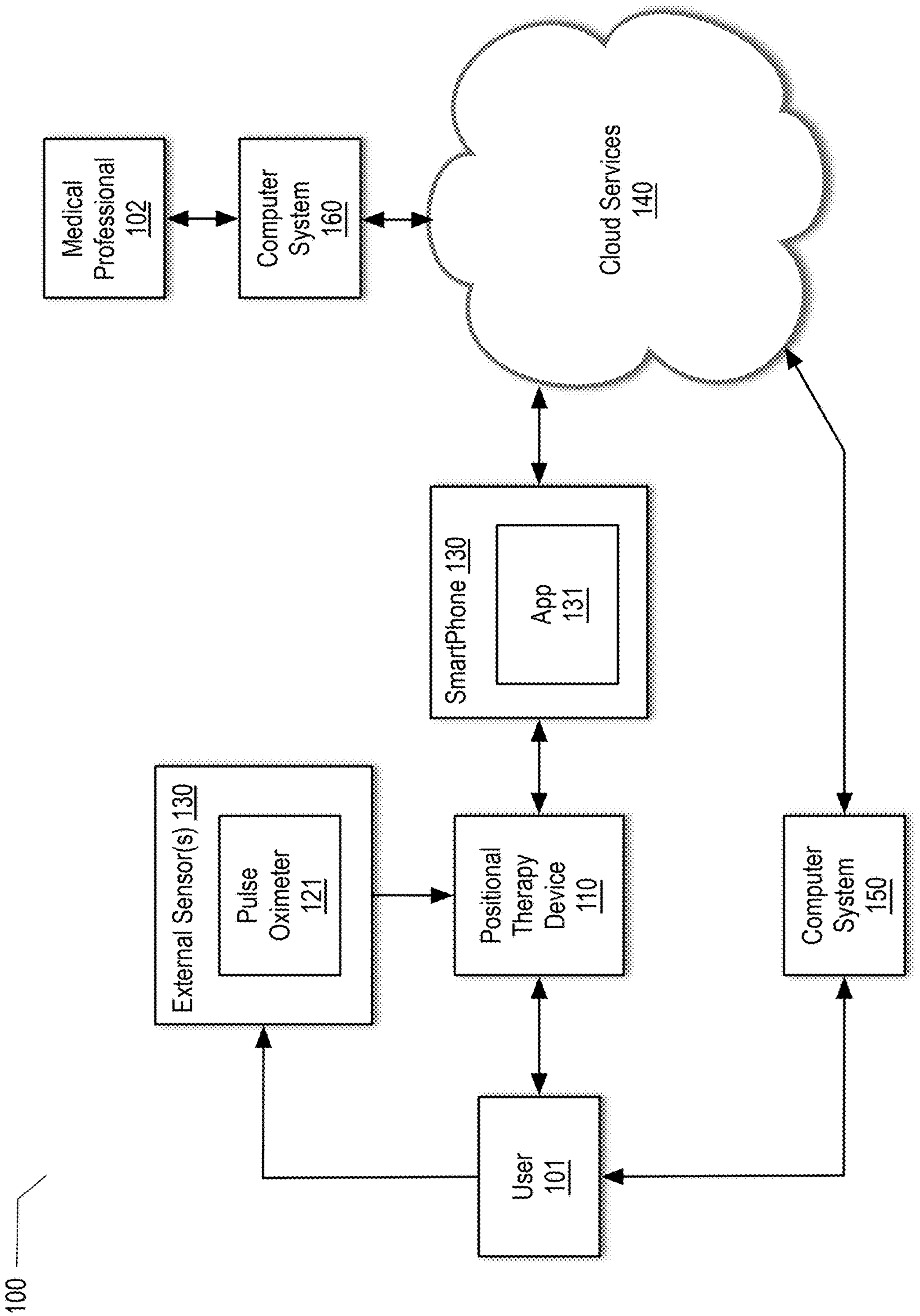
FIG. 1 is a context level diagram illustrating interactions with a system in accordance with an embodiment of the present disclosure.

Systems, devices, and methods are described for delivery of therapy for sleep respiratory issues. Currently, people use backpacks, pillows, tennis balls down the back of the night shirt, and/or haptic notifiers to try to adhere to better sleep positions. Obstacle approaches to positional therapy such as a pillow, backpack, and a tennis ball influence the users to stay off the back through physical discomfort and obstruction of the prone sleeping position. These can cause ribs to be pushed out of alignment and exasperate back and neck skeletal conditions. The user will also experience discomfort when switching from one side to the other, even if they are not stopping to lie on their back, which causes additional unnecessary interruptions to sleep. While haptic notifiers for positional therapy may not cause physical discomfort for its users, the vibratory nature of haptic notification is often startling and extreme to someone in a restful sleep state. This can cause anticipation anxiety when wearing the device, wake the user up completely, and unsettle the user to the point where they cannot continue sleeping. As an alternative to both of the previous methods, audible notification is able to provide lighter less disturbing cues that can leverage the suggestive nature of those in lighter sleep stages, most positional shifting occurs on the lighter sleep stages (N1, N2). As a result, there is no discomfort, no risk to the skeletal structure, less probability of anxiety, and less extreme awakenings, resulting in more contiguous and restful sleep.

PAP treatments, while mostly effective, have poor long term adherence rate for users. This is mostly due to the amount of air pressure needed to treat the Obstructive Sleep Apnea (OSA) sufferer. It is common for users to wake up several times a night with pressure leaks or aerophagia events (air pushed into the user's stomach instead of the lungs). Both are irritating and can increase sleep deprivation. Aerophagia can also be painful and lead to acid reflux and Gastroesophageal reflux disease (GERD). In the majority of cases, positional therapy reduces the severity of airway collapses for a person. With this reduced collapse, combining positional therapy with PAP treatment will allow PAP users to drop their required air pressure to maintain an open airway. With the drop in air pressure, the frequency and severity of the air leaks and aerophagia events will be reduced resulting in more enjoyable and effective treatments and better long term adherence.

Positional therapy devices (e.g., a positional therapy device integrated with a PAP mask or straps) proposed herein seek to address or at least mitigate various of the limitations of prior devices by providing an effective and more sleep conducive method for positional sleep therapy. In accordance with various embodiments described herein, positional therapy can be implemented through notifications (e.g., audible and/or haptic notifications) delivered through an electronic positional therapy device to reduce symptoms of positional sleep respiratory issues. For example, using a positional sensor (e.g., one or more of an accelerometer, a gyroscope, an inertial measurement unit (IMU), and a magnetometer or some combination thereof) along with a processor, the positional therapy device can recognize when a user is out of their programmed sleep position. The sleeper can then be notified through a speaker of the positional therapy device to adjust themselves to a more optimal sleep position for reduced snoring and/or sleep obstruction. The audible notification can consist of various recorded (sampled) and/or synthesized sounds (e.g. voice instructions, animal and environmental sounds, beeps, music, and tones). Additionally, snoring detection may be leveraged through the positional sensor or a microphone to determine if repositioning is necessary. As described further below, the positional therapy device may capture user sleep data (including but not limited to one or more of sleep times, sleep positions, sleep alerts, hear rate, breathing, oxygen, etc.), and positional therapy device operational data. Using wireless networking, the positional therapy device may send captured data to a computer or mobile device for review and further processing. The wireless communication may also be used to receive configurations, notification recordings, and sounds for use on the positional therapy device. Over time, users are conditioned to avoid settling into the sleep positions that result in positional snoring, positional sleep apnea (PSA), and/or positional upper airway resistance syndrome (UARS).

While various examples described herein involve alerting (e.g., providing an audible and/or haptic notification to) a user when a sleep position of the user (e.g., as indicated based on monitoring of a state of a positional sensor of a positional therapy device worn by the user) is outside of a positional sleep therapy alert zone, it is to be appreciated such alerts may also be configured to provide notification when the user is inside of a positional sleep therapy alert zone, or alternatively (independently of the sleep position alerts) such alerts may be provided responsive to detecting the user is snoring or is experiencing a cessation of breathing.

While various examples described herein involve providing audible notifications (e.g., in the form of sampled sounds or tones), which are less jarring to a sleeper than haptic notifications, in some examples the positional therapy device may use haptic notifications or augment audible notifications with haptic notifications, for example, for particularly deep sleepers.

In the following description, numerous specific details are set forth in order to provide a thorough understanding of embodiments of the present disclosure. It will be apparent, however, to one skilled in the art that embodiments of the present disclosure may be practiced without some of these specific details. In other instances, well-known structures and devices are shown in block diagram form.

Terminology

Brief definitions of terms used throughout this application are given below.

The terms "connected" or "coupled" and related terms are used in an operational sense and are not necessarily limited to a direct connection or coupling. Thus, for example, two devices may be coupled directly, or via one or more intermediary media or devices. As another example, devices may be coupled in such a way that information can be passed there between, while not sharing any physical connection with one another. Based on the disclosure provided herein, one of ordinary skill in the art will appreciate a variety of ways in which connection or coupling exists in accordance with the aforementioned definition.

If the specification states a component or feature "may", "can", "could", or "might" be included or have a characteristic, that particular component or feature is not required to be included or have the characteristic.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The phrases "in an embodiment," "according to one embodiment," and the like generally mean the particular feature, structure, or characteristic following the phrase is included in at least one embodiment of the present disclosure, and may be included in more than one embodiment of the present disclosure. Importantly, such phrases do not necessarily refer to the same embodiment.

A "positional therapy device" generally refers to a device that may be worn by a user to help the user sleep in one or more designated favorable positions and/or avoid sleeping in one or more designated unfavorable positions. In one embodiment, in response to determining the user is in one or more designated unfavorable positions or outside of one or more designated favorable positions, the user may be prompted with a notification to adjust their sleeping position. In various examples described herein, a positional therapy device may be worn on a user's head to allow more granular sleep position information to be determined than traditional devices that are worn around the waist or torso. For example, sleeping in the supine position may be fine so long as the user's head is tilted to the right or left of center. In some examples, the positional therapy device may be integrated with a PAP mask or straps. In one embodiment, the positional therapy device may alternatively or additionally be used as a home sleep test device to facilitate diagnosis of a sleep respiratory issue by capturing sleep data for analysis/evaluation by a medical professional.

As used herein, a "positional therapy device" generally refers to a device that includes at least a processor, a speaker, a positional sensor, and potentially one or more other integrated or external sensors. A positional therapy device may be used as a sleep therapy tool to reduce snoring responsively by detecting snoring (through vibration picked up by the positional sensor or snoring sounds picked up by a microphone), prompting the user with an audible notification to adjust their sleeping position. The positional therapy device may alternatively or additionally be used as a positional sleep therapy tool to reduce symptoms associated with sleep respiratory issues by detecting with the aid of the positional sensor when the user is sleeping in a designated unfavorable position and prompting the user with an audible notification to adjust their sleeping position. The positional therapy device may alternatively or additionally be used as a home sleep test device to facilitate diagnosis of a sleep respiratory issue by capturing sleep data for analysis/evaluation by a medical professional.

As used herein, a "positional sensor" generally refers to a sensor that may be used to measure or otherwise determine an orientation of a device within which it is embedded in two-dimensional (2D) space (e.g., roll and pitch) or in three-dimensional (3D) space (e.g., roll, pitch, and yaw). Non-limiting examples of a positional sensor include an accelerometer, an inertial measurement unit (IMU), a gyroscope, a magnetometer, and/or any combination thereof.

As used herein, "sleep position" generally refers to the position of a user of a positional therapy device during a sleep session. In various embodiments described herein, sleep position may refer to an orientation of the user's head in 2D or 3D space, for example, as determined with reference to a positional sensor of the positional therapy device.

A "sleep session" generally refers to a time period during which a positional therapy device, which may be integrated with a PAP mask or straps, is actively monitoring and/or logging one or more sleep attributes of a user of the positional therapy device. In some examples described herein, a sleep session may be manually started by a user (e.g., via user input to an application associated with the positional therapy device vice or via direct input to the positional therapy device) or may be automatically started responsive to one or more predetermined trigger events (e.g., completion of calibration of a pointing angle of the positional therapy device or when a pressure sensor associated with the positional therapy device indicates air pressure is actively being applied by the PAP machine). A sleep session may also be ended manually by the user and/or automatically (e.g., responsive to the positional therapy device being placed in a charging station or dock or when a pressure sensor associated with the positional therapy device indicates air pressure is not actively being applied by the PAP machine).

As used herein, a "sleep respiratory issue" generally refers to a condition in which a sleeper experiences snoring, sleep-disordered breathing, and/or incidents of breathing cessation. These symptoms may be accompanied by, among other things, one or more of headaches (especially when waking up), awakening with a dry mouth, feeling tired or exhausted when waking up, excessive daytime sleepiness, disruptions in brain function (e.g., memory loss, trouble concentrating or difficulty paying attention while awake, and/or other brain-related issues), mood changes (e.g., depression, anxiety, and/or irritability). Non-limiting examples of sleep respiratory issues include snoring, positional snoring, upper airway resistance syndrome (UARS), positional UARS, sleep apnea (SA), positional SA (PSA), obstructive sleep apnea (OSA), positional OSA (POSA), and central sleep apnea.

As used herein, a "speaker" generally refers to any mechanism through which sound may be transmitted or transferred to the ear or otherwise perceived by the ear. As those skilled in the art will appreciate, sound may be transmitted to the ear via sound waves or transferred to the ear through bone conduction. As such, non-limiting examples of a speaker include, (i) a device (e.g., bone conduction headphones, a bone conduction transducer, and/or the like) that converts sounds into vibrations, which are then sent, for example, to the inner ear via a person's skull bone and (ii) a device (e.g., an electgroacoustic transducer) that converts electrical audio signals into a corresponding sound in the form of sound waves.

Example Therapeutic and/or Diagnostic System

FIG. 1 is a context level diagram illustrating interactions with a system 100 in accordance with an embodiment of the present disclosure. In this example, the system 100 includes a positional therapy device (e.g., positional therapy device 110), a mobile device (e.g., a smartphone 130), one or more optional external sensor(s) 120, and cloud services 140. The positional therapy device 110 may be worn in the ear of a user 101 during a sleep session to monitor and receive, log, and/or process various inputs (e.g., blood oxygen saturation (SpO2), pulse data, body temperature, sound and vibration, sleep position, and/or user taps). Some subset of these inputs or other inputs may be received by internal sensors (not shown) integrated within the positional therapy device or indirectly by the positional therapy device 110 through the one or more optional external sensor(s) 120 (e.g., an oximeter or a pulse oximeter). A non-limiting example of an architecture of a positional therapy device is described below with reference to FIG. 2. As described further below, the positional therapy device 110 may be in the form of a low-profile ear bud that sits in the concha of the user's ear. Alternatively, the positional therapy device may be integrated with a PAP mask system as described further below with reference to FIG. 23B.

In one embodiment, the positional therapy device 110 includes a speaker located proximate to a user's ear (or on or near the user's cheekbones) to facilitate prompting the user 101 with an audible notification when the user 101 is in a sleep position that is within a configured positional sleep therapy alert zone. In this manner, over time the user 101, who may have a positional sleep-related breathing disorder or positional sleep reparatory issue may be conditioned or otherwise trained to avoid settling into sleep positions (e.g., within the configured positional sleep therapy alert zone), thereby lessening their symptoms (e.g., occurrences of breathing cessation, gasping, snoring, or other airflow restrictions). As will be appreciated, the positional therapy device 110 may also be used without conditioning, for example, as a home sleep test device that captures sleep data for analysis/evaluation by a medical professional 102. As described further below, in one embodiment, the user 101 may authorize access by a medical professional 102 (e.g., a sleep physician (or somnologist), a pulmonologist, or their medical staff) to user sleep reports stored in the user's cloud account, for example, via their own computer system 160.

The positional therapy device 110 may also be useful for other types of users, with or without sleep respiratory issues. For example, a pregnant woman in her third trimester may desire to avoid sleeping on her back, a person with chiropractic issues may be advised to sleep in a specific position, a patient that uses a continuous positive airway pressure (CPAP) machine or a dental advancement device may want to ensure they sleep in a specific position, and a patient that experiences gastroesophageal reflux disease (GERD) or benign paroxysmal positional vertigo (BPPV) may want to avoid particular sleeping positions.

In one embodiment, the positional therapy device 110 may be configured for multiple modes of operation, including a notification (therapeutic) mode and a logging (or diagnostic) mode. In the logging mode, audible notifications by the positional therapy device 110 may be disabled to allow the user to acclimate to sleeping while wearing the positional therapy device 110 and/or facilitate usage of the positional therapy device 110 as a home sleep test. As described further below, in the logging mode, the positional therapy device 110 may perform repeated measurements over time of multiple sensors associated with the positional therapy device 110 and log observations regarding existence or non-existence of breathing cessation and one or more of a position of the user's head, a breathing rate of the user, a heart rate of the user, a snoring state of the user, a body temperature of the user, and an oxygen saturation of the blood of the user to allow the system 100 to be used to (i) facilitate diagnosis by a sleep or respiratory professional (e.g., a sleep physician (or somnologist) or a pulmonologist) of the user 101 as having a sleep respiratory issue based on the logged observations, (ii) identify the user as potentially having a sleep respiratory issue based on application of a set of predetermined or configurable criteria to the logged observations, and/or (iii) otherwise be used as part of a home sleep test.

According to one embodiment, the smartphone 130 includes a mobile app (e.g., app 131) associated with the positional therapy device 110. The mobile app may facilitate, among other things, visualization of sleep session metrics, storage of time-series data collected by the positional therapy device 110 locally and/or to the cloud services 140, and/or configuration of various positional therapy device parameters (e.g., mode of operation (logging vs. notification), the size (e.g., width and/or depth) of the alert zone, the zero-point position or center of the alert zone, monitoring interval, etc.) and/or user preferences/profiles. A non-limiting example of an architecture of a mobile app is described below with reference to FIG. 3.

The cloud services 140 may be implemented within a public cloud service provider (e.g., Amazon Web Services (AWS), Google Cloud Platform (GCP), Microsoft Azure, or the like) provide, through interactions with the app 131 or a browser of a computer system 150, among other features, access to summaries, reports, and/or recommendations based on the logged data and the ability to integrate with medical systems, applications, and/or devices or otherwise export logged data in various data interchange formats (e.g., comma-separated values (CSV), JavaScript Object Notation (JSON), extensible markup language (XML), open source clinical application resource (OSCAR), and/or the like). Further description regarding examples of various features and functionality that may be provided by the cloud services 140 is provided below with reference to FIG. 4.

While in the context of the present example, a mobile device is described as running an app 131 associated with the positional therapy device 110, it is to be appreciated various other mobile devices or portable computing devices may be used to interact with the positional therapy device 110, for example, including a tablet computer and a laptop computer.

Example Positional Therapy Device Architecture

Figure 2:
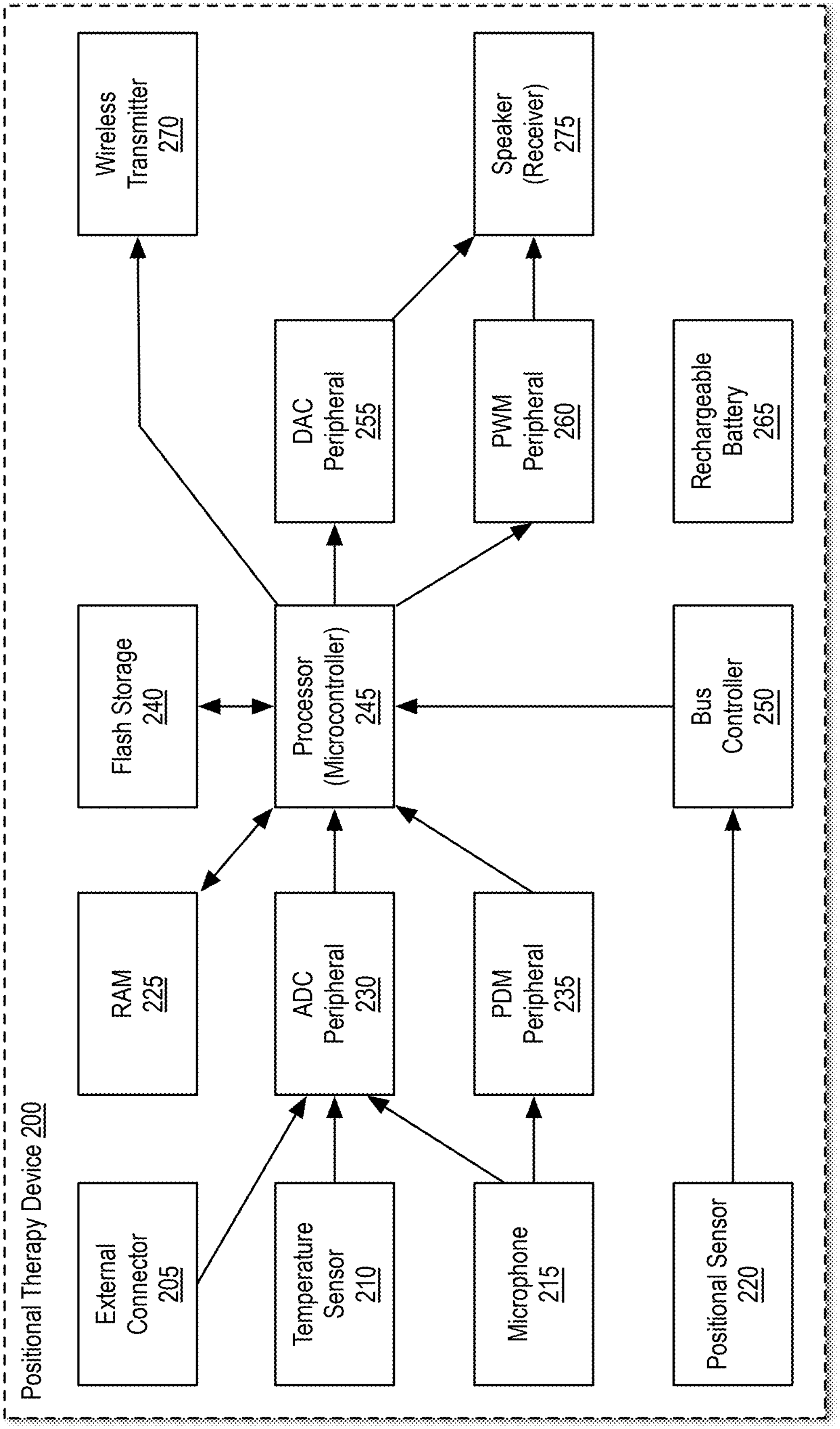
FIG. 2 is a block diagram illustrating a positional therapy device in accordance with an embodiment of the present disclosure.

FIG. 2 is a block diagram illustrating a positional therapy device 200 in accordance with an embodiment of the present disclosure. Notably, components of the positional therapy device 200 (which may be analogous to positional therapy device 110) are meant only to exemplify various possibilities. In no way should example positional therapy device 200 limit the scope of the present disclosure. In the context of the present example, positional therapy device 200 is shown including an external connector 205, a temperature sensor 210, a microphone 215, a positional sensor 220, a main memory (e.g., a random access memory (RAM) 225 or other dynamic storage device), an analog-to-digital converter (ADC) peripheral 230, a pulse density modulation (PDM) peripheral 235, flash storage 240, a processing resource (e.g., a processor or microcontroller 245, a central processing unit (CPU), or other hardware logic circuitry), a bus controller 250, a digital-to-analog converter (DAC) peripheral, a pulse width modulation (PWM) peripheral 260, a rechargeable battery 265, and a speaker (receiver) 275.

The components of the positional therapy device 200 on the left-hand side may represent components for receiving inputs directly or indirectly from a human user of the positional therapy device 200. For example, the external connector 205 may represent an electrical connector (e.g., in the form of external contact pads) to which one or more of the optional external sensors (e.g., external sensor(s) 120) may be coupled to the positional therapy device 200. The temperature sensor 210 may measure the body temperature of the user (e.g., user 101) of the positional therapy device 200. The microphone 215 may be used to receive environmental sounds or sounds (e.g., breathing sounds, heart sounds, gasping, snoring, etc.) made by the user.

The positional sensor 220 may be used to determine a sleep position of the user, for example, representing an orientation of the user's head in two-dimensional (2D) or three-dimensional (3D) space. Interrupts (e.g., representing the detection of movement of the user, or input taps from the user) and other state information (e.g., X, Y, and Z angles/vectors) measured by the positional sensor may be communicated to the processor via a bus (e.g., an inter-integrated circuit (I2C) bus or a serial peripheral interface (SPI) bus) managed by the bus controller 250. As those skilled in the art will appreciate a number of different types of sensors may be used for this purpose including one or more of an accelerometer, an inertial measurement unit (IMU), a gyroscope, and a magnetometer or some combination of two or more of the foregoing. As described below with reference to FIGS. 10A-F, the orientation may be represented in the form of one or more of roll (rotation about a front-to-back axis, for example, the Y axis), pitch (rotation about a side-to-side axis, for example, the Z axis), and yaw (rotation about the vertical axis, for example, the X axis).

The main memory may be used for storing instructions (e.g., microcode) to be executed by the processor 245. Main memory may also be used for variables, stack data, cached registers, communication buffers, or temporarily storing information (e.g., time-series data and/or configuration parameters) while such information is incrementally persisted to flash storage 240. Non-limiting examples of the various types of data that may be stored in memory in a time-series data structure and an in-memory configuration parameters structure are described below with reference to FIGS. 16 and 17, respectively.

The ADC peripheral may be used to convert analog signals received through analog sensors (e.g., an external sensor coupled to the external connector 205, the temperature sensor 210, and/or an analog microphone) to a digital form so that it can be read and processed by the processor 245.

The PDM peripheral 235 may be used to convert amplitude values of an encoded analog signal to a digital bitstream (a stream of decimated samples) so that it can be read and processed by the processor.

Flash storage 240 (or some other form of nonvolatile memory) may be used to maintain the integrity of stored data (e.g., time-series data and/or configuration parameters), for example, until such data may be persisted to the cloud (e.g., cloud services 140) via a wireless connection with a portable computing device (e.g., smartphone 130) provided by the wireless transmitter 270. For example, in one embodiment, the wireless transmitter 270 may be deactivated while being worn by the user during a sleep session and then data stored or logged during the sleep session may be transferred to the cloud upon completion of the sleep session.

The processing resource (e.g., processor 245) is generally responsible for receiving data from various sources (e.g., the ADC peripheral 230, the PDM peripheral 235, and the bus controller 250), processing and/or organizing the data, making decisions based on the data, managing one or more state machines, and storing results of the processing and/or organization of the data to RAM 225 and/or flash storage 240 as appropriate. The processing resource may be represented in a number of different forms of electronic circuitry, for example, a microcontroller, a microprocessor, one or more CPU cores, an application-specific integrated circuit (ASIC), a field programmable gate array (FPGA), and the like. Non-limiting examples of processors/microcontrollers that are suitable for embedded systems requiring high performance and low power consumption include RISC-V-based processors/microcontrollers and ARM processors/microcontrollers A non-limiting example of the various tasks and communications between/among the tasks that may be executed by an operating system (e.g., a real-time operating system (RTOS)) running on the processing resource is described below with reference to FIG. 5. A non-limiting example of various positional therapy device states is described below with reference to FIG. 7.

The DAC peripheral 255 may be used to convert digital signals received from the processor 245 to analog, for example, to provide audible notifications to the user. Alternatively, or additionally the PWM peripheral 260 may be driven by the processing resource to convert a digital bitstream to analog (e.g., amplitude values of an analog signal) to provide such audible notifications.

The wireless transmitter 270 may be used to exchange wireless communications between the positional therapy device 200 and a portable computing device or a mobile device (e.g., smartphone 130). According to one embodiment, the wireless transmitter 270 represents a Bluetooth low energy (BLE) transmitter that may be used, for example, to send data captured/logged by the positional therapy device 200 to the portable computing device or the mobile device for review and/or for further processing. According to one embodiment, file transfer from the positional therapy device 200 to the portable computing device or the mobile device may be performed via BLE, universal asynchronous receiver/transmitter (UART) over BLE, or Zmodem over BLE. Wireless communication may also be used to receive configurations, notification recordings, and sounds for use by the positional therapy device 200, for example, to alert the user when they are sleeping in an undesirable position (e.g., within the configured positional sleep therapy alert zone).

The speaker 275 may be used to provide an audible alert to the user, for example, indicating the user is in an undesirable sleep position or to otherwise prompt the user to alter their sleep position. In one embodiment, when the user is wearing the positional therapy device 200, the speaker 275 is located proximate to (e.g., within about 0 to 5 millimeters) or within an auditory canal of the user's ear. In this manner, the audible notifications intended for the user will not be heard by a sleep partner of the user. Alternatively, for example, when the speaker 275 is a bone conduction transducer, the speaker 275 may be placed in front of the ear or behind the ear or so as to engage the jawbone or mastoid.

The positional therapy device 200 is also shown including rechargeable battery 265. According to one embodiment, charging of the rechargeable battery 265 may be commenced responsive to detection of the positional therapy device 200 having been placed within a dock (not shown). In alternative embodiment, the positional therapy device 200 may make use of disposable (or single-use) batteries.

While in the context of the present example, various examples of internal sensors (e.g., temperature sensor 210, microphone 215, and positional sensor 220) are shown, it is to be appreciated some examples may include more or fewer internal sensors or one or more external sensors (e.g., external sensor(s) 120) may be used in place of one or more of the internal sensors or in addition to the internal sensors. For example, in some embodiment, the positional therapy device 200 may include or be configured to be coupled (e.g., via external connector 205) to an electrocardiogram (ECG or EKG) and/or an electroencephalogram (EEG).

According to one embodiment, to facilitate reduction in size, cost, and/or power, usage, for example, when the positional therapy device has a small form factor, native functionality provided by the microcontroller may be favored over supplementing such native functionality. For example, if a given implementation makes use of a microcontroller having an integrated ADC peripheral, an analog microphone may be utilized, whereas if the microcontroller includes an integrated PDM peripheral, a PDM microphone may be utilized.

For embodiments in which the positional therapy device is integrated with a PAP mask system (e.g., within a mask and/or straps), size constraints may be relaxed a bit, thereby allowing the use of supplemental functionality, increased RAM, and/or increased flash storage. Assuming such relaxed size constraints, the positional therapy device, such as the positional therapy device integrated with a PAP mask system described below with reference to FIGS. 23B and 23D may also include a removable secure digital (SD) card or other type of multimedia card (MMC) to facilitate storage of additional audio, sound samples, and storage for time-series data. For example, such an embodiment might use a 128 GB SD card for significant storage space. Additionally, a larger battery would allow for the playing of audio for the entire duration of the sleep session or for a time specified by the user.

Example Mobile App Architecture

Figure 3:
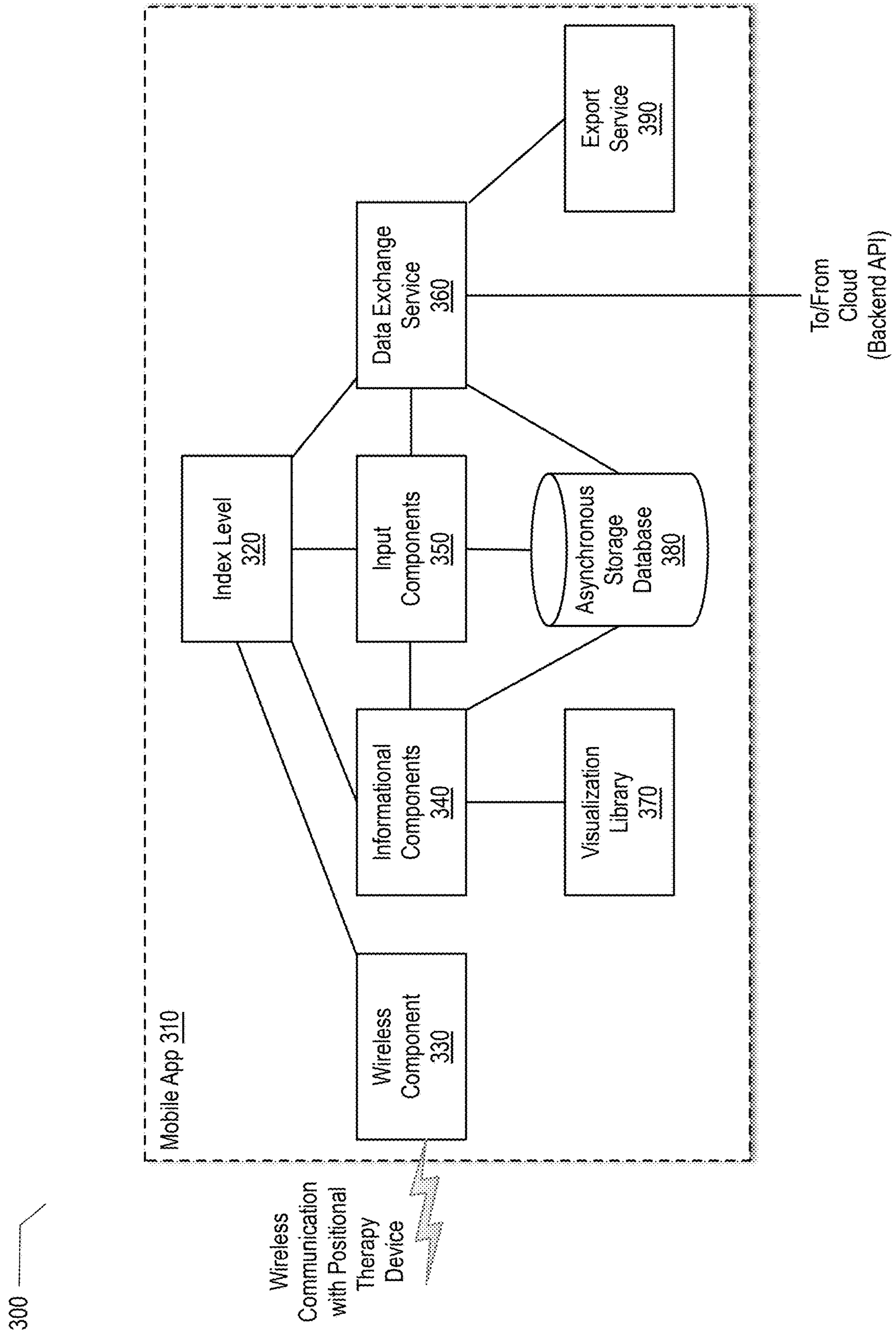
FIG. 3 is a block diagram illustrating an architecture of a mobile app in accordance with an embodiment of the present disclosure.

FIG. 3 is a block diagram illustrating an architecture 300 of a mobile app 310 in accordance with an embodiment of the present disclosure. The mobile app 310 (which may be analogous to app 131) may represent a mobile operating system app (e.g., an iPhone operating system (iOS) app, iPadOS app, or android app) available via an app store or an app marketplace (e.g., Google Play or the Apple App Store). In the context of the present example, the mobile app 310 is shown including an index level 320, a wireless component 330, informational components 340, input components 350, a data exchange service 360, a visualization library 370, an asynchronous storage database 380, and an export service 390.

The index level 320 may represent the home page or hub of the mobile app 310 that indexes into and connects to the other components.

The visualization library 370 may include user interface elements and/or modules for creating data visualizations, reports, aggregations and/or summaries of stored sleep sessions. The visualization library 370 may also facilitate providing the user (e.g., user 101) with real-time or near real-time visual feedback relating to information (e.g., breathing rate, heart rate, body temperature, oxygen saturation, etc.) received from an associated positional therapy device (e.g., positional therapy device 110 or 200), for example, via wireless component 330 (e.g., a Bluetooth component).

Informational components 340 may provide access to training materials and/or applications (including content developed by the vendor of the positional therapy device and/or by third parties). Informational components 340 may also provide recommendations and/or feedback based on previous sleep sessions, for example, loaded from the cloud (e.g., cloud services 140) and locally stored within the asynchronous storage database 380.

Input components 350 may include forms for collecting data from the user, for example, relating to factors (e.g., caffeine and/or alcohol consumption, medications, sleep environment, exercise, stress level, food intake, water intake, and the like) that may impact sleep quality and how they feel after the most recent sleep session. For example, after each sleep session, the user may be prompted to fill out a form or respond to questions associated with a sleep questionnaire associated with the sleep session. The user may also be provided with the ability to update/revise responses for a previous sleep questionnaire associated with a prior sleep session.

The data exchange service 360 may be responsible for facilitating communication with backend services (e.g., cloud services 140) via an application programming interface (API) exposed by the backend services, including taking data structured in accordance with a first (source) schema used by the mobile app 310 and transforming it into a second (target) schema used by the backend services and vice versa to support storing/retrieving data to/from the cloud.

The export service 390 may be used to create exports for external medical applications (e.g., an electronic medical record (EMR) solution) in an appropriate format (e.g., CSV, OSCAR, or the like). Such data exports of time-series data associated with one or more user sleep sessions may also facilitate evaluation of a user's symptoms or diagnosis of a sleep respiratory issue by a medical professional.

Example Cloud Services

Figure 4:
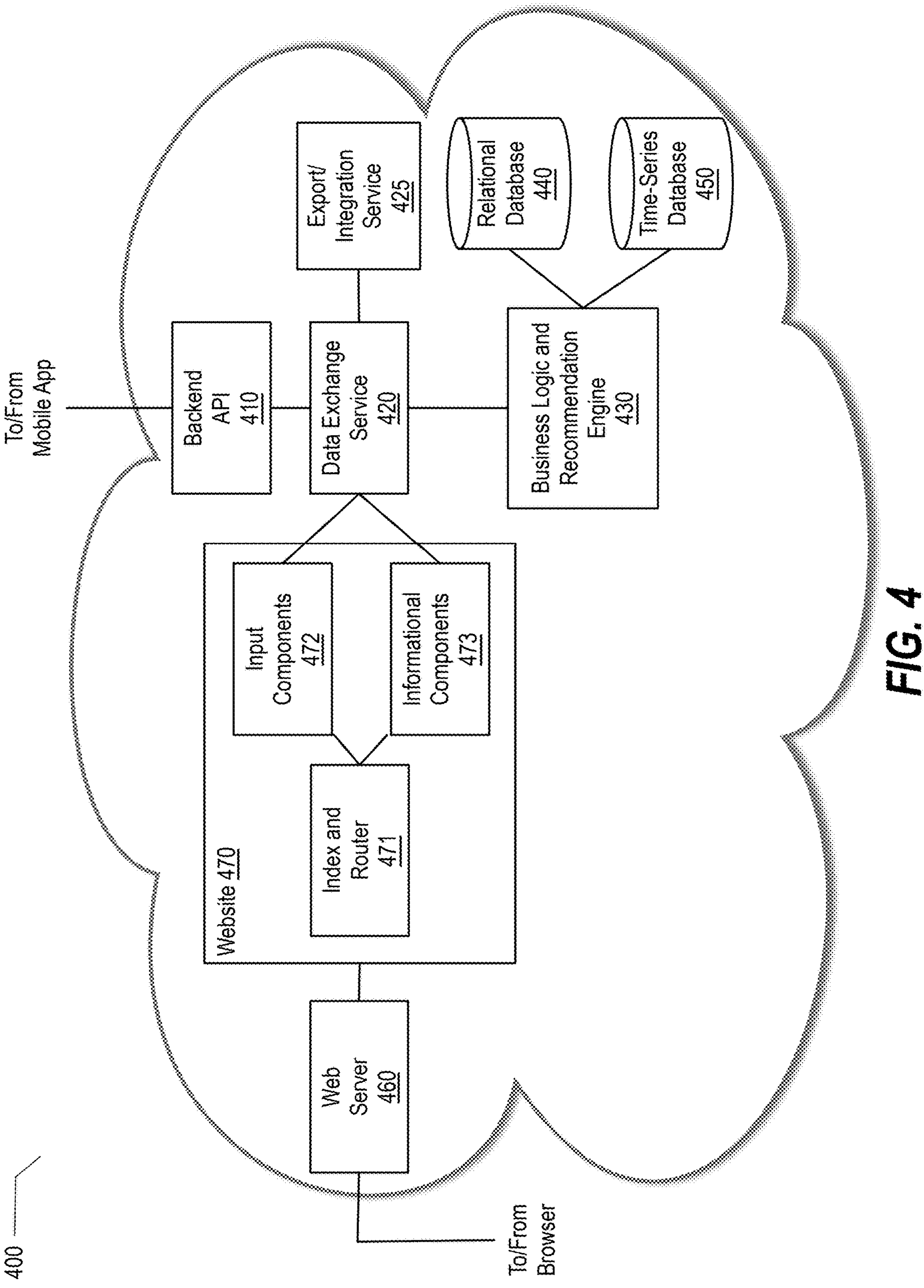
FIG. 4 is a block diagram illustrating cloud services in accordance with an embodiment of the present disclosure.

FIG. 4 is a block diagram illustrating cloud services 400 in accordance with an embodiment of the present disclosure. Cloud services 400 (which may be analogous to cloud services 140) may represent services provided to a user (e.g., user 101) via a public cloud service provider, for example, in relation to usage of a positional therapy device (e.g., positional therapy device 110 or 200, analysis of sleep data collected/logged by the positional therapy device, and/or recommendations regarding how to achieve better sleep based on evaluation of user completed sleep questionnaires, device parameters established by the user, and/or past or current alert or notification profiles (which may also be referred to herein as sleep profiles). In the context of the present example, cloud services 400 include two separate entry points, (i) a web server 460, which may be used to access cloud services 400 via a browser and (ii) a backend API 410 through which a mobile app (e.g., mobile app 131 or 310) may access the cloud services 400.

The cloud services 400 may also include a website 470, a data exchange service 420, export/integration service 425, a business logic and recommendation engine 430, a relational database 440, and a time-series database 450. The website 470 is shown including an index and router 471, input components 472, and informational components, which may generally correspond to the functionality provided by the index level 320, input components 350, and informational components 340 of FIG. 3.

The data exchange service 420 (like data exchange service 360) may be responsible for facilitating communication with the mobile app via the backend API 410, including, for example, taking data structured in accordance with a source (first) schema used by the cloud services 400 and transforming it into a target (second) schema used by the mobile app and vice versa to support storage of data received from the mobile app and retrieval of data requested by the mobile app.

The business logic and recommendation engine 430 may be responsible for storing, among other things, user data, profiles, and answers to sleep questionnaires within the relational database 440 and storing time-series data associated with sleep sessions to the time-series database 450. The business logic and recommendation engine 430 may also employ machine-learning (ML) techniques to make recommendations to the user regarding how to improve their sleep and/or usage of the positional therapy device. For example, based on an observed correlation between days on which the user consumed alcohol and/or caffeine and feedback from the user regarding not feeling well-rested the following morning, the business logic and recommendation engine 430 may recommend the user abstain from consuming alcohol and/or caffeine. Similarly, based on the user's alert profile, a number of times the user was alerted by the positional therapy device for being in a sleep position within their configured positional sleep therapy alert zone, and feedback from the user indicating existence of excessive daytime sleepiness, the business logic and recommendation engine 430 may suggest the user adjust one or more parameters of the alert profile, for example, increasing or decreasing the size of the positional sleep therapy alert zone, increasing or decreasing the volume of alerts (audible notifications), increasing or decreasing a number of alerts before disabling or squelching the alerts, changing a type of sound or pattern of sounds associated with the alerts, and/or increasing or decreasing a ramp associated with a time delay change between alerts or a volume level change between alerts.

The export/integration service 425 (like export service 38) may be used to create exports for use by and/or integration with external medical systems, devices, or applications (e.g., an EMR solution) by, for example, exporting the logged time-series data in an appropriate format (e.g., CSV, OSCAR, or the like). Such data exports of time-series data associated with one or more user sleep sessions may also facilitate evaluation of a user's symptoms or diagnosis of a sleep respiratory issue by a medical professional.

Example Task Communication

Figure 5:
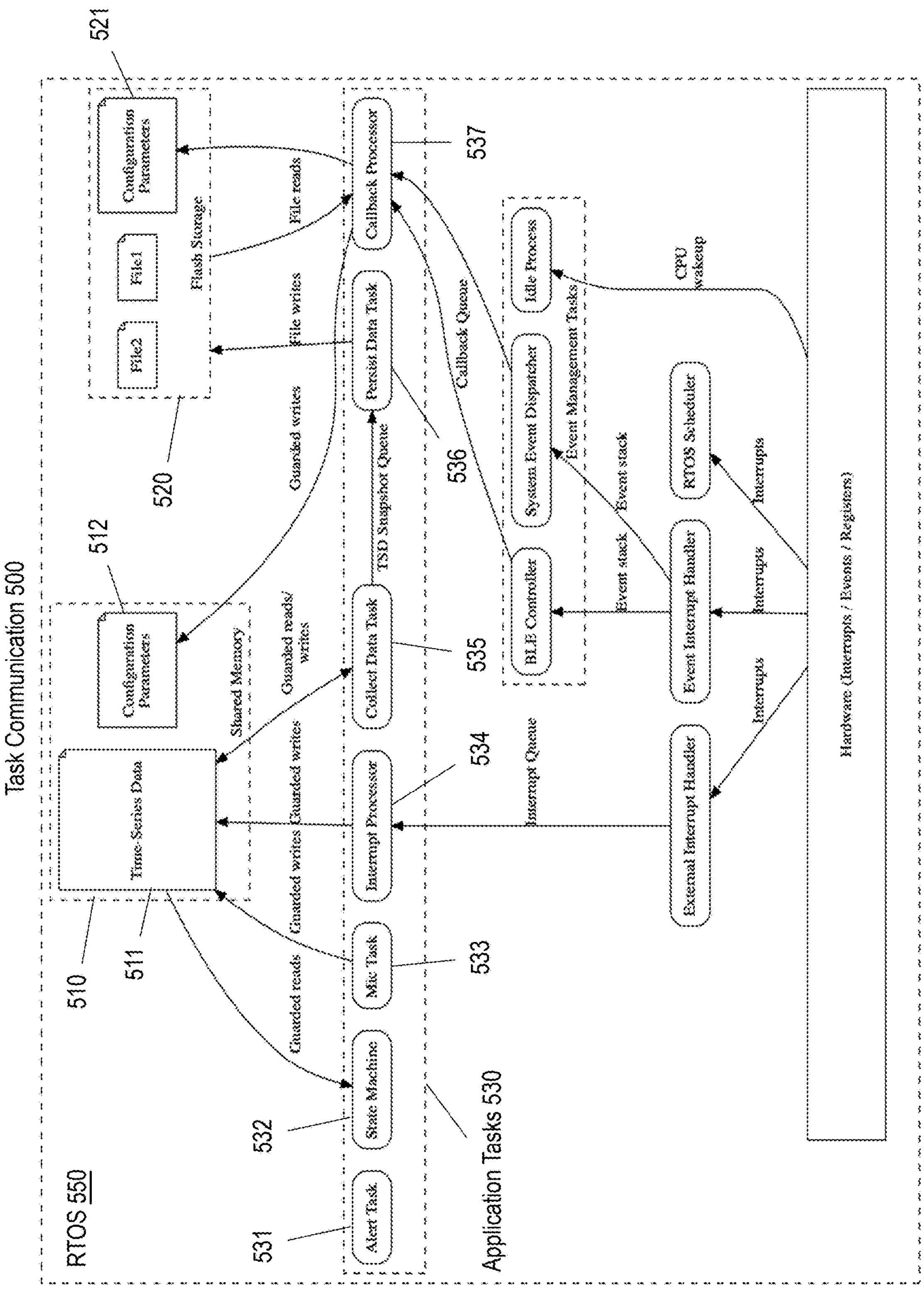
FIG. 5 is a block diagram illustrating task communication involving various application tasks in accordance with an embodiment of the present disclosure.

FIG. 5 is a block diagram illustrating task communication 500 involving various application tasks 530 in accordance with an embodiment of the present disclosure. In the context of the present example, it is assumed a processing resource (e.g., processor or microcontroller 245) of a positional therapy device (e.g., positional therapy device 110 or 200) executes a real-time operating system (e.g., RTOS 550). The RTOS 550 may receive interrupts and events, including, for example, time-based interrupts from in-memory registers that drive the RTOS 550 or interrupts or events from various internal or external sensors (e.g., oximeter 121, temperature sensor 210, microphone 215, and positional sensor 220), microcontroller devices (e.g., wireless transmitter 270), and/or integrated microcontroller peripherals (e.g., ADC peripheral 230, PDM peripheral 235, DAC peripheral 255, and PWM peripheral).

The application tasks 530 may make use of a shared memory 510 and flash storage 520 managed by the RTOS 550. According to one embodiment, the shared memory 510, for example, within a RAM (e.g., RAM 225) may be used to store time-series data 511 in a shared data structure accessible by the application tasks 530. A non-limiting examples of time-series data 511 are described below with reference to FIG. 15. Configuration parameters 512 (representing a copy of configuration parameters 521) may also be stored within the shared memory 510 for use by those of the application tasks 530 having a need. The flash storage 520 may be used by the persist data task 536 to persist snapshots of the time-series data 511, for example, corresponding to sleep data collected during a given monitoring interval in the form of files to be transferred via a wireless transmitter (e.g., wireless transmitter 270) to an intermediate computer system, for example, computer system 150 or a mobile device (e.g., smartphone 130) for storage to the cloud (e.g., cloud services 140 or 400). The flash storage 520 may also store configuration parameters 521. The configuration parameters 521 may include parameters that configure the operation of the positional therapy device. As described further below, some of the configuration parameters 521 may be set based on user configured sleep profile attributes. Non-limiting examples of configuration parameters 512 and 521 are described below with reference to FIG. 16. Non-limiting examples of user configured sleep profile attributes are described below with reference to FIG. 9.

When nothing is scheduled and no interrupts are happening, the RTOS 550 may perform an idle process (which shuts down various clocks, buses, components and peripherals to save power). When interrupts or events are present, the RTOS 550 may route them to corresponding interrupt handlers (e.g., an external interrupt handler, an event interrupt handler, or an RTOS scheduler). The event interrupts may be handed off through an event stack to higher-level tasks, for example, which may manage, among other things, BLE communications and the universal serial bus (USB) connection coming online (e.g., representing the positional therapy device being placed in the dock). External interrupts may be added to an interrupt queue for handling by an interrupt processor task 534.

In the context of the present example, the application tasks 530 include an alert task 531, a state machine task 532, a microphone task 533, the interrupt processor task 534, a collect data task 535, a persist data task 536, and a callback processor task 537. As described further below, the alert task 531 may be started as needed, for example, to generate alerts in the form of audible sound to a user (e.g., user 101) of the positional therapy device via a speaker (e.g., speaker 275). Similarly, the microphone task 533 may be started as needed, for example, responsive to an interrupt from a microphone (e.g., microphone 215) of the positional therapy device indicating the microphone has detected sound, thereby allowing the sound to be processed, evaluated, classified (e.g., as a breathing sound, as an environmental sound, as a heart sound, etc.), logged, and/or recorded as appropriate. The interrupt processor task 534 may monitor for and handle hardware interrupts (e.g., from internal or external sensors), for example, representing the availability of new or changed sensor data to be logged within the time-series data 511. A given external interrupt may represent a state change indicative of user movement received from a positional sensor (e.g., positional sensor 220), data ready from a positional sensor (e.g., positional sensor 220), a change in body temperature measured by a temperature sensor (e.g., temperature sensor 210), a change in SpO2 measured by an oximeter or a pulse oximeter (e.g., pulse oximeter 121), detection of sound via a microphone (e.g., microphone 215). The logging of sensor data (e.g., by the microphone task 533 and the interrupt processor task 534) to the time-series data 511 may be serialized to avoid concurrent writing by multiple application tasks 530, for example, by way of guarded writes (e.g., using a write lock, such as a semaphore or mutex).

The collect data task 535 may record data from various sensors and registers on a regular basis and may periodically (e.g., at the end of every monitoring interval) extract a snapshot of the current time-series data 511 generated during the current monitoring interval and queue it for storage to the flash storage 520 by the persist data task 536. According to one embodiment, the persist data task 536 runs periodically (e.g., every couple minutes or so) and appends the queued snapshot into files within the flash storage 520 in which each file may represent sleep data collected during one sleep session.

The callback processor 537 may be responsible for handling events relating to wireless data received from the intermediate computer system. The wireless data may represent BLE events, for example, receipt of a BLE packet or a BLE command (e.g., a calibration command, a parameter configuration, etc.) associated with a BLE controller. The callback processor may receive one or more configuration parameters 521 and make them accessible to the other application tasks 530 in the form of configuration parameters 512 by copying them to the shared memory 510. The configuration parameters 521 may be modified via an application (e.g., app 131 or mobile app 310) associated with the positional therapy device and may be received by the positional therapy device from the intermediate computer system via wireless communication. The callback processor 537 may also be responsible for transferring the files of time-series data to the intermediate computer system, for example, via a BLE controller. The files may then be subsequently transferred from the intermediate computer system to the cloud, for example, via the application.

The state machine task 532 may be responsible for determining the current state of the positional therapy device (e.g., an alert or alarm state, a standby state, etc.), periodically monitoring the time-series data 511 and the configuration parameters 512 (e.g., each monitoring interval), and making decisions on actions to take based on observations made regarding the time-series data 511, the configuration parameters 512, and a set of rules (not shown). A non-limiting example of the conceptual flow of the state machine task 532 encoded by the set of rules is described further below with reference to FIG. 6.

While in the context of the present example, the positional therapy device is described as a self-contained device that locally makes decisions regarding actions to take based on the current state of the positional therapy device, new data (e.g., time-series data and/or configuration parameters), and a set of rules, it is to be appreciated in alternative embodiments, processing may be performed in a distributed manner with a first subset of the processing (e.g., data collection and alerting) being performed by the positional therapy device and a second subset of the processing (e.g., evaluation of the collected data and determining an action to take) being performed by the application. For example, the positional therapy device may stream sensor data (e.g., position data received from the positional sensor) to the application and receive direction from the application regarding what action, if any, to perform.

Example Positional Therapy Device State Machine Flow

Figure 6:
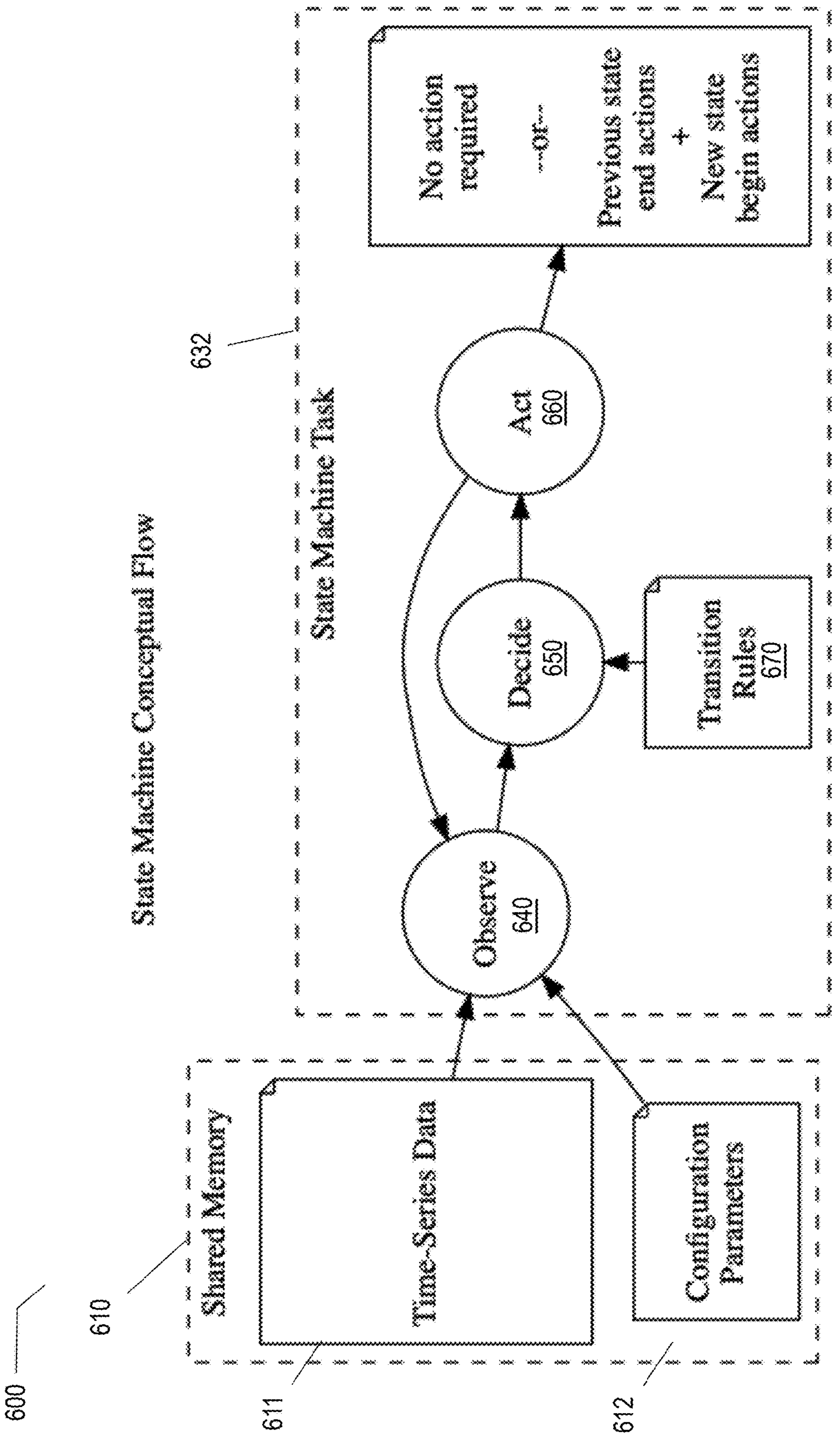
FIG. 6 is a block diagram conceptually illustrating state machine flow in accordance with an embodiment of the present disclosure.

FIG. 6 is a block diagram conceptually illustrating state machine flow 600 in accordance with an embodiment of the present disclosure. According to one embodiment, the state machine flow 600 is executed by a processing resource (e.g., processor or microcontroller 245) of a positional therapy device (e.g., positional therapy device 110 or 200). The state machine flow 600 may represent the transitions between states of a state machine task 632 (which may be analogous to state machine task 532). In the context of the present example, the various phases of the state machine task 632 include an observe phase 640, a decide phase 650, and an act phase 660. The observe phase 640 evaluates time-series data 611 (which may be analogous to time-series data 511) and configuration parameters 612 (which may be analogous to configuration parameters 512) stored within shared memory 610 (which may be analogous to shared memory 510). Based on the sleep data collected and written to the time-series data 611, for example, by a set of application tasks (e.g., application tasks 530) and/or availability of one or more updated values for the configuration parameters 612, the state machine task 632 transitions from the observe phase 640 to the decide phase 650. According to one embodiment, the cadence at which new data is available in the time series data 611 (e.g., sampled or read from the various sensors of the positional therapy device and stored to the time-series data 611) and hence how frequently the state machine task 632 runs may be configured via a standby delay time specified within the configuration parameters 612.

The decide phase 650 is responsible for making a decision regarding whether to transition from one positional therapy device state to another based on the new data observed and a set of transition rules 670, which may be expressed in the form of conditional expressions involving one or more variables. For example, when the new data represents a sleep position (e.g., head orientation) of the user (e.g., user 101) that is within a sleep therapy alert zone (which may also be referred to herein simply as an alert zone) established by the user, the state machine task 632 may cause the positional therapy device state to transition from a standby state to an alarm state during which the user may be provided with an audible notification to prompt the user to alter their sleep position. Non-limiting examples of positional therapy device states and the set of transition rules 670 are described further below with reference to FIG. 7. After a decision has been made regarding whether to transition to a new positional therapy device state or remain in the current (previous) positional therapy device state, the state machine task 632 transitions from the decide phase 650 to the act phase 660.

The act phase 660 is responsible for determining whether action is called for based on the prior positional therapy device state and the new positional therapy device state. When changing positional therapy device states (e.g., the previous positional therapy device state and the new positional therapy device state differ), the act phase 660 causes the end actions from the previous positional therapy device state to be performed and the begin actions for the new positional therapy device state to be performed. For example, when transitioning from the standby state to the alarm state, an alert task (e.g., alert task 531) may be started. After processing associated with the act phase 660 is completed, the state machine task 632 loops back to the observe phase 640 and the observe, decide, act pattern continues at the configured cadence.

While in the context of the present example, the state machine task 632 is described as observing new data in the time-series data 611 and/or the configuration parameters 612, deciding an appropriate positional therapy device state transition to make, if any, based on the observations and the transition rules 670, and carrying out the appropriate action in the act state 660, as noted above, in other examples, processing may be distributed between the positional therapy device and the application. For example, the positional therapy device may collect and log time-series data, stream the logged time-series data to the application for processing by the application, and receive and perform actions as directed by the application.

Example State Transition Diagram Among Device States

Figure 7:
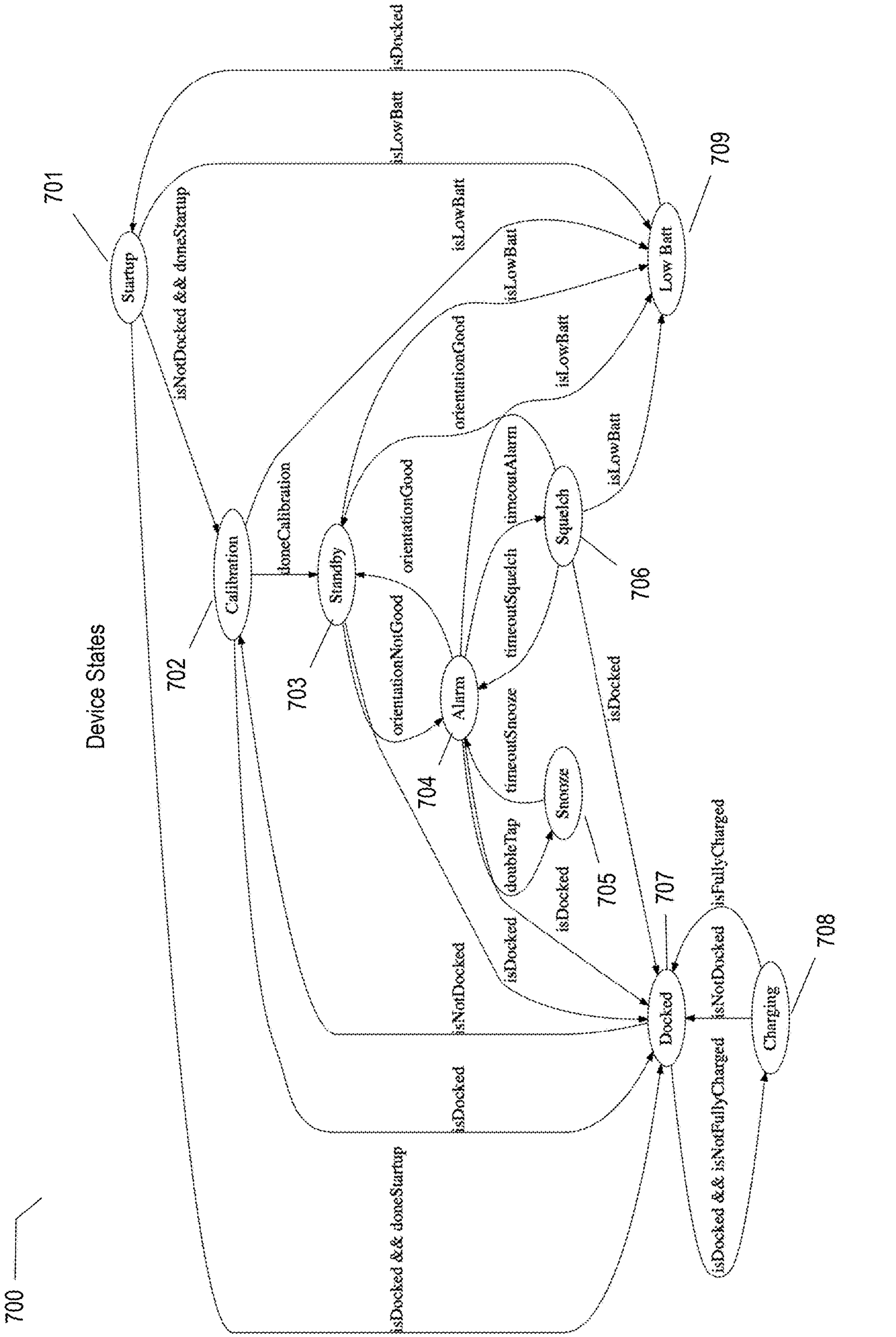
FIG. 7 is a state transition diagram illustrating positional therapy device states in accordance with an embodiment of the present disclosure.

FIG. 7 is a state transition diagram illustrating positional therapy device states 700 in accordance with an embodiment of the present disclosure. In the context of the present example, the positional therapy device states 700 include a startup state 710, a calibration state 720, a standby state 703, an alarm state 704, a snooze state 705, a squelch state 706, a docked state 707, a charging state 707, and a low battery state 709. The edges between the states represent a non-limiting example of the transition rules 670 of FIG. 6.

The calibration state 702, the standby state 703, the alarm state 704, the snooze state 705, and the squelch state 706 represent normal operating conditions of the positional therapy device (e.g., positional therapy device 110 or 200). The docked state 707 and the charging state 708 represent states in which the positional therapy device is in the dock (or charging station). The startup state 701 and the low battery state 709 are states for handling special cases.

The positional therapy device (e.g., positional therapy device 110 or 200) may perform startup processing, for example, booting and loading of the operating system (e.g., RTOS 550) in the startup state 701. From the startup state 710, the positional therapy device state may transition to the docked state 707, the calibration state 702, or the low battery state 709 based on one or more of whether the positional therapy device is in the dock, startup processing has been completed, and the battery voltage.

The calibration state 702 represents a state in which the pointing angle/vector of the positional therapy device may be configured by the user (e.g., user 101). Calibration of the pointing angle/vector of the positional therapy device may include reading the current pointing vector of a positional sensor (e.g., positional sensor 220) of the positional therapy device responsive to user input and saving the calibrated pointing angle/vector as a rotational reference point to which subsequent pointing vectors of the positional sensor may be compared. According to one embodiment, completion of the calibration of the pointing angle/vector triggers the start of a sleep session. Calibration of the positional therapy device pointing angle/vector is described further below with reference to FIGS. 10A-B. From the calibration state 702, the positional therapy device state may transition to the docked state 707, the standby state 703, or the low battery state 709 based on one or more of whether the positional therapy device is in the dock, calibration processing has been completed, and the battery voltage.

The standby state 703 represents a normal waiting state in which the positional therapy device remains until the positional therapy device pointing angle/vector moves into the configured alert zone, or responsive to the positional therapy device being docked or the charge of the battery (e.g., rechargeable battery 265) being low. From the standby state 703, the positional therapy device state may transition to the docked state 707, the alarm state 704, or the low battery state 709 based on one or more of whether the positional therapy device is in the dock, whether the user's sleep position (e.g., head orientation) is within the alert zone, and the battery voltage.

The alarm state 704 may be responsible for generating an alarm set (e.g., a set of one or more user-configurable audible notifications), which may have a number of associated user-configurable attributes, for example, associated with a sleep profile. The user-configurable attributes may include, among others, a type of sound (e.g., a tone or a sampled sound), a start volume level, an end volume, a rate of repetition, and a number of times to repeat the alarm. Non-limiting examples of user-configured sleep profile attributes, including attributes of the alarm set, are described below with reference to FIG. 9. From the alarm state 704, the positional therapy device state may transition to the docked state 707, the snooze state 705, the squelch state 706, or the low battery state 709 based on one or more of whether the positional therapy device is in the dock, whether the user has snoozed the alarm, for example, via input to an application (e.g., app 131 or mobile app 310) associated with the positional therapy device or to the positional therapy device (e.g., a double tap), whether the alarm has timed out, and the battery voltage.

The snooze state 705 represents a state in which the user has snoozed the alarm set. The snooze state 705 may be responsible for delaying an amount of time indicated by an alert snooze time before transitioning back to the alarm state 704. According to one embodiment, the user may snooze the alarm set by issuing a snooze command to the positional therapy device. The snooze command may be issued via a user interface of the application or by tapping the positional therapy device, for example, a single finger tap or a sequence of two or more taps in rapid succession (e.g., a double tap).

The squelch state 706 represents a state in which the alarm set has timed out (e.g., after the user has been alerted for the user-configurable number of alerts). The squelch state 706 may be responsible for restarting the alerting process by returning to the alarm state upon expiration of a squelch timer. From the squelch state 706, the positional therapy device state may transition to the alarm state 704, the docked state 707, or the low battery state 709 based on one or more of whether the positional therapy device is in the dock, whether the squelch timer has expired, and the battery voltage.

The docked state 707 represents a state in which the positional therapy device is engaged with the dock. According to one embodiment, placing the positional therapy device in the dock represents the end of a sleep session. The docked state 707 may be responsible for reactivating a wireless connection, for example, via a wireless transmitter (e.g., wireless transmitter 270) with a mobile device (e.g., smartphone 130) running the application, initiating the transfer of time-series data (e.g., time-series data 511) to the application, and causing the application to perform post sleep session processing (e.g., prompting the user to answer a sleep session questionnaire, presenting a sleep session summary to the user, and storing the time-series data to the cloud). From the docked state 707, the positional therapy device state may transition to the charging state 708 or the calibration state 702 based on one or more of whether the positional therapy device is in the dock and whether the battery is fully charged.

The charging state 708 represents a state in which the positional therapy device is engaged with the dock and the battery is actively being recharged. From the charging state 708, the positional therapy device state may transition to the docked state 707 responsive to the positional therapy device being removed from the dock or responsive to the battery being fully charged.

The low battery state 709 represents a protective state in which the positional therapy device may be shut off to avoid damage to the battery. In the context of the present example, the positional therapy device may reboot to come out of the low battery state 709. For example, from the low battery state 708, the positional therapy device state may transition through the startup state 701 to the docked state 707, and then to the charging state 708 responsive to being placed in the dock.

While in the context of the state diagrams (e.g., FIGS. 6-7) described and illustrated herein a number of enumerated states are included, it is to be understood that examples may include additional states before, after, and/or in between the enumerated states. Similarly, in some examples, one or more of the enumerated states may be omitted and/or transition to different states.

Example Sleep Session Processing

Figure 8:
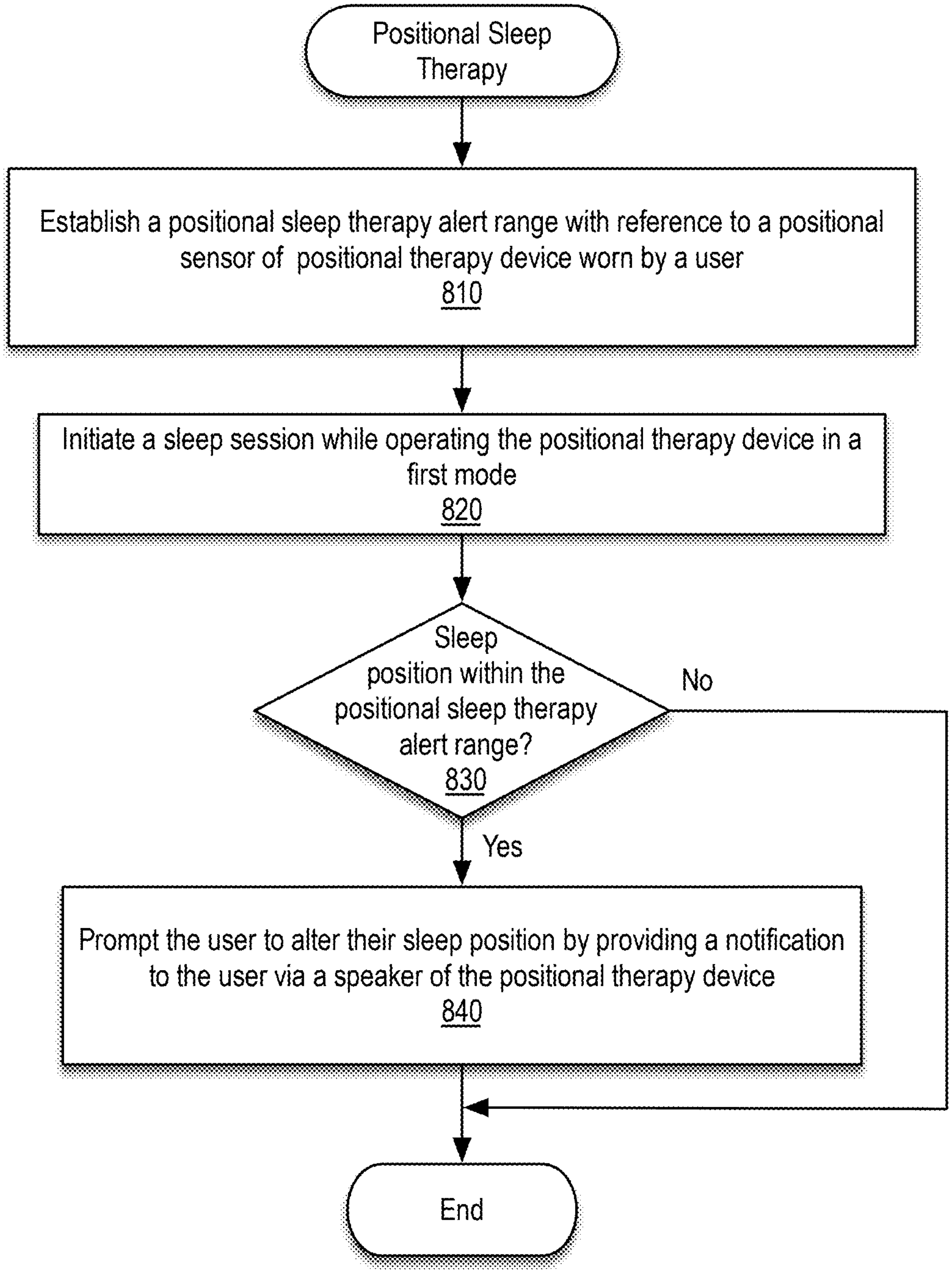
FIG. 8 is a high-level flow diagram illustrating operations for sleep session initialization and prompting a user when the user's sleep position is outside of a positional sleep therapy alert range in accordance with an embodiment of the present disclosure.

FIG. 8 is a high-level flow diagram illustrating operations for sleep session initialization and prompting a user when the user's sleep position is outside of a positional sleep therapy alert range in accordance with an embodiment of the present disclosure. The processing described with reference to FIG. 8 may be performed by a positional therapy device (e.g., positional therapy device 110 or 200) worn by the user (e.g., user 101) in their ear during a sleep session or on their head via integration with a PAP mask or straps. A non-limiting example of how a positional therapy device or system may be integrated with a PAP mask system (e.g., directly sewn, affixed to, bound/strapped to, and/or molded into the PAP strap material and/or its components) is described below with reference to FIG. 23B.

At block 810, a positional sleep therapy alert range is established with reference to a positional sensor (e.g., positional sensor 220) of the positional therapy device. The positional therapy device may be operable in one or more modes. For example, as described above, the positional therapy device may include a notification (or therapeutic) mode and a logging (or diagnostic) mode. According to one embodiment, the positional sleep therapy alert range may be established during a calibration state (e.g., calibration state 702) of the positional therapy device. With the positional therapy device seated within the user's ear or with the positional therapy device integrated with a PAP mask and/or straps and placed on the user's head, the user may assume a particular position with their head resting on a pillow and issue a calibration command to the positional therapy device, for example, via input to an application (e.g., app 131 or mobile app 310) associated with the positional therapy device or to the positional therapy device (e.g., in the form of a single finger tap or a sequence of two or more taps in rapid succession). The calibration may define a pointing angle of the positional therapy device based on the current X, Y, and Z orientation of the positional therapy device in 3D space as indicated by the positional sensor of the positional therapy device, thereby establishing a known frame of reference for the orientation of the positional therapy device. An example of computations relating to establishment of a rotational frame of reference is provided below. The positional sleep therapy alert range or zone may then be defined with reference to the calibrated pointing angle and one or more predetermined or configurable offset angles. A non-limiting example of calibration of the positional therapy device and establishment of the positional sleep therapy alert zone is described further below with reference to FIGS. 10A-B.

At block 820, a sleep session is initiated while operating the positional therapy device in a first mode (e.g., the notification mode). The sleep session may be initiated automatically responsive to completion of the calibration of block 810 or may be initiated responsive to a further command from the user, for example, indirectly to the positional therapy device via a user interface of the application (e.g., a start sleep session button) or directly to the positional therapy device (e.g., via a tap or two or more taps in rapid succession). According to one embodiment, initiation of the sleep session causes the positional therapy device to deactivate a wireless transmitter (e.g., wireless transmitter 270) of the positional therapy device and initiate a monitoring cycle involving performing repeated measurements over time of the positional sensor and one or more optional sensors (e.g., an oximeter, a pulse oximeter, a temperature sensor, a microphone, etc.) associated with the positional therapy device. For example, initiation of the sleep session may cause the positional therapy device to start the observe, decide, act flow as described above with reference to FIG. 6.

At decision block 830, a determination may be made regarding whether the current sleep position of the user is within the positional sleep therapy alert range established in block 810. If so, processing continues with block 840. This determination may be made by measuring the current pointing angle/vector as provided by the positional sensor, comparing that pointing angle/vector against the configured reference pointing angle/vector as provided in the calibration state, and then computing if the current pointing angle/vector falls within the configured alert zone. Through that computation both the zAngle (1524 of FIG. 15—The angle between the current pointing angle/vector and the reference pointing angle/vector) is measured as well as the orientation of the positional therapy device and user's head within the rotational frame of reference. From that orientation, both the zPitch (1525 of FIG. 15) and zRoll (1526 of FIG. 15) are calculated with respect to the rotational frame of reference. An example of computing zAngle is provided below.

At block 840, the user is prompted to alter their sleep position by providing an audible notification to the user via a speaker (e.g., speaker 275) of the positional therapy device that is proximate to or within an auditory canal of the user's ear. The audible notification can consist of various recorded (sampled) and/or synthesized sounds (e.g. voice instructions, animal and environmental sounds, beeps, and/or tones) and may be part of an alert set including a number of user-configurable attributes defining, among other things, a type of sound (e.g., a tone or a sampled sound), a start volume level, an end volume, a rate of repetition, and a number of times to repeat the alarm. Non-limiting examples of user-configured sleep profile attributes, including attributes of the alarm set, are described below with reference to FIG. 9.

While for sake of brevity, in the context of the present example, only a single evaluation of the sleep position against the positional sleep therapy alert range is described, it is to be appreciated the sleep session monitoring may be periodically performed until a command is received from the user indicating the sleep session is complete, for example, by placing the positional therapy device in the dock. For example, following block 840, processing may loop back to decision block 830 and the no branch of decision block 830 may loop back to decision block 830 after a delay and/or other intermediate processing (e.g., evaluation of alert set attributes, evaluation of sleep session end conditions, etc.). Further details regarding initiation of a sleep session and ending a sleep session are described below with reference to FIGS. 11 and 12.

While in the context of the present example, the wireless transmitter is described as being deactivated during a sleep session, it is to be appreciated, in an embodiment in which sleep session processing is distributed between the positional therapy device and the application, the wireless transmitter may remain active. For example, in an implementation or mode in which the application is involved in the alerting process, the wireless transmitter may remain active and the positional therapy device may stream position data received from the positional sensor to the application via the wireless transmitter and may receive commands (e.g., issue alarm, stop alarm, etc.) from the application via the wireless connection with the mobile device.

Example User-Configured Sleep Profile Attributes

FIG. 9 is a table 900 illustrating user-configured sleep profile attributes in accordance with an embodiment of the present disclosure. Table 900 includes a name column 910, a related configuration column 920, and a description column 930. The name column 910 indicates a name (e.g., Alert Hold Off) of a given user-configured sleep profile attribute, whereas the related configuration column 920 identifies the one or more corresponding internal configuration parameters (e.g., alertHoldffCount) that may be set based on the given user-configured sleep profile attribute. The various user-configured sleep profile attributes may initially be assigned default values.

The user (e.g., user 101) may customize their sleep experience by adjusting one or more of the user-configured sleep profile attributes over time via an application (e.g., app 131 or mobile app 310) associated with the positional therapy device (e.g., positional therapy device 110 or 200). For example, if the user is a deep sleeper or a light sleeper, they may wish to experiment with various combinations of Start Volume, End Volume, Alert Ramp, and Tone or Sample to see what values of these attributes work best for them. As another example, if the user does not wish to receive an immediate alert responsive to a (temporary) change in sleeping position that puts them within the alert zone, they may wish to set a longer Alert Hold Off value. As yet another example, if the user has difficulty promptly changing their sleeping position (e.g., due to weight, injury, or some other issue), they may wish to set a longer Alert Delays value to provide sufficient time to adjust their sleeping position before receiving another alarm.

According to one embodiment, the current configured set of values for the sleep profile attributes may be saved in the user's profile to facilitate reuse of sleep profile attribute values which the user finds satisfactory. In one embodiment, cloud services (e.g., cloud services 140 or 400) may evaluate input received from the user on a sleep questionnaire and provide recommendations to help the user achieve more restful sleep. Some of these recommendations may include one or more suggestions for adjusting one or more values of the sleep profile attributes. For example, if a recommendation engine (e.g., business logic and recommendation engine 430) determines based on its analysis of the time-series data (e.g., stored in time-series database 450) that the user is not responding well (e.g., the alerts are timing out more often than not and the user is not adjusting their sleep position responsive to the alerts) to audible notifications delivered in accordance with the current sleep profile attributes, the recommendation engine may suggest increasing one or more of the Start Volume, End Volume, and Alert Ramp or may suggest changing from Tone to Sample or vice versa.

Figure 10A:
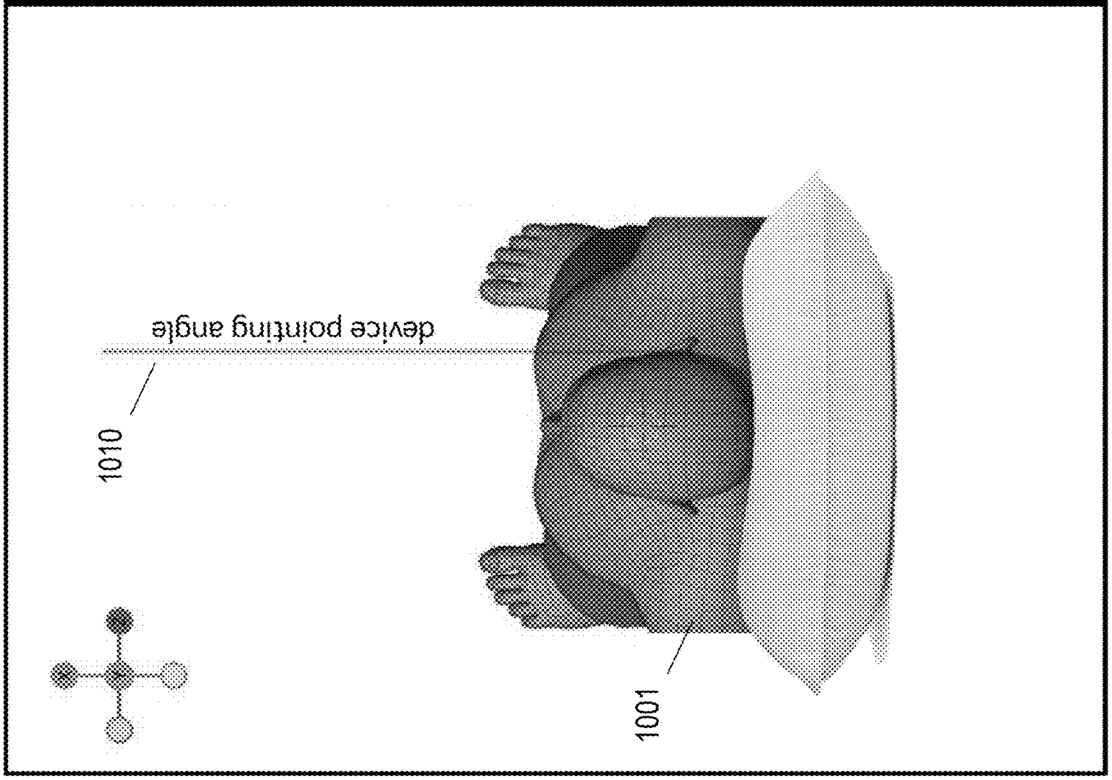
FIGS. 10A-B illustrate calibration of a positional therapy device and establishment of a positional sleep therapy alert zone in accordance with an embodiment of the present disclosure.
Figure 10B:
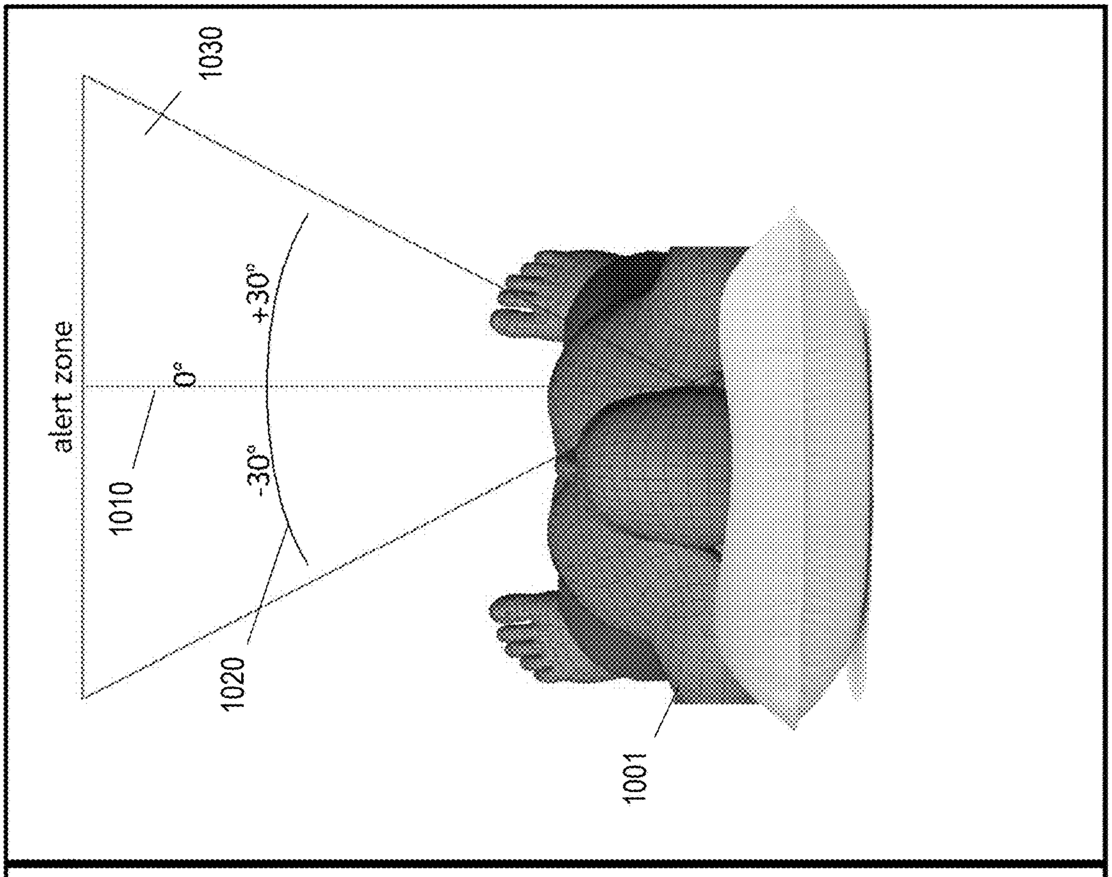

Example Positional Therapy Device Pointing Angle Calibration and Alert Zone Monitoring FIGS. 10A-B illustrate calibration of a positional therapy device and establishment of a positional sleep therapy alert zone in accordance with an embodiment of the present disclosure. Because the position of a PAP mask system with which the positional therapy device (e.g., positional therapy device 110 or 200) may from sleep session to sleep session, in one embodiment, prior to each sleep session, a user (e.g., user 1001, which may be analogous to user 101) may be prompted through an application (e.g., app 131 or mobile app 310) associated with the positional therapy device to calibrate a device pointing angle 1010 for the positional therapy device that may be read from a positional sensor (e.g., positional sensor 220) of the positional therapy device. The calibrated device pointing angle 1010 may be used as a relative frame of reference for the orientation of the positional therapy device in 3D space (or a rotational reference point) that may be subsequently used during a given sleep session as a point of comparison to sleep positions the user may find themselves in during the given sleep session.

In FIGS. 10A-B, the user 1001 is shown lying on his back and wearing a PAP mask system (not shown) with the positional therapy device (not shown) near his right ear. While somewhat arbitrary, for purposes of explanation in various examples described herein, the X axis refers to a vertical axis passing through a positional sensor of the positional therapy device, for example, parallel to a vertical line running between the user's nose and the posterior of the user's cranium, the Y axis refers to an axis passing through the positional sensor that is parallel to a line extending from the top of the user's skull to the user's neck, and the Z axis refers to a horizontal axis passing through the positional sensor side to side—in this example, from one ear to the other. In this example, while lying on his back, the user has calibrated the device pointing angle 1010, to a zero degree angle from the X axis. While the device pointing angle 1010 may include an X component, a Y component, and a Z component, only the X component is shown in this example.

In one embodiment, calibrating the device pointing angle 1010 for a given sleep session also establishes an alert zone 1030 (which may also be referred to herein as a positional therapy sleep range or zone), for example based on a tare vector (e.g., tare X 1514, tare Y 1515, and tare Z 1516 of FIG. 15). The tare vector may be calculated by adding one or more predefined or configurable offset angles (e.g., alert angle 1612 of FIG. 16) to the calibrated device pointing angle 1010. In the present example, the offset angle 1020 used for both X and Y is 30 degrees and the alert zone 1030 is defined by inclusion of the calibrated device pointing angle 1010 within the alert zone 1030. In some embodiments, the alert zone may instead be defined to be the inverse of that shown in FIG. 10B, in which the (inverted) alert zone is defined by exclusion of the calibrated device pointing angle 1010 from the alert zone. In one embodiment, the alert zone 1030 remains fixed throughout the given sleep session, unless reconfigured by the user 1001.

Figures 10C, 10D:
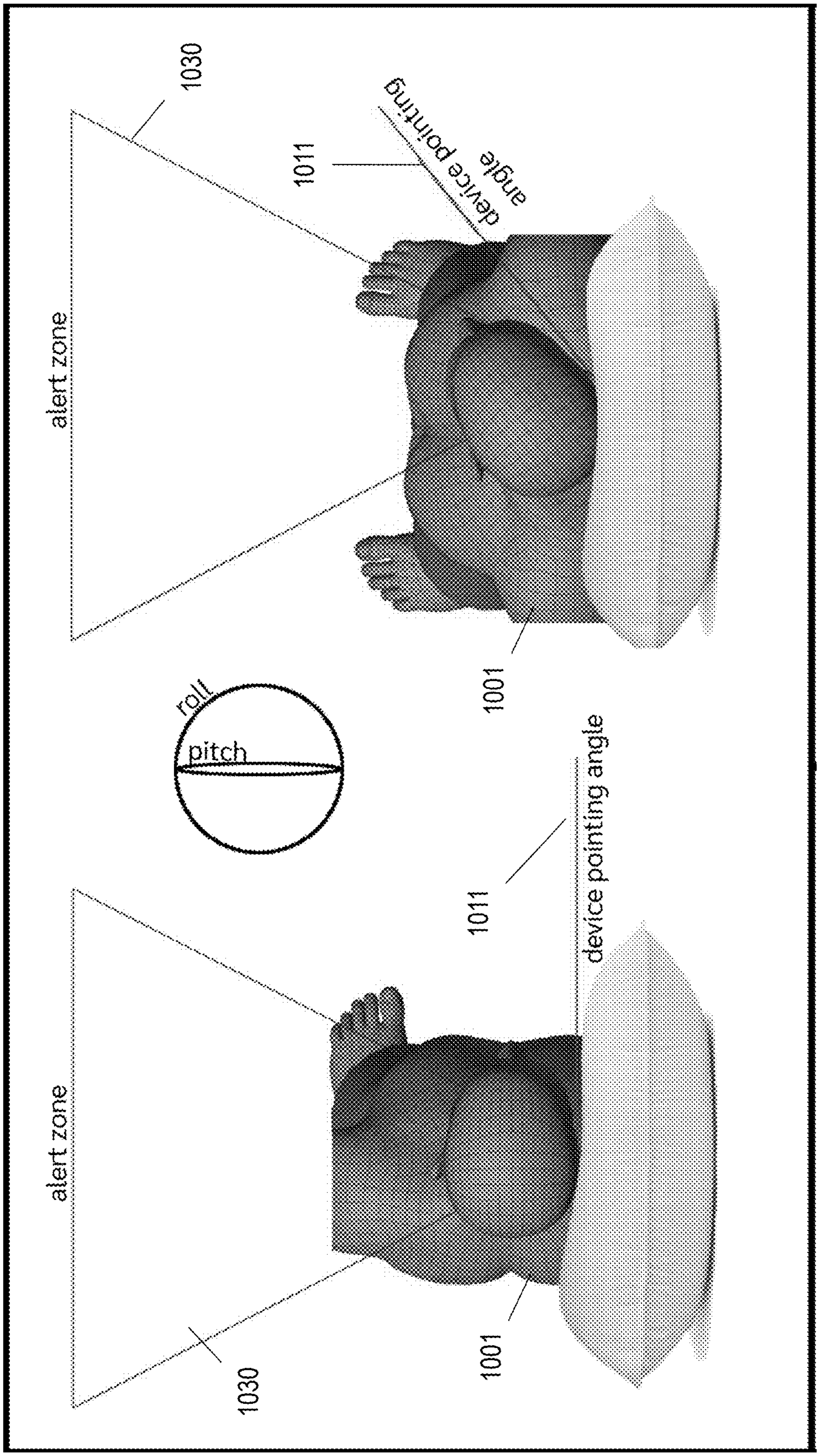
FIGS. 10C-D illustrate a head orientation of the user in which the current device pointing angle of the positional therapy device is outside of the established positional sleep therapy alert zone in accordance with an embodiment of the present disclosure.

FIGS. 10C-D illustrate a head orientation of the user 1001 in which the current device pointing angle 1011 of the positional therapy device is outside of the established positional sleep therapy alert zone 1030 in accordance with an embodiment of the present disclosure. FIGS. 10C-D illustrate how the rolling and pitching of the head or body angles of the user 1011 change the positional therapy device orientation and thus the current device pointing angle 1011. The orientation of the user's head may be represented in the form of roll (rotation about a front-to-back axis perpendicular to the drawing page, for example, the Y axis), pitch (rotation about a side-to-side axis, for example, the Z axis), and yaw (rotation about the vertical axis, for example, the X axis). While sleeping, the user's head may move or rotate in three dimensions: yaw, head tilted left or right (e.g., ear toward or away from the shoulder); pitch, chin up and forehead down or chin down and forehead up; and roll, nose turned to the left or right. In one embodiment, roll, pitch, and yaw are measured relative to an established frame of reference represented by the calibrated zero-point position (e.g., the center of the alert zone 1030) based on a current absolute pointing angle (e.g., X 1511, Y 1512, and Z 1513 of FIG. 15) read from the positional sensor.

Continuing with the example started with reference to FIG. 10A, in FIG. 10C, it is assumed the user 1001 is now positioned on his side at this point in time during the sleep session. As can be seen, the current device pointing angle 1011 is not within the alert zone 1030. Therefore, no prompting of the user 1001 via an audible notification to alter their sleep position is warranted and no such prompting is performed. Similarly, in FIG. 10D, although the user 1011 is positioned on his back at this point in time during the sleep session, because the current device pointing angle 1011 is again not within the alert zone 1030, no prompting of the user 1001 via an audible notification is warranted and no such prompting is performed.

Figure 10E:
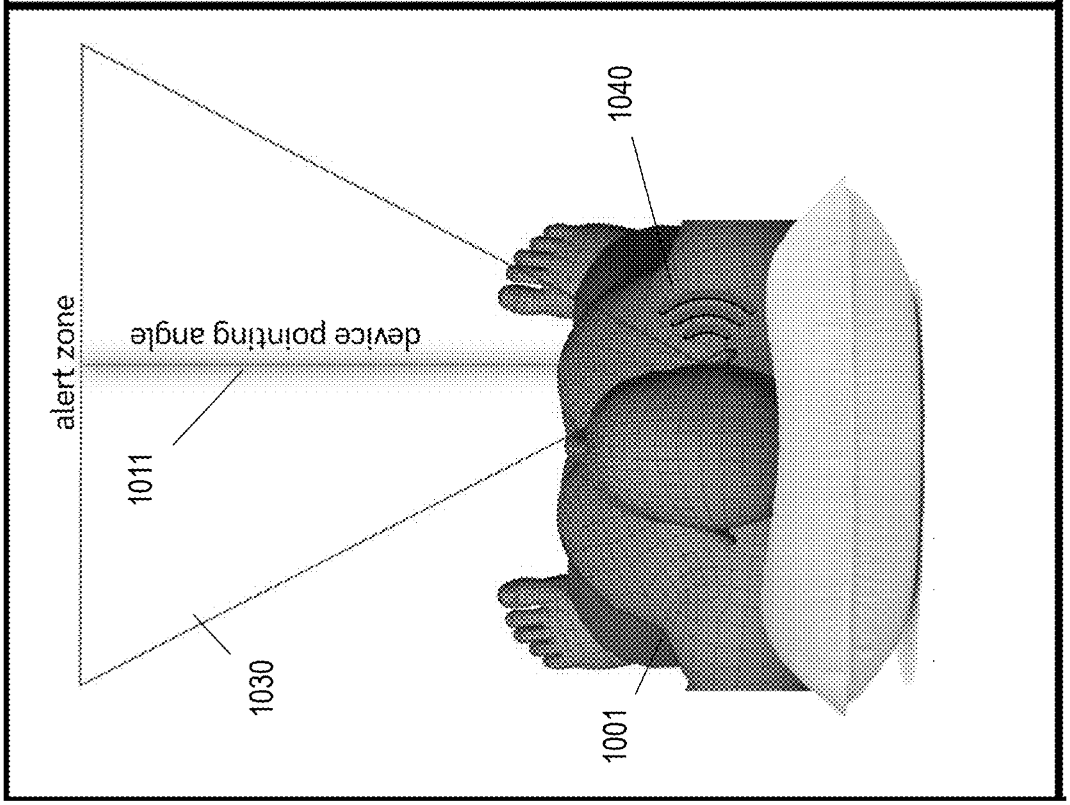
FIGS. 10E-F illustrate a head orientation of the user in which the current device pointing angle of the positional therapy device is within the established positional sleep therapy alert zone in accordance with an embodiment of the present disclosure.
Figure 10F:
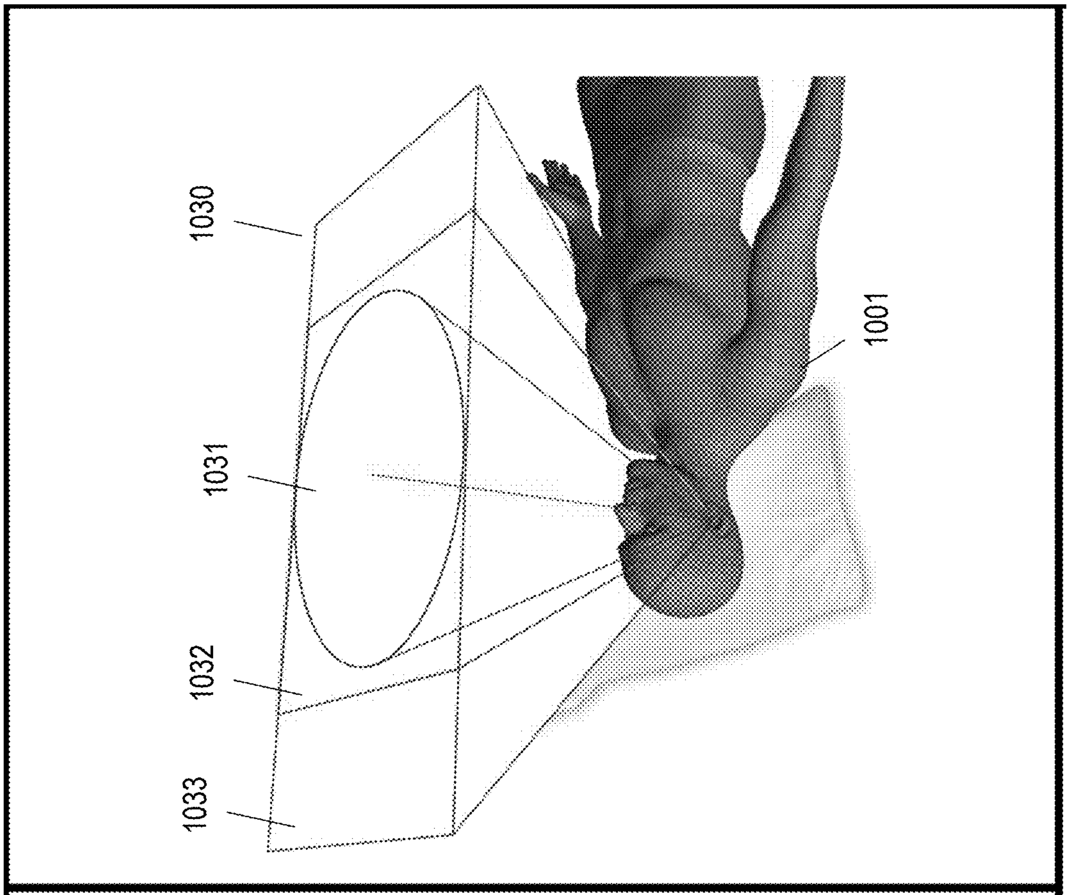

FIGS. 10E-F illustrate a head orientation of the user in which the current device pointing angle 1011 of the positional therapy device is within the established positional sleep therapy alert zone 1030 in accordance with an embodiment of the present disclosure. Continuing with the example started with reference to FIG. 10A, in FIGS. 10E-F, it is assumed the user 1001 is again positioned on his back at this particular point in time during the sleep session. As can be seen, the current device pointing angle 1011 is now within the middle of the alert zone 1030. Therefore, delivery of an audible notification 1040 to the user 1001 via a speaker (e.g., speaker 275) to prompt the user 1001 to alter their sleep position is performed in this scenario.

As depicted in FIG. 10F, the alert zone 1030 may be calculated to various shapes (e.g., a conical shape 1031, a square pyramid 1032, and a rectangular pyramid 1033).

Example Identification/Notification of Potential Sleep Respiratory Issue

Figure 11:
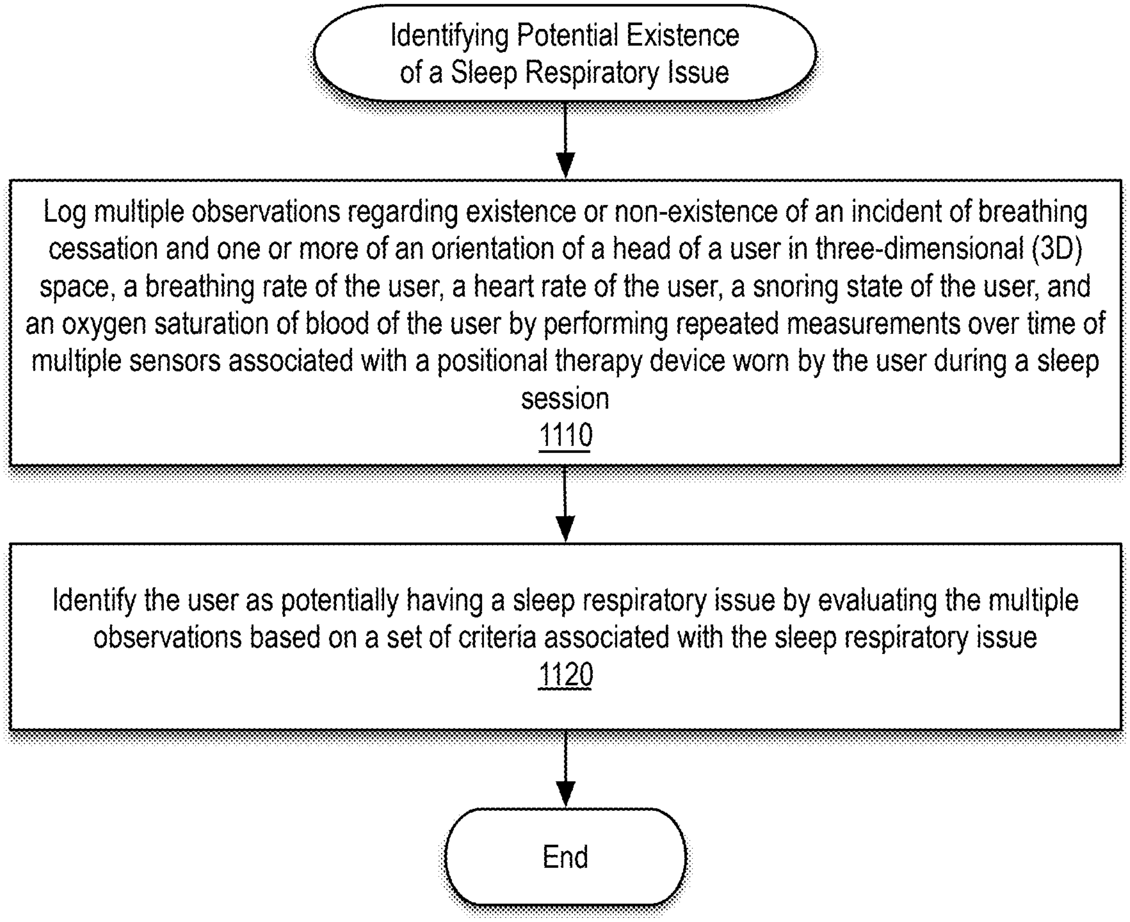
FIG. 11 is a high-level flow diagram illustrating operations for identifying a user as potentially having a sleep respiratory issue in accordance with an embodiment of the present disclosure.

FIG. 11 is a high-level flow diagram illustrating operations for identifying a user as potentially having a sleep respiratory issue in accordance with an embodiment of the present disclosure. The processing described with reference to FIG. 11 may be performed by a system (e.g., system 100) including (i) a positional therapy device (e.g., positional therapy device 110 or 200) worn by the user (e.g., user 101) (e.g., in their ear or on their head as part of a PAP mask or straps) during a sleep session and (ii) one or both of an associated application (e.g., app 131 or mobile app 310) and cloud services (e.g., cloud services 140 or 400). In one embodiment, the positional therapy device may be operating in either a logging mode or a notification mode (with logging, for example, of time-series data (e.g., time-series data 511) enabled). Types of data that may be captured for report generation and/or export to facilitate diagnosis of various sleep respiratory issues by a medical professional are listed in FIG. 23. These same types of data may be analyzed by the application and/or the cloud services to infer the user has an unspecified sleep respiratory issue or a particular sleep respiratory issue when the data is sufficient to allow more specificity.

At block 1110, multiple observations regarding existence or non-existence of an incident of breathing cessation and one or more of an orientation of a head of the user, a heart rate of the user, a snoring state of the user, a body temperature of the user, and an oxygen saturation of blood of the user are logged by performing repeated measurements over time of multiple sensors associated with the positional therapy device. According to one embodiment, the multiple sensors may include one or more of a positional sensor (e.g., positional sensor 220), an oximeter, a pulse oximeter (e.g., pulse oximeter 121), a microphone (e.g., microphone 215), and a temperature sensor (e.g., temperature sensor 210). In one embodiment, the sampling of the multiple sensors may be performed by one or more application tasks (e.g., application tasks 530) running within an RTOS (e.g., RTOS 550) of the positional therapy device. Depending upon the particular implementation, the logging may be performed local to the positional therapy device, for example, using one or both of a shared memory (e.g., shared memory 510) and flash storage (e.g., flash storage 520) during the sleep session and then the log (e.g., time-series data 511) may be subsequently transmitted to the associated application after completion of the sleep session or the observations may be streamed in real time or near real time to the application, which in turn performs the logging locally or to the cloud.

At block 1120, the user may be identified as potentially having a sleep respiratory issue by evaluating the multiple observations based on a set of criteria associated with the sleep respiratory issue. For example, the associated application may advise the user they should consult with a sleep or respiratory professional for potential existence of a sleep respiratory issue or otherwise notify them regarding observed symptoms indicative of the potential existence of a sleep respiratory issue.

In some embodiments, the evaluation of the multiple observations may be sufficient to provide the user with a more specific notification specifically identifying the potential sleep respiratory issue as one or more of snoring, positional snoring, positional UARS, SA, or PSA. As will be appreciated, advice provided by the application or cloud services to consult with a medical professional regarding an unspecified sleep respiratory issue or a specifically identified sleep respiratory issue that appears most likely based on analysis of the sleep data does not represent medical advice or constitute a medical diagnosis of a particular condition. Rather, it is simply suggested here that based on the differences in symptoms among the various sleep respiratory issues, certain symptoms observed in the data captured by the positional therapy device may facilitate distinguishing one potential sleep respiratory issue from the others and potentially informing the user of reasonable inferences that can be made given the available data. For example, when the number of observed incidents of breathing cessation exceed an SA threshold during a sleep session, it is more likely the user has some form of sleep apnea (e.g., central sleep apnea or OSA) than simply a snoring issue or UARS. When the number of observed incidents of breathing cessation exceed the SA threshold and there is a correlation between the observed incidents of breathing cessation and a particular sleep position (e.g., an orientation of the head of the user that is indicative of the user sleeping on their back in a nose-toward-the-ceiling orientation) or the majority of observed incidents of breathing cessation otherwise appear to be attributed to the orientation of the head of the user, then it may be inferred the user's SA is positional in nature and the user has PSA. When there are fewer incidents of breathing cessation (e.g., less than the SA threshold) and the user's oxygen saturation remains at or above an oxygen saturation threshold then it may be inferred the user more likely has UARS than some form of sleep apnea. When none of the above criteria are met but snoring sounds are identified during the sleep session, the user may be notified of the potential existence of a snoring issue. As with the other sleep respiratory issues, when there is a correlation of the incidence or non-incidence of snoring with particular sleep positions, then the snoring issue may be considered positional snoring.

Example Initiation of a Sleep Session

Figure 12:
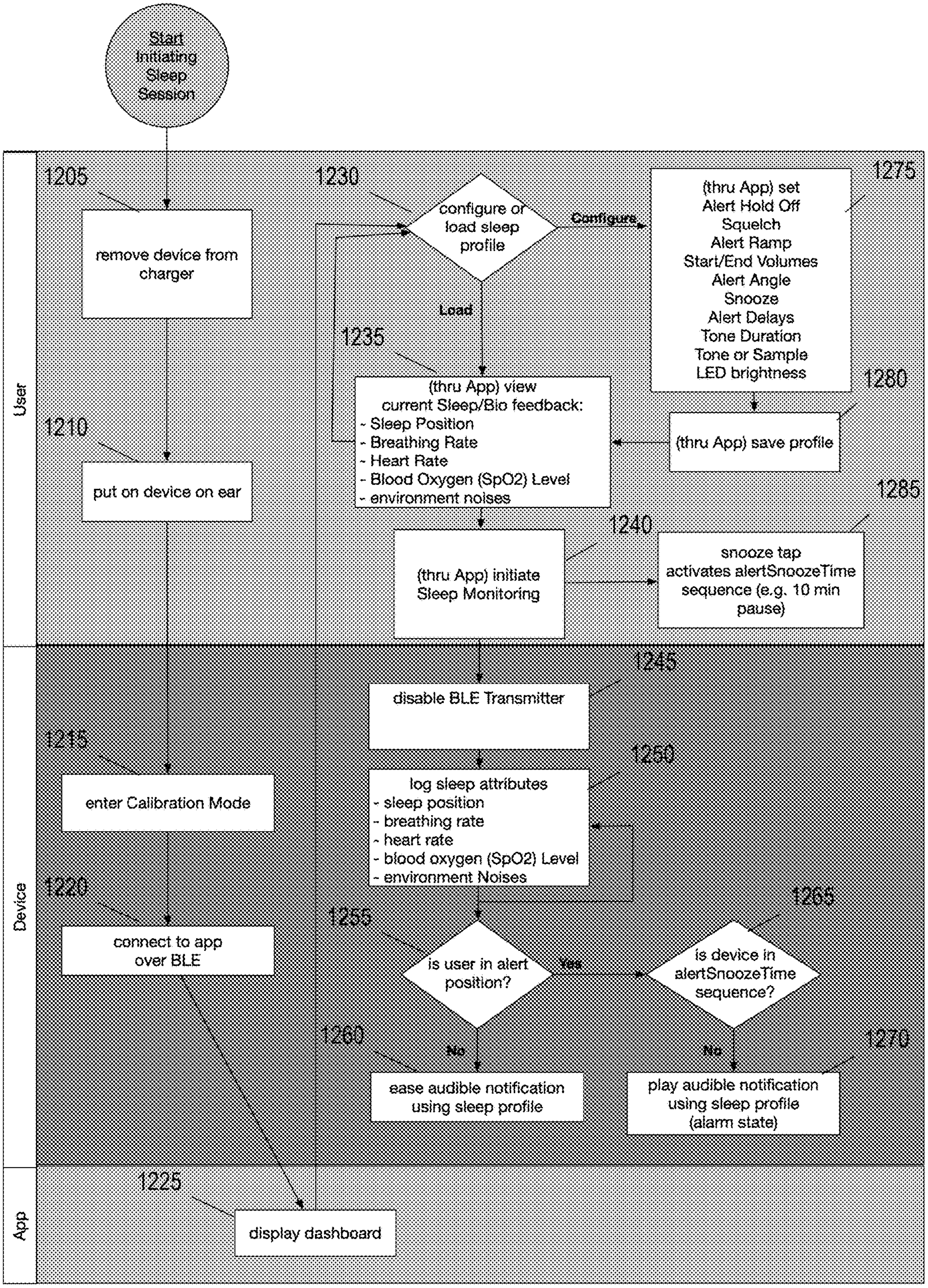
FIG. 12 is a flow diagram illustrating operations for initiating a sleep session in accordance with an embodiment of the present disclosure.

FIG. 12 is a flow diagram illustrating operations for initiating a sleep session in accordance with an embodiment of the present disclosure. In the context of FIG. 12, activities and/or processing performed by a user (e.g., user 101 or 1001), a positional therapy device (e.g., positional therapy device 110 or 200), and an application (e.g., app 131 or mobile app 310) associated with the positional therapy device are shown in an upper portion, a middle portion, and a lower portion of the figure, respectively.

At block 1205, the user removes the device from the charger (e.g., a dock).

At block 1210, the user puts the PAP mask or straps having the positional therapy device integrated therein on their head. According to one embodiment, when the PAP mask system is worn by the user, audible notifications created by a speaker (e.g., speaker 275) may be transmitted or transferred to the user's ear.

At block 1215, the positional therapy device enters into a calibration mode (e.g., calibration state 702). Entry into the calibration mode may be triggered by removal of the positional therapy device from the charger, responsive to automatic ear detection, and/or input by the user via tap(s) or via a user interface of the application. Examples of calibration of the pointing angle of the positional therapy device are described above with reference to FIG. 7 (e.g., calibration state 702) and FIGS. 10A-B.

At block 1220, the positional therapy device connects to the application via a wireless connection (e.g., BLE) between the positional therapy device and a mobile device (e.g., smartphone 130) on which the application is running.

At block 1225, the application displays a dashboard of the application. The dashboard may allow the user to view, among other things, information regarding the last sleep session score and a summary of the last sleep session. The user may also be provided with an opportunity to test and/or adjust the current sleep profile (e.g., the user-configured sleep profile attributes described above with reference to FIG. 9) before beginning a new sleep session. The dashboard may also include an "initiate sleep" button to allow the user to start a sleep session (e.g., start sleep monitoring) immediately or after a predetermined or configurable amount of time.

At decision block 1230, the user may configure a new sleep profile or load a saved sleep profile. The saved sleep profiles can come from a previously user-saved sleep profile or a premade profile from the manufacturer. The premade sleep profiles could be designed to work best for specific sleep conditions (e.g. a light sleeper that snores, or a heavy sleeper with obstructive sleep apnea). A default profile could be preloaded by the manufacturer so the positional therapy device will function in its default state. If the user selects loading of a saved sleep profile, sleep session initiation processing continues with block 1235. If the user selects configuration of a new sleep profile, sleep session initiation processing continues with block 1275.

At block 1235, the user may be presented through the application with real time feedback regarding sensor data available from the positional therapy device, including one or more of the current sleep position, the current breathing rate, the current heart rate, the current blood oxygen (SpO2) level, and existence or non-existence of environmental noises currently observed by the positional therapy device. From block 1235, the user may return to decision block 1230 or continue to block 1240.

At block 1275, the user may configure a new sleep profile for the anticipated sleep session via the application, including setting one or more of alert hold off, squelch, alert ramp, start/end volume, alert angle, snooze, alert delays, tone duration, tone or sample, and LED brightness.

At block 1280, the user may save the new sleep profile configured in block 1275.

At block 1240, the user may initiate sleep monitoring through the application. For example, the user may select the "initiate sleep" button.

At block 1285, at any time during the sleep session the user may perform a snooze tap (e.g., a finger tap or a series of two or more taps in rapid succession) on the housing of the positional therapy device to activate an alert snooze time sequence, for example, pausing the issuance of alerts or audible notifications by the positional therapy device for a configured time period (e.g., 10 minutes).

At block 1245, the wireless transmitter (e.g., wireless transmitter 270) may be disabled.

At block 1250, sleep attributes are logged. For example, every 3 to 5 seconds and/or responsive to detection of movement or sound, sensor measurements indicative of, among other things, one or more of sleep position, for example, in the form of a current pointing angle/vector of a position sensor), breathing rate, heart rate, blood oxygen (SpO2) level, and environment noise may be logged. According to one embodiment, the user's breathing rate and/or heart rate may be determined by analyzing movements of the positioning sensor and/or by analyzing breathing and/or heart sounds received through a microphone (e.g., microphone 215) as described further below with reference to FIGS. 17-21.

According to one embodiment, the sleep attributes are logged within a memory of the positional therapy device in the form of time-series data (e.g., time-series data 511). A non-limiting example, of various types of data that may be logged as part of the time-series data for a given sleep session is described below with reference to FIG. 15. As described further below, the capturing of time-series data during sleep sessions and the ability to selectively export such data (from the application and/or from cloud services (e.g., cloud services 140 or 400)) for a single sleep session or a set of sleep sessions facilitates the ability of a medical professional to make a diagnosis of the user as having a sleep respiratory issue. The exported data may be in the form of a report, a summary, and/or raw data.

At decision block 1255, a determination may be made regarding whether the user is in an alert position. For example, as new data is logged, the sleep position of the user (as indicated by a pointing angle/vector of the positional therapy device) may be compared to a configured alert zone (e.g., alert zone 1030). If the user is in a sleep position representing an alert position, processing branches to decision block 1265; otherwise, processing continues with block 1260.

At decision block 1265, it is determined whether the positional therapy device is in an alert snooze time sequence. If not, the positional therapy device enters into an alert mode (e.g., alert state 704) and an audible notification is played to the user via the speaker in accordance with the active sleep profile. If so, such audible notifications are inhibited and no audible notification is provided to the user.

At block 1260, to the extent an audible notification is in process the sound may be gradually faded until stopped in accordance with the active sleep profile.

While for sake of brevity, in the context of the present example, only a single evaluation of whether the user is in an alert position is described, it is to be appreciated the sleep session monitoring may be periodically performed until a command is received from the user indicating the sleep session is complete, for example, by placing the positional therapy device in the dock. For example, following blocks 1260 and 1270, processing may loop back to block 1250 to continue logging and evaluation of whether the user is in an alert position.

Example Ending of a Sleep Session

Figure 13:
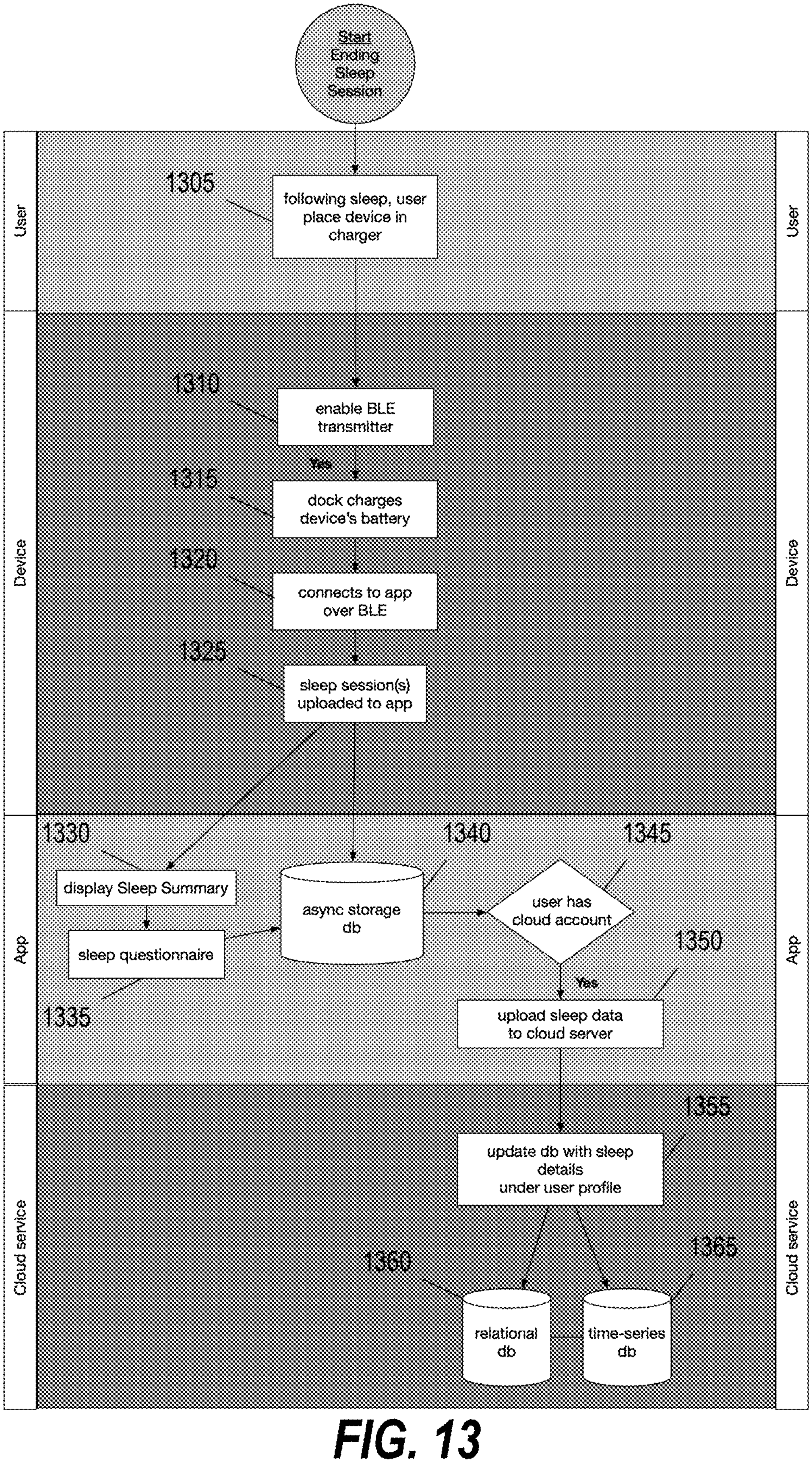
FIG. 13 is a flow diagram illustrating operations for ending a sleep session in accordance with an embodiment of the present disclosure.

FIG. 13 is a flow diagram illustrating operations for ending a sleep session in accordance with an embodiment of the present disclosure. In the context of FIG. 13, activities and/or processing performed by a user (e.g., user 101 or 1001), a positional therapy device (e.g., positional therapy device 110 or 200), an application (e.g., app 131 or mobile app 310) associated with the positional therapy device, and cloud services (e.g., cloud services 140 or 400) are shown in a top portion, an upper middle portion, a lower middle portion, and a bottom portion of the figure, respectively. In the context of the present example, it is assumed prior to block 1305, the positional therapy device was performing sleep monitoring as part of a current sleep session, for example, as described above with reference to FIG. 12.

At block 1305, the user may place the positional therapy device in the charger (e.g., a dock) to end the current sleep session.

At block 1310, the wireless transmitter (e.g., wireless transmitter 270) may be enabled.

At block 1315, the positional therapy device may enter into a docked mode (e.g., docked state 707) and commence charging of a battery (e.g., rechargeable battery 265) of the positional therapy device as appropriate (e.g., if it is not fully charged).

At block 1320, the positional therapy device connects to the application via a wireless connection (e.g., BLE) between the positional therapy device and a mobile device (e.g., smartphone 130) on which the application is running.

At block 1325, the sleep attributes logged by the positional therapy device, for example, in the form of time-series data (e.g., time-series data 511) for one or more sleep sessions may be uploaded to the application. The logged data for the one or more sleep sessions may be stored by the application within an asynchronous storage database 1340 (which may be analogous to asynchronous storage database 380).

At block 1330, a sleep summary is displayed to the user via the application.

At block 1335, the user is prompted to complete a sleep questionnaire. The sleep questionnaire may prompt for information relating to how the user feels and various sleep influencers (e.g., time of last meal, whether the user consumed alcohol and/or caffeine, occurrences of night disturbances, recent exercise, etc.). Answers to the sleep questionnaire may also be stored to the asynchronous storage database 1340 and linked to the recently ended sleep session.

At decision block 1345, it is determined whether the user has a cloud account associated with the positional therapy device. If so, processing continues with block 1350 where the sleep data from the asynchronous storage database 1340 is uploaded to the cloud account for accessibility via and by cloud services (e.g., cloud services 140 or 400). Otherwise, the user may be prompted to sign up for a cloud account.

At block 1355, databases (e.g., a relational database 1360, which may be analogous to relational database 440 and a time-series database 1365, which may be analogous to time-series database 450) are updated as appropriate to add the received sleep data for the user under the user's profile.

Example Functions Available at Anytime

Figure 14:
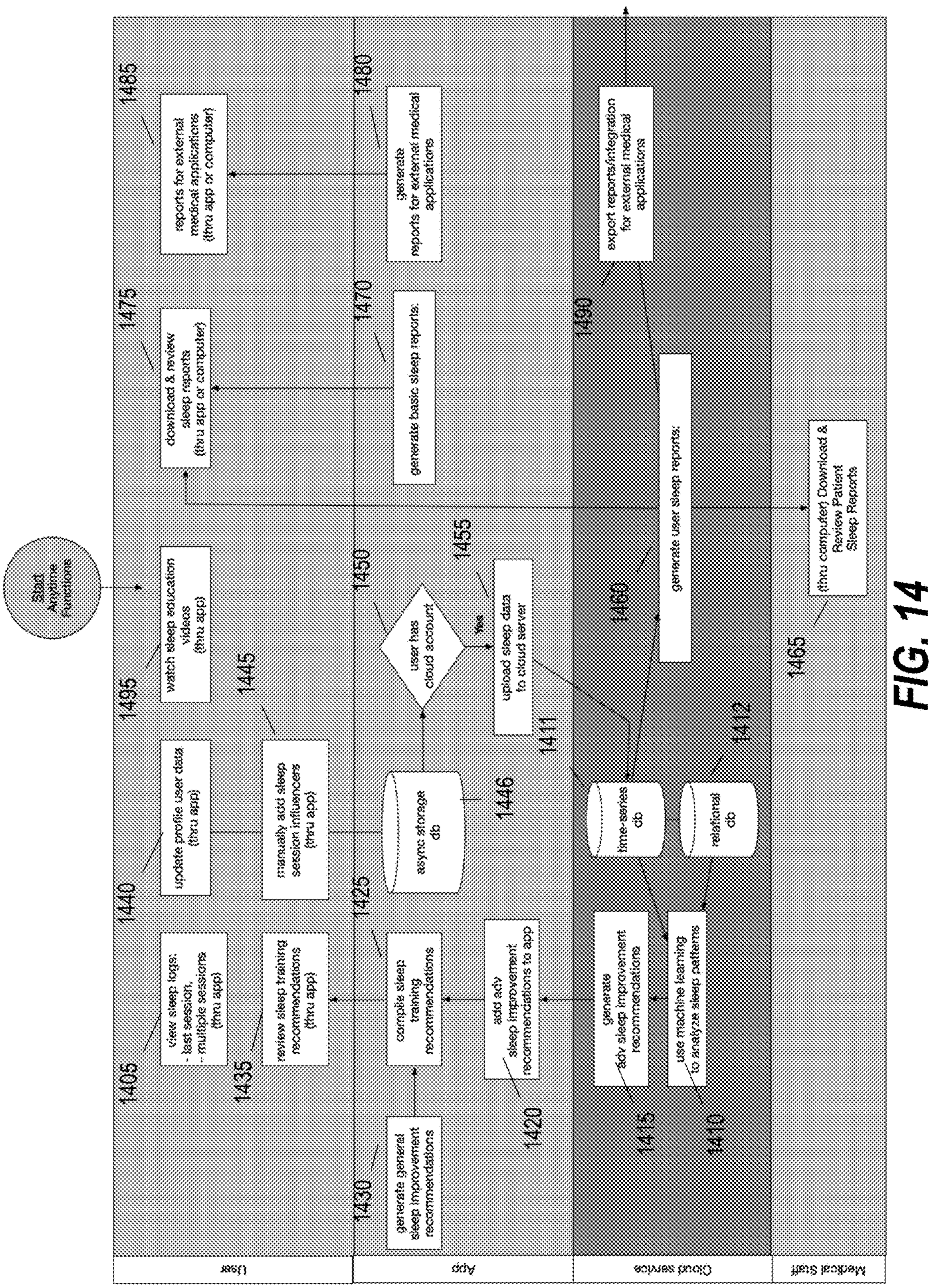
FIG. 14 is a flow diagram illustrating operations for accessing various functions outside of the context of a sleep session in accordance with an embodiment of the present disclosure.

FIG. 14 is a flow diagram illustrating operations for accessing various functions that may be available at any time in accordance with an embodiment of the present disclosure. In the context of FIG. 14, activities and/or processing performed by a user (e.g., user 101 or 1001), an application (e.g., app 131 or mobile app 310) associated with the positional therapy device (e.g., positional therapy device 110 or 200), cloud services (e.g., cloud services 140 or 400), and medical staff are shown in an upper portion, a middle portion, and a lower portion of the figure, respectively.

At block 1405, through the application, the user may view sleep logs (e.g., a sleep log for the last sleep session or sleep logs for multiple sessions).

At block 1410, ML techniques may be applied to analyze sleep patterns for the user based on sleep data retrieved from databases (e.g., a relational database 1412, which may be analogous to relational database 440 and/or 1360 and a time-series database 1411, which may be analogous to time-series database 450 and/or 1365). The data analyzed may include answers associated with sleep questionnaires, logged sleep attributes for a number of sleep sessions, device parameters established by the user, and/or past or current sleep profiles. In some embodiments, data from multiple users of a community of users of positional therapy devices may be analyzed.

At block 1415, advanced sleep improvement recommendations (e.g., adjust one or more sleep profile attribute values, etc.) may be generated based on the ML analysis performed in block 1410.

At block 1420, the advanced sleep improvement recommendations generated in block 1415 are added to the application.

At block 1430, general sleep improvement recommendations may be generated by the application.

At block 1425, sleep training recommendations may be compiled for the user. The sleep training recommendations may represent a combination of the advanced sleep improvement recommendations and the general sleep improvement recommendations.

At block 1435, the user may review the sleep training recommendations through the application.

At block 1440, the user may update profile user data (e.g., name, demographic information, payment information, username and authentication credentials for a cloud account associated with the positional therapy device, etc.), which may be updated within the asynchronous storage database 1446.

At block 1445, via the application, the user may manually add and/or update sleep session influencers (e.g., information regarding the user's last meal, consumption of alcohol and/or caffeine, occurrences of night disturbances, recent exercise, how the user feels, etc.) within a sleep questionnaire for a prior sleep session, which may be updated within the asynchronous storage database 1446.

At block 1495, the user may watch sleep education videos and/or access other sleep education materials and/or resources via the application.

At block 1460, the cloud services may generate user sleep reports on a periodic basis and/or on demand at the request of the user. The user sleep reports may provide information regarding single session sleep patterns throughout the night, including, for example, sleep positions, breathing rate, heart rate, blood oxygen levels) and/or information regarding sleep hygiene, SA indicators (e.g., observed incidents of breathing cessation, etc.), and/or snoring frequency severity.

At block 1465, authorized medical staff, provided with access to the user's cloud account by the user, may download and review patient-shared sleep reports generated in block 1460.

At block 1470, the application may generate basic sleep reports on a periodic basis and/or on demand at the request of the user. The basic sleep reports may provide information regarding single or multiple session sleep patterns throughout the night, including, for example, sleep positions, breathing rate, heart rate, blood oxygen levels).

At block 1475, the user may download and/or review the sleep reports generated in block 1460 and/or 1470 via a web browser or via the application, respectively.

At block 1480, the application may generate reports for external medical applications (e.g., an EMR solution) in an appropriate format (e.g., CVS, OSCAR, or the like).

At block 1490, the cloud services may export reports (e.g., suitable for integration with external medical applications).

At block 1485, the user may download and/or review the reports generated in block 1480 and/or 1490 via a web browser or via the application, respectively, which can be forwarded to medical staff through other apps (e.g. email, text messaging) and/or uploaded to other medical apps on the users smartphone.

While in the context of the flow diagrams (e.g., FIGS. 8, and 11-14) described and illustrated herein a number of enumerated blocks are included, it is to be understood that examples may include additional blocks before, after, and/or in between the enumerated blocks. Similarly, in some examples, one or more of the enumerated blocks may be omitted and/or performed in a different order.

Example Time-Series Data Structure

FIG. 15 is a table 1500 illustrating various types of data that may be stored in an in-memory time-series data structure in accordance with an embodiment of the present disclosure. Table 1500 represents a non-limiting example, of various types of data that may be logged and represented in the form of time-series data (e.g., time-series data 511) for a given monitoring interval during a sleep session as described above, for example, with reference to FIGS. 5, 11, and 12. As described further below with reference to FIG. 16, the monitoring interval may be a configurable parameter (e.g., a standby delay time) that represents the amount of time a state machine task (e.g., state machine task 532) delays between monitoring cycles.

Table 1500 includes a data type column 1510, a name column 1520, and a description column 1530. The data type column 1510 indicates the type of value (e.g., integer, unsigned integer, floating point, etc.) the named data item may have and potentially the number of bits (e.g., 8, 16, 32, etc.) that are used to represent the named data item. The description column 1530 provides a brief description of the corresponding data item, for example, including units or the basis for computing the value of the data item. It is to be appreciated some of the data items (e.g., hardware flags, software flags, voltage and amperage values, processor temperature, etc.) may be used for internal purposes, for example, by the manufacturer or vendor of the positional therapy device.

In the present example, each entry of the time-series data includes: a 32-bit time stamp 1501 indicative of the time at which the associated data item values were captured; a state 1503 indicative of the current positional therapy device state, for example, one of the positional therapy device states described above with reference to FIG. 7; a state time 1503 indicative of how long the positional therapy device (e.g., positional therapy device 110 or 200) has been in the state; a current alert level 1504 indicative from which a volume and/or persistence of the alert required to cause the user (e.g., 101 or 1001) to change their sleeping position; an alert count 1505 indicative of the total number of alerts that have been triggered during the current sleep session; a motion count 1506 indicative of how many times motion has been detected by a positional sensor (e.g., positional sensor 220); a microphone count 1507 indicative of how many times sound has been detected by a microphone (e.g., microphone 215); X 1511 indicative of the X component of the current (last reported) absolute pointing vector of the positional therapy device (as indicated by a positional sensor (e.g., positional sensor 220)); Y 1512 indicative of the Y component of the current (last reported) absolute pointing vector of the positional therapy device; Z 1513 indicative of the Z component of the current (last reported) absolute pointing vector of the positional therapy device; tare X 1514 indicative of the X component of the current calibrated alert vector of the alert zone (e.g., alert zone 1030); tare Y 1515 indicative of the Y component of the current calibrated alert vector; tare Z 1516 indicative of the Z component of the current calibrated alert vector; heart rate 1521 indicative of beats per minute, for example, extrapolated or determined based on movement or sound captured over a predetermined amount of time by the positional sensor or the microphone; breathing rate 1522 indicative of breaths per minute, for example, extrapolated or determined based on movement or sound captured over a predetermined amount of time by the positional sensor or the microphone; oxygen saturation 1523 indicative of the current oxygen saturation reading, for example, from an external oximeter (e.g., pulse oximeter 121); and computed angles (zAngle 1524, zPitch 1525, and zRoll 1526) computed from X, Y, Z and tare X, tare Y, tare Z, vectors as described below. While for purposes of illustration a concrete example of the time-series data structure has been shown and described with reference to FIG. 15, it is to be appreciated, more or fewer data items may be captured in the time-series data structure and different data types may be used.

Example Configuration Parameters Data Structure

FIG. 16 is a table illustrating various types of data that may be stored in an in-memory configuration parameters data structure in accordance with an embodiment of the present disclosure. Table 1600 represents a non-limiting example of various types of positional therapy device configuration parameters that may be configured by the user (e.g., user 101 or 1001).

Table 1600 includes a data type column, a name column, and a description, a default value column, and a details column. The data type column indicates the type of value (e.g., integer, unsigned integer, floating point, etc.) the named parameter may have and potentially the number of bits (e.g., 8, 16, 32, etc.) that are used to represent the named parameter. The default value column identifies default values for respective named parameters. The description column provides a brief description of the corresponding parameter, for example, including units, a range of permissible values, data representation format, etc. It is to be appreciated some of the data items (e.g., version identifier (ID)) may be used by the manufacturer of vendor of the positional therapy device (e.g., positional therapy device 110 or 200), for example, for purposes of facilitating handling of changes to the configuration parameter data structure by software/firmware of the positional therapy device.

In the present example, the configuration parameters include: a disable TSD flag 1601 indicative of whether or not time-series data (e.g., time-series data 511) is to be logged; an alert holdoff count 1602 indicative of a delay before issuing an alert to the user for the first time, for example, responsive to determining the user's sleep position is within the alert zone (e.g., alert zone 1030) or responsive to the detecting snoring by the user; an alert squelch level 1603 indicative of an alert level at which no further alerts are to be issued to the user; an alert mode 1604 indicative of whether an arithmetic progression or a geometric progression is to be used for determining the volume of alerts; an alert start value 1605 indicative of a starting volume on which subsequent alerts of an alert set may build; a time zone offset 1606 indicative of the offset of the user's local time zone from coordinated universal time (UTC); acceleration tare X 1607 indicative of the X component of the alert zone angle/vector set by the user during calibration; acceleration tare Y 1608 indicative of the Y component of the alert zone angle/vector; acceleration tare Z 1609 indicative of the Z component of the alert zone angle/vector; an alert scale factor 1610 representing the slope (m) of the arithmetic progression or the scale factor (m) of the geometric progression, as the case may be; an alert growth factor 1611 representing the growth rate (r) of the geometric progression; an alert angle 1612 indicative of the width of the alert zone and whether the alert zone is to be inverted; an alert snooze time 1613 indicative of the amount of time the positional therapy device is to inhibit issuance of subsequent alerts responsive to receipt of a snooze command from a user before issuing subsequent alerts; an alert delay time 1614 indicative of the amount of time to pause between successive alerts of an alert set; a standby delay time 1615 indicative of the amount of time to delay between monitoring cycles performed by a state machine task (e.g., state machine task 532); an alert duration time 1616 indicative of the length of time to play an audible notification that is in the form of a tone; and an alert pattern 1617 indicative of whether a tone or a sampled sound (or collection of sampled sounds) is to be used as the alert and when a tone is to be used, the rhythm of the tone.

While for purposes of illustration a concrete example of a set of device configuration parameters has been shown and described with reference to FIG. 16, depending on the particular implementation, more or fewer parameters may be used and different data types may be used. While these parameters are generally not logged as part of the time-series data, some may be included within sleep reports and/or exports of logged data, for example, to provide context for a given report or export.

Example of Computing zAngle

Given that the dot product of two Euclidean vectors (gp and tp) is defined as the product of their magnitudes multiplied by the cosine of the angle between them, computing the zAngle can be done by computing the dot product of gp and tp, dividing by the product of their magnitudes, and taking the inverse cosine.

Assuming ONE_G is the magnitude of the positional sensor value when acceleration is equal to gravity (9.8 m/s/s), for purposes of completeness, below is a non-limiting example of how this might be done in code:

```
float tpx = (float) cfg.accelTareX / ONE_G;
float tpy = (float) cfg.accelTareY / ONE_G;
float tpz = (float) cfg.accelTareZ / ONE_G;
float tmag = sqrt(tpx*tpx + tpy*tpy + tpz*tpz);
float gpx = (float) tsd.X / ONE_G;
float gpy = (float) tsd.Y / ONE_G;
float gpz = (float) tsd.Z / ONE_G;
float gmag = sqrt(gpx*gpx + gpy*gpy + gpz*gpz);
// Compute the angle in degrees between the tare vector and the current
vector tsd.zAngle = acos( ( tpx*gpx + tpy*gpy + tpz*gpz ) /
(tmag*gmag) ) * 4068/71;
```

Example of Establishing a Rotational Frame of Reference

Translation of the measured vector by the positional sensor into the relative frame of reference established by the tare vector can be done using by any number of mathematical techniques including, but not limited to, using a rotational matrix, or unit quaternions, or the Angle-Axis method. For purposes of completeness, below is a non-limiting example of how this might be done in code using a precomputed rotational matrix:

```
// Rotate the current vector into the head reference frame
float ax = g_rMatrixA11 * gpx + g_rMatrixA21 * gpx +
g_rMatrixA31 * gpx;
float ay = g_rMatrixA12 * gpy + g_rMatrixA22 * gpy +
g_rMatrixA32 * gpy;
float az = g_rMatrixA13 * gpz + g_rMatrixA23 * gpz +
g_rMatrixA33 * gpz;
void computeRotationMatrix( ) {
  float Amag = sqrt(cfg.accelTareX * cfg.accelTareX +
  cfg.accelTareY
  cfg.accelTareY + cfg.accelTareZ * cfg.accelTareZ);
  float Ax = cfg.accelTareX / Amag;
  float Ay = cfg.accelTareY / Amag;
  float Az = cfg.accelTareZ / Amag;
  g_rMatrixA11 = (Ay * Ay − Ax * Ax * Az) / (Ax * Ax +
  Ay * Ay);
  g_rMatrixA12 = (−Ax * Ay − Ax * Ay * Az) / (Ax * Ax +
  Ay * Ay);
  g_rMatrixA13 = Ax;
  g_rMatrixA21 = g_rMatrixA12;
  g_rMatrixA22 = (Ax * Ax − Ay * Ay * Az) / (Ax * Ax +
  Ay * Ay);
  g_rMatrixA23 = Ay;
  g_rMatrixA31 = −Ax;
  g_rMatrixA32 = −Ay;
  g_rMatrixA33 = −Az;
}
```

Example Determination of Breathing Rate and Breathing Interruptions

Figure 17:
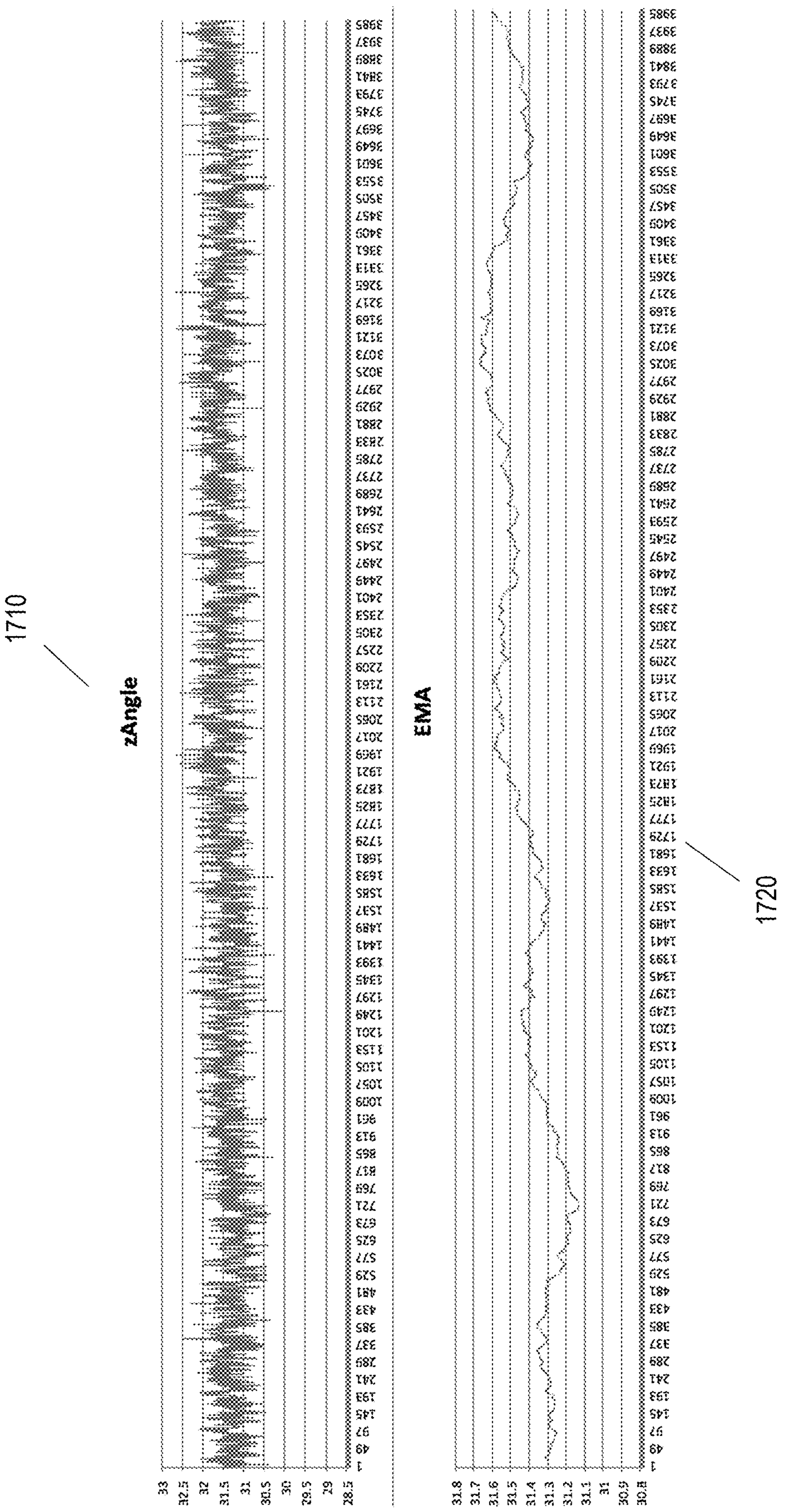
FIG. 17 depicts breathing captured via a positional sensor in the form of a first graph illustrating a zAngle computed at 25 Hz over the course of 20 seconds and a second graph illustrating the results after passing the zAngle data through an exponential moving average (EMA) low-pass filter in accordance with an embodiment of the present disclosure.

FIG. 17 depicts breathing captured via a positional sensor in the form of a first graph 1710 illustrating a zAngle computed at 200 Hertz (Hz) over the course of 20 seconds and a second graph 1720 illustrating the results after passing the zAngle data through an exponential moving average (EMA) low-pass filter in accordance with an embodiment of the present disclosure.

The gentle undulation of breathing can be seen in the raw waveform in the first graph 1710, which becomes further apparent after passing the data through the EMA low-pass filter. The EMA low-pass filter removes all of the high frequency noise. The regular ebb and flow of breathing can be clearly seen even if it is only a fraction of a degree.

According to one embodiment, EMA may be computed very efficiently using simple addition, subtraction and bit-shift, for example, in accordance with the following equation:

$$ema = (\text{current\_zAngle} >> 6) + (ema - (ema >> 6)) \qquad \text{EQ \#1}$$

Figure 18:
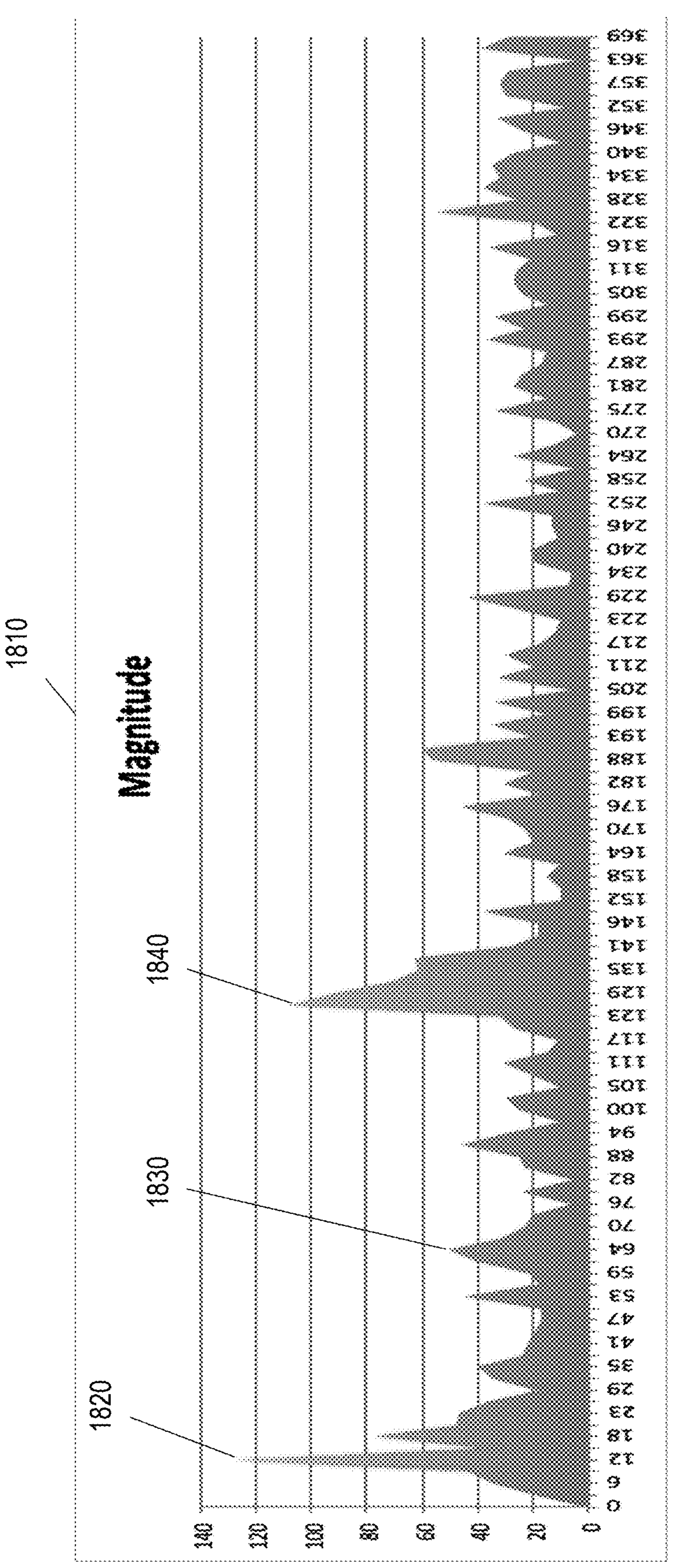
FIG. 18 is a graph illustrating the results of transforming the zAngle data of FIG. 17 into the frequency domain through a discrete Fast Fourier Transform (FFT) and discarding the zero order frequency in accordance with an embodiment of the present disclosure.

FIG. 18 is a graph 1810 illustrating the results of transforming the zAngle data of FIG. 17 into the frequency domain through a discrete Fast Fourier Transform (FFT) and discarding the zero order frequency (expressing DC offset or DC bias) in accordance with an embodiment of the present disclosure. In this example, the breathing rate is expressed as a peak magnitude in the first graph 1820 at 12 breaths per minute (BPM) in the frequency domain between 1 and 30 cycles per minute. According to one embodiment, breathing rate can be computed by using an FFT or by measuring the average peak-to-peak distance (wavelength) of the EMA and converting those measurements into the frequency of breaths per minute.

Figure 19:
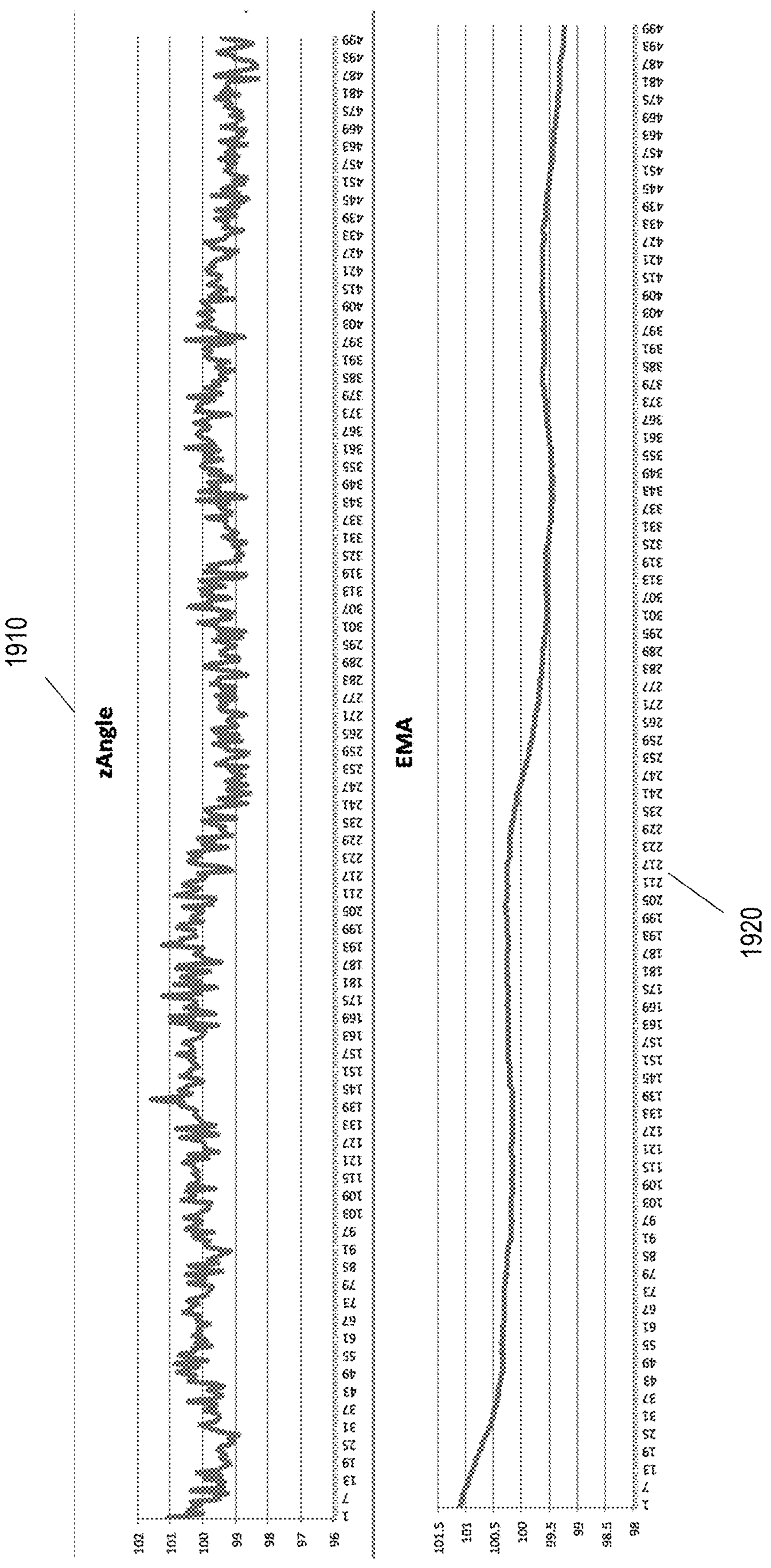
FIG. 19 depicts breathing captured via a positional sensor in the form of a first graph illustrating a zAngle computed at 25 Hz over the course of 20 seconds during which there is macro movement of the body of the user and a second graph illustrating the results after passing the zAngle data through an EMA low-pass filter in accordance in accordance with an embodiment of the present disclosure.

FIG. 19 depicts breathing captured via a positional sensor (e.g., positional sensor 220) in the form of a first graph 1910 illustrating a zAngle computed at 25 Hz over the course of 20 seconds during which there is macro movement of the body of the user (e.g., user 101 or 1001) and a second graph 1920 illustrating the results after passing the zAngle data through an EMA low-pass filter in accordance with an embodiment of the present disclosure.

As can be seen, with reference to graphs 1910 and 1920, the gentle undulation of breathing remains apparent even when there is macro movement of the body. This macro movement is expressed as a general trend, either rising or falling, of the data as a whole. However, this macro movement is completely filtered out when the data is transformed into the frequency domain through a discrete FFT and the zero order frequency (expressing DC offset) is discarded.

In one embodiment, breathing interruption (or an incident of breathing cessation) is characterized by consistent breathing followed by immediate absence of breathing without significant motion of the positional therapy device (indicating the positional therapy device has been removed from the ear), followed by consistent breathing again.

Figure 20:
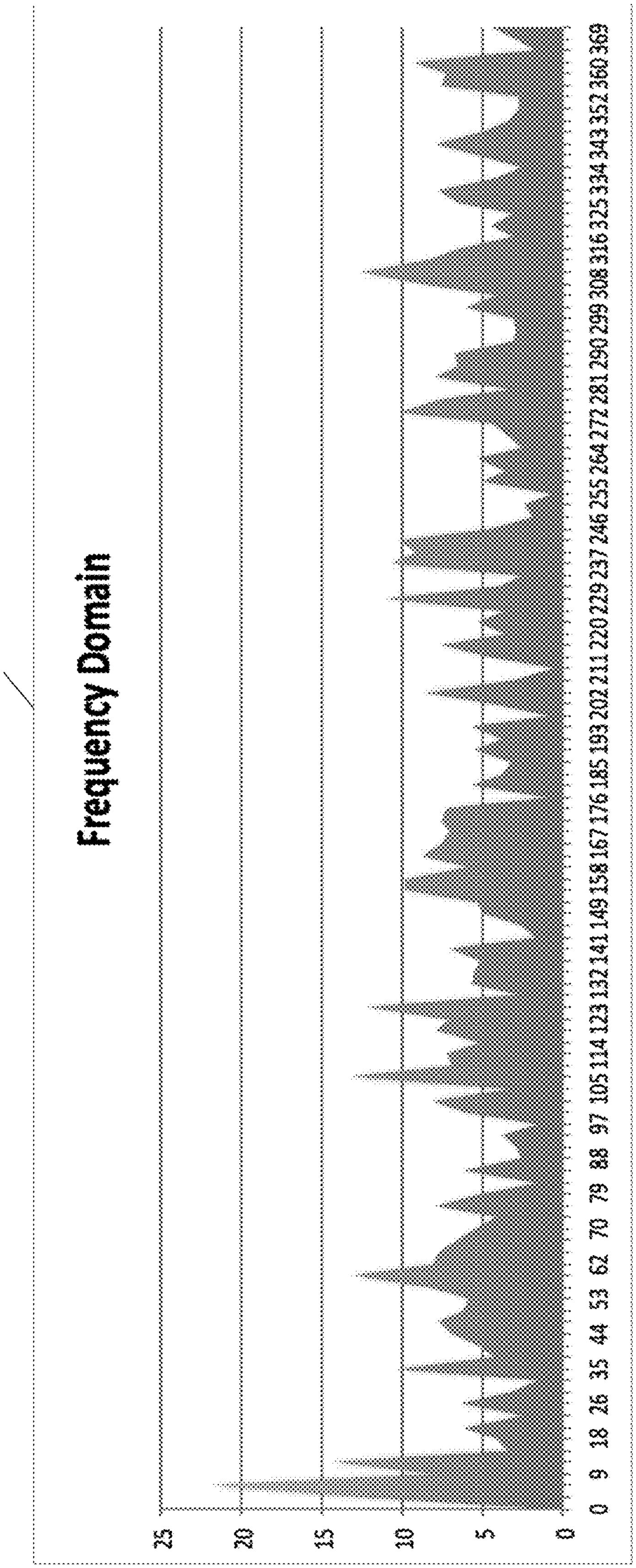
FIG. 20 is a graph illustrating the results of transforming the zAngle data of FIG. 19 into the frequency domain through a discrete FFT and discarding the zero order frequency in accordance with an embodiment of the present disclosure.

FIG. 20 is a graph illustrating the results of transforming the zAngle data of FIG. 19 into the frequency domain through a discrete FFT and discarding the zero order frequency in accordance with an embodiment of the present disclosure. As above, the breathing rate is expressed as a peak magnitude (at 6 BPM) in the frequency domain between 1 and 30 cycles per minute. Breathing rate can be computed by using an FFT or by measuring the average peak-to-peak distance (wavelength) of the EMA and converting those measurements into the frequency of breaths per minute. Alternatively, breathing rate can be determined using a microphone as described below with reference to FIG. 21.

Figure 21:
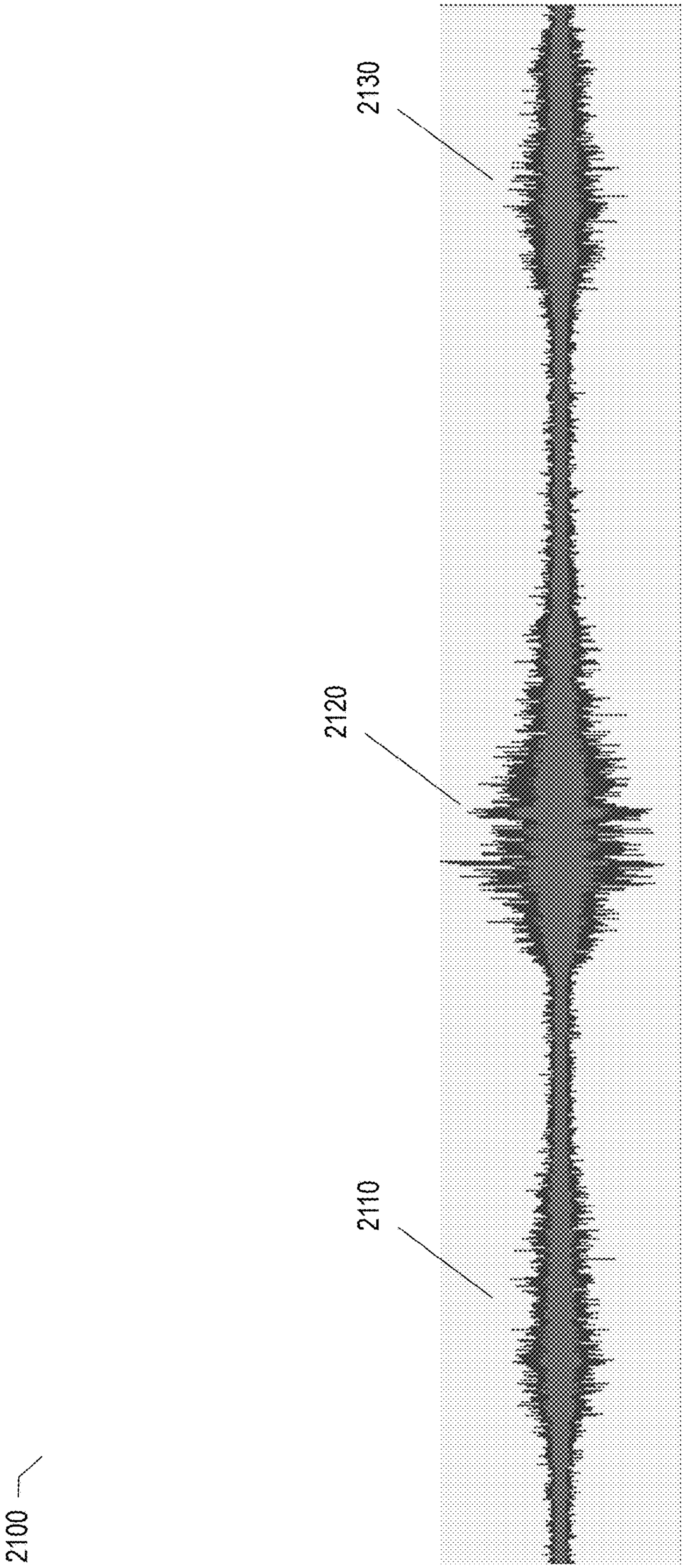
FIG. 21 depicts breathing captured using a microphone in accordance with an embodiment of the present disclosure.

FIG. 21 depicts a waveform 2100 representing breathing captured using a microphone (e.g., microphone 215) in accordance with an embodiment of the present disclosure. In one embodiment, sampled audio from the microphone is amplified. At this point, a noise reduction filter may be optionally applied. Although not required, a combination of a low-pass filter with 48 dB rolloff at 1000 Hz and a high-pass filter with 6 dB rolloff at 700 Hz can be applied to better isolate the breathing sound. Specific parameters for these filters can be adjusted as necessary to provide the best performance in regards to isolating the breathing. An alternating pattern of inhaling 2110 and 2130 and exhaling 2130 is revealed in the resulting waveform 2100. Measuring the root mean square (RMS) amplitude of this waveform 2100 and further passing that RMS through an EMA low-pass filter or decimation filter will result in a steady undulating waveform at 2× the breathing rate.

According to one embodiment, breathing rate can be computed by using an FFT or by measuring the average peak-to-peak distance (wavelength) of the EMA derived from the RMS amplitude and converting those measurements into the frequency of breaths per minute.

As those skilled in the art will appreciate, a user's heart rate may be determined with the use of heartbeats captured via a positional sensor (e.g., positional sensor 220) or heart sounds captured using a microphone (e.g., microphone 215) in a manner similar to that described above for breathing rate. According to one embodiment, heart rate can be computed by looking at the minor variations in the positional sensor. These variations appear as a pair of correlated high peaks at a frequency doubling. For example, in FIG. 18, there is a high magnitude peak 1840 at 129 beats per minute and a correlated peak 1830 at half of that frequency 64 beats per minute. In this case, the measured heart rate was between 63-65 bpm during this 20 second window.

Examples of Data that may be Captured to Facilitate Diagnosis

FIG. 22 is a table 2200 illustrating various types of sleep respiratory issues (e.g., conditions 2210), corresponding definitions 2220, and data captured 2230 for positional therapy device reporting and facilitation of diagnosis of a given sleep respiratory issue by a medical professional in accordance with an embodiment of the present disclosure.

Example PAP Mask System

Figure 23A:
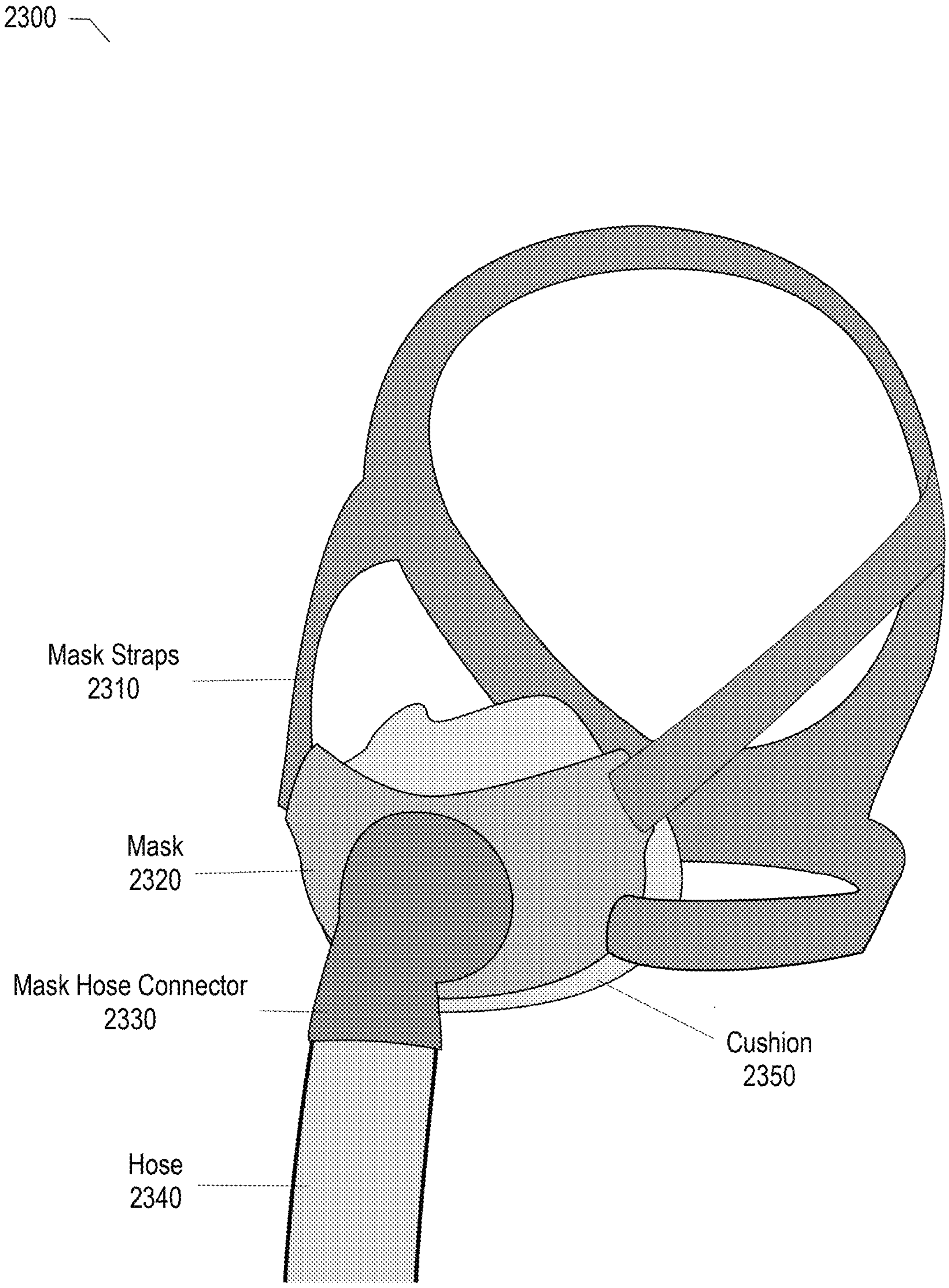
FIG. 23A depicts a PAP mask system.

FIG. 23A depicts a PAP mask system 2300 representative of a common full face PAP mask used for CPAP, BiPAP, and/or AutoPAP treatments. The PAP mask system 2300 includes: a hose 2340, a mask hose connector 2330, mask straps 2310, and a cushion 2350. The hose 2340 brings pressurized air from a PAP machine (not shown) to the PAP mask 2320 and user (not shown).

The mask hose connector 2330 affixes the hose 2340 to the mask 2320, which usually includes a swivel, a one way valve for letting pressure into the mask 2320 but not out through the hose, and a separate exhaust port for the user's exhaled air to escape.

Figure 23B:
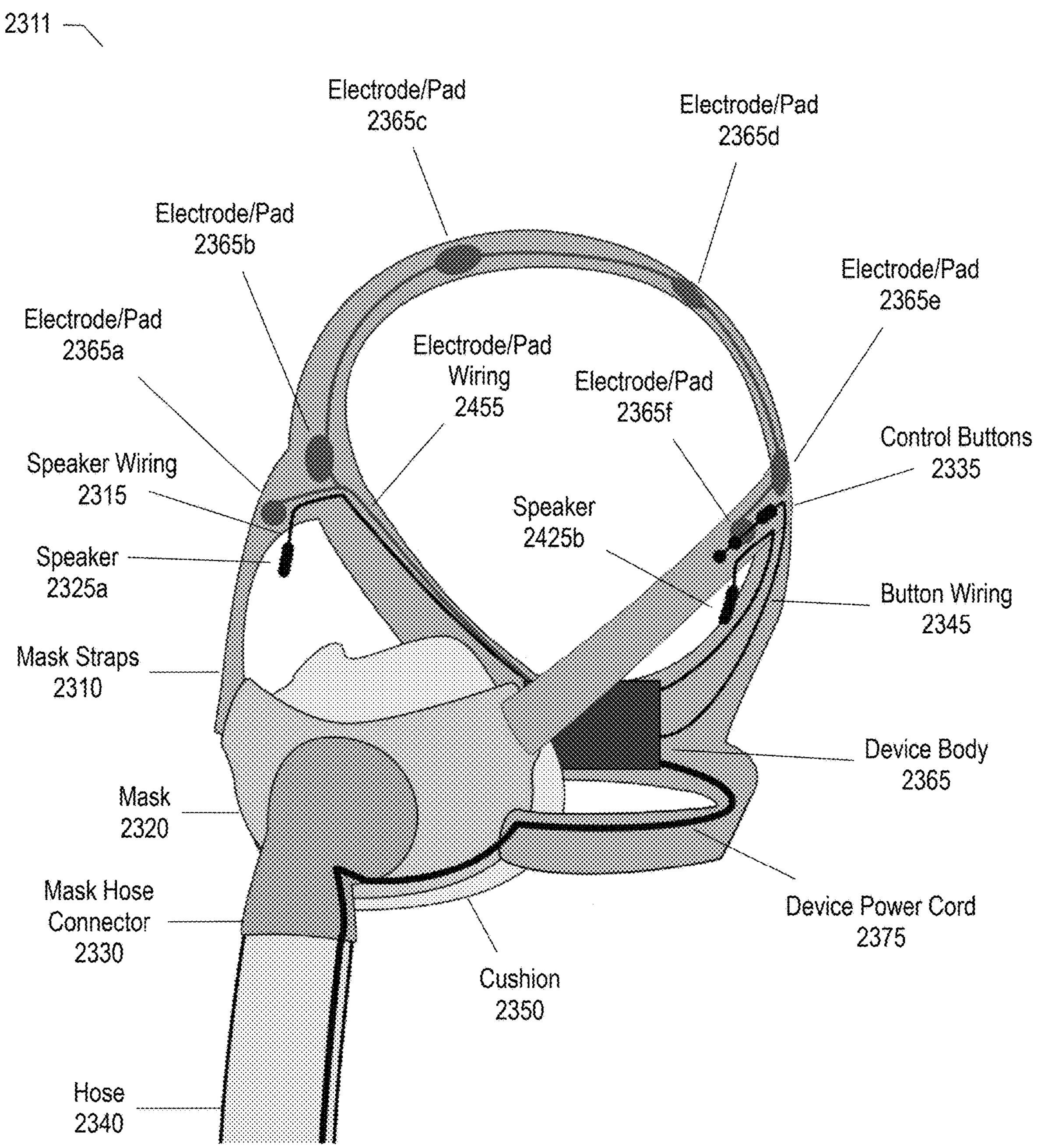
FIG. 23B depicts an X-Ray view of a PAP mask system with an integrated positional therapy device in accordance with an embodiment of the present disclosure.
Figure 23C:
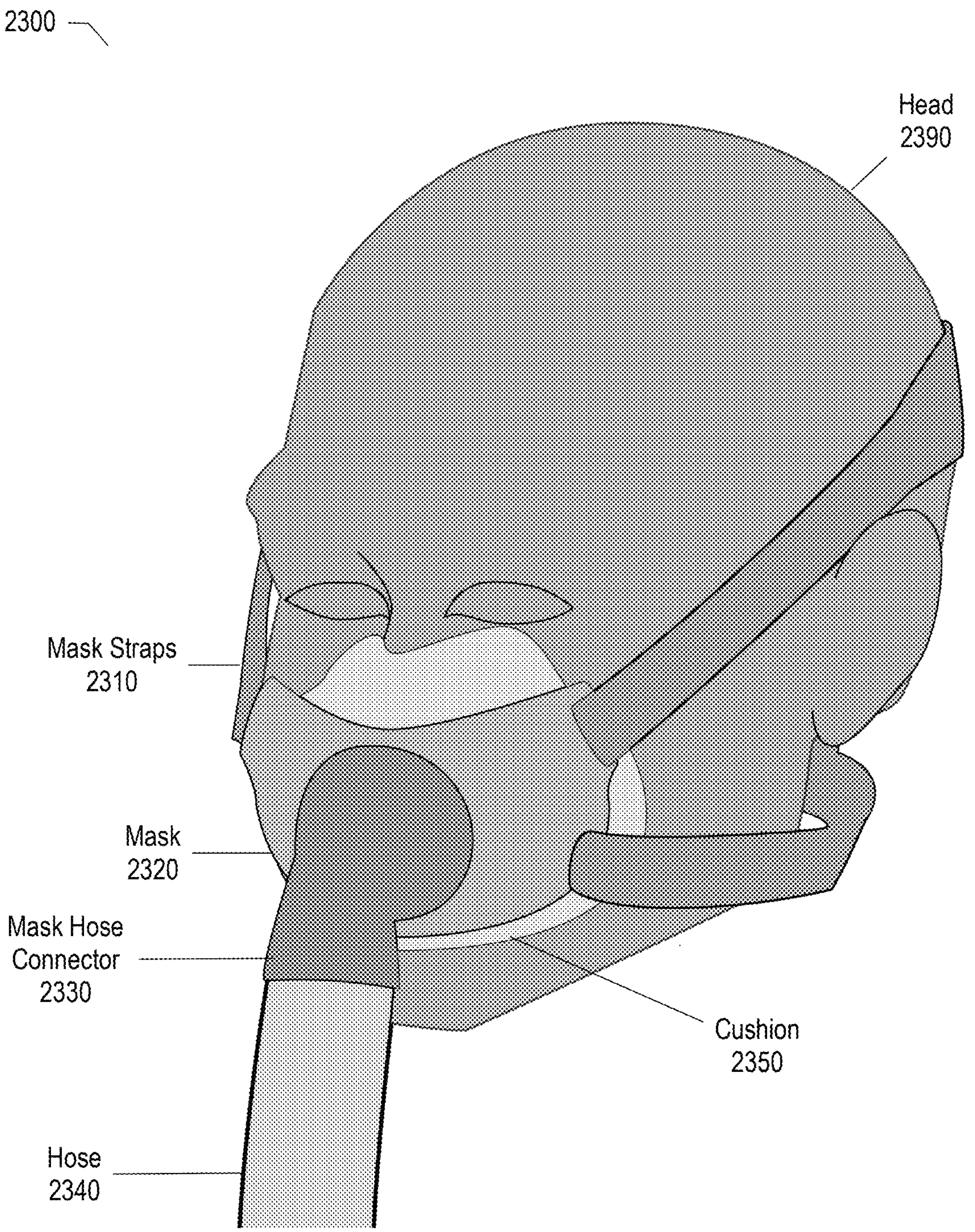
FIG. 23C depicts a PAP mask system worn by a user.

As shown in FIG. 23C, the mask straps 2310 (also referred to as a headgear strap) go over a user's head and are used to hold the PAP mask 2320 and additional components to the user's face. In one example, the mask straps 2310 may be made of high-quality sturdy, lightweight, breathable soft neoprene material.

The cushion 2350 acts as an air seal and soft barrier between the user's face and the mask 2320.

FIG. 23C depicts a PAP mask system 2300 worn by a user. This figure provides an example of how a PAP mask 2320 (in this case a full face mask) system is worn by a user over their nose and mouth with the mask straps 2310 engaging the user's head 2390.

Example PAP Mask System with Integrated Positional Therapy Device

FIG. 23B depicts an X-Ray view of a PAP mask system 2311 with an integrated positional therapy device (shown in black) in accordance with an embodiment of the present disclosure. FIG. 23B is drawn such that the components of the integrated positional therapy device can be seen through elements in the foreground, to demonstrate their positioning in relation to the PAP mask system (a.k.a. X-Ray view). In this example, the components of the integrated positional therapy device include a device body 2365 (which may include some or all of the architectural components described above with reference to FIG. 2), a device power cord 2375, one or more speakers (e.g., speaker 2325*a* and/or 2325*b*), speaker wiring 2315, one or more control buttons 2335, button wiring 2345, electrode/pad wiring 2355, and multiple pads or electrodes 2365*a-f*, a first subset (e.g., oval-shaped electrodes/pads 2365*b-e*) of which may be EEG electrodes/pads and a second subset (e.g., circular-shaped electrodes/pads 2365*a* and 2365*f*) of which may be electrooculography (EOG) electrodes/pads,.

According to various embodiments, the positional therapy device and its components (collectively, the positional therapy system) can be integrated with the PAP mask system 2311 by being directly sewn, affixed to, bound/strapped to, and/or molded into the PAP strap material or its components. For example, the PAP mask system 2311 can be integrated with the positional therapy system by merging them together permanently/semipermanently through sewing, gluing, melding, or other lasting approaches. The positional therapy system may alternatively be integrated in a less permanent approach to the PAP mask system 2311 with the intent of easily being affixed and removed. In the context of removable embodiments, the positional therapy components for the PAP mask system 2311 can be attached in various ways, non-limiting examples of which include the use of velcro straps (e.g., straps having hook and loop fasteners); ties; pockets, channels, and tunnels sewn into the straps; magnets; tubes; grippers; tracks; zippers; buttons; and/or snaps.

In the context of the present example, the positional therapy system is shown integrated with a full face mask (e.g., mask 2320), as an example. The positional therapy device may alternatively be integrated with a nasal mask, nasal pillow, hybrid mask, and/or other PAP mask styles through the like structures common across such PAP masks.

Like the other components of the positional therapy system, the device body 2365 can be external or embedded into the various parts of the PAP mask system 2311. For example, depending on the particular implementation, the device body 2365 may be integrated within the mask straps 2310 so as to be positioned approximately where the base of the skull meets the spinal column, elsewhere in the mask straps 2310 or integrated within the mask 2320 or cushion 2350. In one embodiment, the device body 2365 acts as the central unit of the positional therapy system. The device body 2365 may contain a rechargeable battery, CPU, and onboard memory. The device body 2365 may also include or be connected to the one or more speakers (e.g., speakers 2325*a-b*), the control buttons 2335, a positional sensor (not shown), a haptic motor (not shown), an ejectable memory card (not shown), a data port (not shown), a wireless transmitter (not shown), air pressure detection sensors, physical pressure sensors (e.g. strap or cushion pressure against the body), and a direct power supply (e.g., via the device power cord 2375).

The speakers can transmit positional alerts, cues, instructions, ambient sounds, music, podcasts, and other audio content. The source of the content can be from the device memory or streamed over wireless. In one embodiment, the speakers can be positioned directly over the ears, in front of the ears, behind the ears, or near the ears and pointed towards the ears. The positioning of the speakers may be adjustable by the user for better audio quality. They may be supported by a miniature positioning device that can be translated, extended, rotated, and locked into place. The speakers and/or their wires may be encapsulated in a tube/sheath (e.g., silicone) to help with flexibility, positioning, and positional rebounding back into the set position if bent from the pillow when sleeping. The speakers can be on or near one or both ears for stereo audio. An audio amplifier circuit can also be used to provide a more rich and high fidelity sound through the speakers.

In one embodiment, one or more microphones can be added to the device body 2365, speakers (e.g., speaker 2325*a-b*), or PAP mask system 2311 enabling the ability to deliver noise cancellation through the speakers. This will reduce the amount of external sounds that might otherwise disturb a user's sleep.

According to one embodiment, the control buttons 2335 may be provided to allow the user to adjust the positional therapy system functionality, including, but not limited to: adjusting volume; pausing/stopping alerts, cues, instructions, ambient sounds, music, podcasts, and other audio; activating and deactivating wireless connectivity; synching and data exchange with a mobile app (e.g., app 131 or mobile app 310), computer (e.g., computer system 150), or a medical/health device or medical/health application (e.g., an EMR solution). The control buttons 2335 may be located in a variety of locations on the PAP mask system 2311 or directly on the device body 2365. The control buttons 2335 may also provide tactile feedback when pressed.

A positional sensor (e.g., positional sensor 220-not shown) may be used to determine the position of the alert zone and to identify when the user (or more specifically, the user's head) has moved out of that position after a sleep session has started. Depending on the particular implementation, one or more of positional sensors or other positional recording units can be located on the PAP mask system 2311 or in the device body 2365.

In addition to audible notifications (e.g., provided via the speakers) or as an alternative to audible notifications, haptic notification may be used for alerts, cues, button feedback, massaging, and/or general feedback. In one embodiment, the preferred notification means (e.g., audible notifications, haptic notifications, or both) may be user configurable. One or more haptic motors may be located on the device body 2365 or elsewhere on the PAP mask system 2311. For example, a haptic motor may be activated (e.g., via control buttons 2335 or via an interface of the mobile app) as the preferred notification means for the positional therapy alerts described herein. Alternatively or additionally, a haptic motor may be used as an alert escalation, for example, when audio notification does not elicit the expected response from the user.

In one embodiment, a network of spaced out haptic motors across the PAP mask straps that vibrate in a constant state or in patterns may be used to massage the user's head.

In one embodiment, two or more electroencephalogram (EEG) electrodes (e.g., EEG pads 2365*a-e*) can be used to measure brain waves to determine which stages of sleep a user is in (e.g., wake, stage N1, stage N2, stage N3, and rapid eye movement (REM)). These electrodes may be embedded or attached to the mask straps such that they press against the head. In some examples, EEG data may be recorded or logged and may include EEG signals, voltage measurements, electrode channels, and electrical waveforms.

To further add clarity in identifying REM sleep, electrooculography (EOG) electrodes may be used to measure eye movement. These electrodes may be embedded or attached to the mask straps and press up against the sides of the skull near the eyes. Logs, reports, and raw data gathered from these electrodes can be passed to the app and connected systems for review and automated analysis for tuning the user's treatment and/or positional feedback.

In some examples, EEG and/or EOG electrodes or pads may be integrated with a PAP mask system with or without the inclusion of a positional therapy device. It is to be noted that the number and positioning of EEG and EOG electrodes or pads depicted in FIG. 23B is for illustrative purposes and either or both may change depending upon the goals and objectives of the particular implementation.

Depending on the particular implementation, power is provided to the positional therapy system through one or more of the following: a rechargeable battery (e.g., rechargeable battery 265), non-rechargeable battery, or the device power cord 2375 (e.g., a cord coming up the PAP mask system's hose 2340 as illustrated).

As described herein, the positional therapy device (e.g., positional therapy device 110 or 200) of a PAP mask integrated positional therapy system (e.g., representing a combination of a PAP mask system and the positional therapy device) may provide wireless engagement to devices and computers with the ability to transfer data and interact with apps and software applications. The wireless component can be built into the device or extended from the positional therapy device. For example, to achieve additional wireless range, an extended wireless antenna could be attached to the device and extended through the PAP mask system 2311.

To provide the best personal experience for each individual's sleep style and architecture, in one embodiment, a variety of engagement and disengagement timers can be applied to the alerts, cues, music, sounds, and haptics. Non-limiting examples of this may include one or more of the following:

- a timer that turns off the music or ambient sounds after a period of time following the device activation or the start of the music or ambient sounds, but leaves the positional therapy active.
- a timer that pauses positional therapy alert(s) and cue notification for a predefined or configurable amount of time (e.g., 30 minutes to read in the middle of the night or 3 minutes to go to the bathroom).
- a timer that starts or stops the positional therapy alerts at a particular time
- a timer that stops the haptic relaxation massage.
- a timer that stops playing one piece of content (e.g. a podcast) and transitions to playing a different piece of content or notification (e.g. ambient sounds such as falling rain).

Detection sensors (not shown) in/on the PAP mask system 2311 may be used to turn on/off or engage/disengage: the positional therapy, wireless capability, or app. This can come in the form of: checking if the PAP machine/device is turned on or pressure activated; if there is pressure in the mask, hose, or against the cushions; or pressure against the straps or cushion indicating the PAP mask system 2311 has been placed on the head.

Figure 23D:
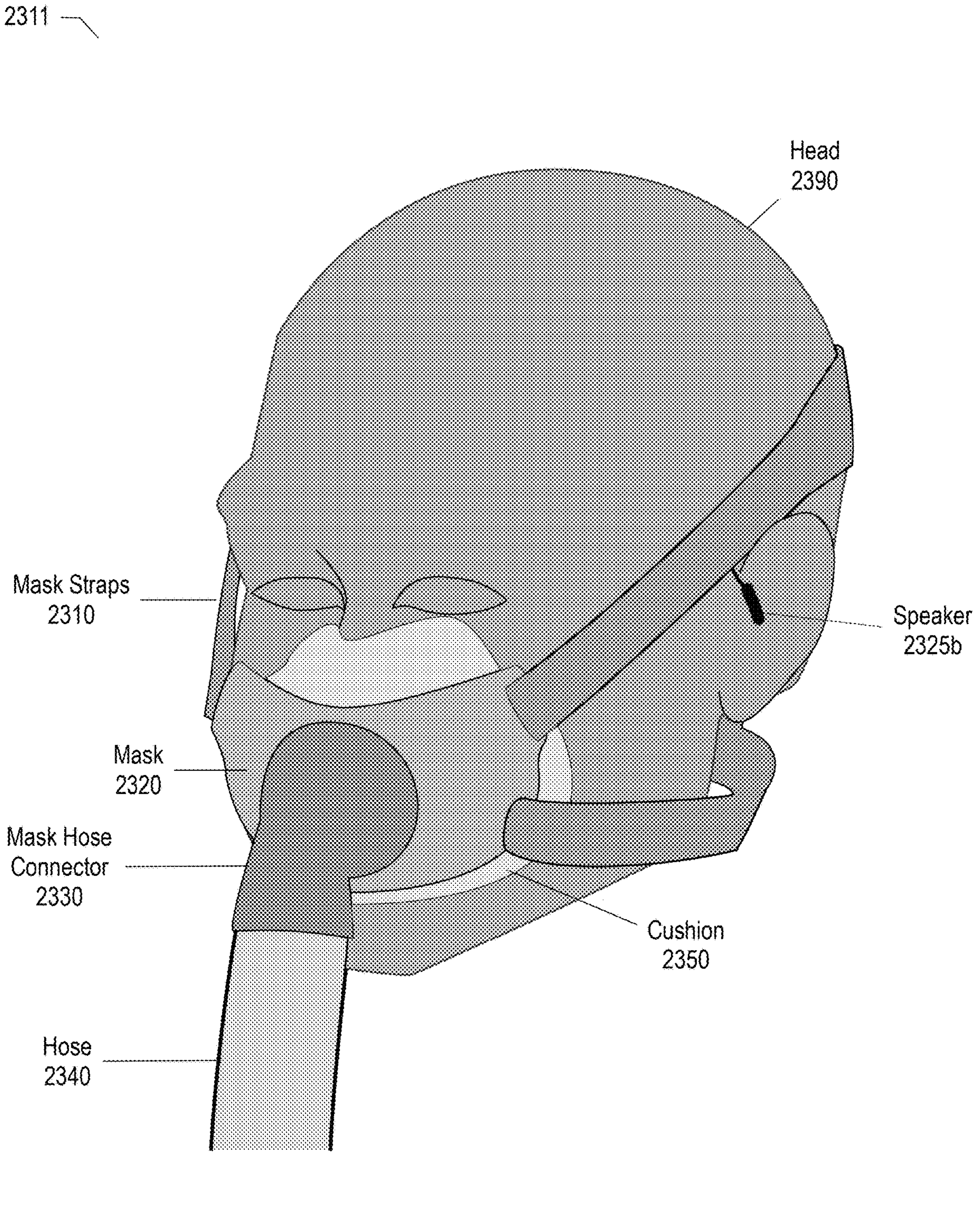
FIG. 23D depicts a PAP mask system with an integrated positional therapy device being worn by a user in accordance with an embodiment of the present disclosure.

As shown in FIG. 23D, the integrated positional therapy system may be mostly hidden from view when worn with only the one or more speakers 2325*a-b* and potentially some portion of the speaker wiring 2315 being externally visible from the PAP mask system 2311. In one embodiment, the control buttons 2335 may be exposed for better tactile recognition or hidden from view (e.g., under the mask strap material).

Due to less restrictions on size constraints of the positional therapy system in this particular configuration, for example, as compared to an ear device (the size of an ear bud), the device body 2365 might contain a removable SD card or other memory card to facilitate storage of additional audio, sound samples, and storage for time-series data. Also in this particular configuration, a larger battery may be provided to allow for the playing of audio for the entire duration of the sleep session or for a time specified by the user.

Embodiments of the present disclosure include various steps, which have been described above. The steps may be performed by hardware components or may be embodied in machine-executable instructions, which may be used to cause a processing resource (e.g., a general-purpose or special-purpose processor) programmed with the instructions to perform the steps. Alternatively, depending upon the particular implementation, various steps may be performed by a combination of hardware, software, firmware and/or by human operators.

Embodiments of the present disclosure may be provided as a computer program product, which may include a non-transitory machine-readable storage medium embodying thereon instructions, which may be used to program a computer (or other electronic devices, for example, a positional therapy device (e.g., positional therapy device 110, 200, or 2365) or a mobile device (e.g., smartphone 130) to perform a process. The machine-readable medium may include, but is not limited to, fixed (hard) drives, magnetic tape, floppy diskettes, optical disks, compact disc read-only memories (CD-ROMs), and magneto-optical disks, semiconductor memories, such as ROMs, PROMs, random access memories (RAMs), programmable read-only memories (PROMs), erasable PROMs (EPROMs), electrically erasable PROMs (EEPROMs), flash memory, magnetic or optical cards, or other type of media/machine-readable medium suitable for storing electronic instructions (e.g., computer programming code, such as software or firmware).

Various methods described herein may be practiced by combining one or more non-transitory machine-readable storage media containing the code according to embodiments of the present disclosure with appropriate special purpose or standard computer hardware to execute the code contained therein. A system for practicing various embodiments of the present disclosure may involve one or more computing systems (e.g., a positional therapy device, a mobile device, and/or a cloud platform) (or one or more processing resources within a single computing system) and storage systems containing or having network access to computer program(s) coded in accordance with various methods described herein, and the method steps associated with embodiments of the present disclosure may be accomplished by modules, routines, subroutines, or subparts of a computer program product.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions in any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

All examples and illustrative references are non-limiting and should not be used to limit the applicability of the proposed approach to specific implementations and examples described herein and their equivalents. For simplicity, reference numbers may be repeated between various examples. This repetition is for clarity only and does not dictate a relationship between the respective examples. Finally, in view of this disclosure, particular features described in relation to one aspect or example may be applied to other disclosed aspects or examples of the disclosure, even though not specifically shown in the drawings or described in the text.

The foregoing outlines features of several examples so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the examples introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A method comprising:

based on input by a user of a positive airway pressure (PAP) mask system, establishing a positional sleep therapy alert range with reference to a pointing vector of positional sensor of a positional therapy device by (i) calibrating the pointing vector for use as a relative frame of reference for subsequent determination of a head orientation of the user in a two-dimensional (2D) space or a three-dimensional (3D) space and (ii) calculating the positional sleep therapy alert range based on the calibrated pointing vector and an offset vector, wherein the positional therapy device is integrated with the PAP mask system;

during a sleep session of the user, wearing the PAP mask system, determining the head orientation of the user is within the positional sleep therapy alert range based on a state of the positional sensor; and after said determining, prompting the user to alter their sleep position.

2. The method of claim 1, further comprising logging a plurality of observations regarding a current head orientation of the user and whether the current head orientation is within or outside of the positional sleep therapy alert range.

3. The method of claim 2, further comprising additionally logging one or more of a breathing rate of the user, a heart rate of the user, a snoring state of the user, existence or non-existence of a breathing interruption, and an oxygen saturation of blood of the user by performing repeated measurements over time of the positional sensor and one or more other sensors associated with the positional therapy device.

4. The method of claim 1, wherein said determining involves reading the state of the positional sensor after detecting movement of the user.

5. The method of claim 3, further comprising repeating said prompting in accordance with an alert profile.

6. The method of claim 5, wherein the alert profile comprises a user-configurable alert profile and specifies one or more of: a volume of an audible notification, a rate of repetition of the audible notification with a set time duration in between, a time delay of a start of the audible notification, a number of repetitions of the audible notification, a pattern of the audible notification, a duration of the audible notification, and a type of sound associated with the audible notification.

7. The method of claim 5, further comprising:

observing a subsequent head orientation of the user is outside of the positional sleep therapy alert range; and after said observing, discontinuing said repeating.

8. The method of claim 1, wherein the offset vector is configurable by the user via an application associated with the positional therapy device.

9. The method of claim 1, wherein the state of the positional sensor comprises a current pointing vector of the positional sensor and wherein said determining includes:

determining the current pointing vector; and determining whether the current pointing vector is in a favorable or unfavorable orientation with respect to the calibrated pointing vector based on the positional sleep therapy alert range.

10. The method of claim 1, further comprising:

transmitting the state of the positional sensor from the positional therapy device to a smartphone or external processing device in communication with the positional therapy device via wireless communication; and wherein said determining is performed by an application running on the smartphone or the external processing device.

11. The method of claim 1, wherein said determining is performed on the positional therapy device.

12. The method of claim 1, wherein the positional sensor comprises one or more of an accelerometer, a gyroscope, an inertial measurement unit, and a magnetometer.

13. The method of claim 1, wherein the positional sleep therapy alert range represents:

one or more undesired orientations of a head of the user in the 2D space or the 3D space; or one or more desired orientations of the head of the user in the 2D space or the 3D space.

14. The method of claim 1, further comprising logging time-series data during the sleep session, wherein a given record of the time-series data for a particular time interval includes:

a timestamp;

information regarding the head orientation of the user determined during the particular time interval;

a breathing rate of the user;

an indication of whether a breathing interruption was detected during the particular time interval;

an indication of whether snoring by the user was detected during the particular time interval; and an indication of whether the head orientation of the user determined during the particular time interval was within or outside of the positional sleep therapy alert range.

15. The method of claim 14, further comprising exporting a report or raw data in a data interchange format or a medical format based on the time-series data.

16. The method of claim 14, further comprising presenting to the user via an application associated with the positional therapy device a summary of the sleep session based on the time-series data.

17. The method of claim 1, further comprising:

during the sleep session, detecting the user is snoring based on vibration detected by the positional sensor; and after said detecting, prompting the user to alter their sleep position.

18. A positional therapy device comprising:

a positional sensor including one or more of an accelerometer, a gyroscope, an inertial measurement unit, and a magnetometer;

a means for alerting a user of a positive airway pressure (PAP) mask system with which the positional therapy device is integrated;

one or more processors; and instructions that when executed by the one or more processors cause the positional therapy device to:

based on input by a user of the PAP mask system, establish a positional sleep therapy alert zone with reference to a pointing vector of the positional sensor by (i) calibrating the pointing vector for use as a relative frame of reference for subsequent determination of a head orientation of the user in a two-dimensional (2D) space or a three-dimensional (3D) space and (ii) calculating the positional sleep therapy alert zone based on the calibrated pointing vector and an offset vector;

during a sleep session in which the user is wearing the PAP mask system, determine the head orientation of the user is within the positional sleep therapy alert zone based on a state of the positional sensor; and after determining the sleep position of the user is within the positional sleep therapy alert zone, prompt the user to alter their sleep position by providing an alert to the user via the means for alerting.

19. The positional therapy device of claim 18, wherein the head orientation of the user is determined by reading the state of the positional sensor after detecting movement of the user.

20. The positional therapy device of claim 18, wherein the instructions further cause the positional therapy device to repeat the alert in accordance with an alert profile.

21. The positional therapy device of claim 20, wherein the alert profile comprises a user-configurable alert profile and specifies one or more of: a volume of an audible notification, a rate of repetition of the audible notification with a set time duration in between, a time delay of a start of the audible notification, a dynamically calculated and manually set number of repetitions of the audible notification, a pattern of the audible notification, a duration of the audible notification, and a type of sound associated with the audible notification.

22. The positional therapy device of claim 20, wherein the instructions further cause the positional therapy device to:

observe a subsequent sleep position of the user is outside of the positional sleep therapy alert zone; and after observing the subsequent sleep position of the user is outside of the positional sleep therapy alert zone, discontinue repetition of the alert.

23. The positional therapy device of claim 18, wherein the positional therapy device is integrated with straps of the PAP mask system permanently or semi-permanently.

24. The positional therapy device of claim 18, wherein the positional therapy device is integrated with a mask of the PAP mask system permanently or semi-permanently.

25. The positional therapy device of claim 18, wherein the instructions further cause the positional therapy device to log time-series data during the sleep session, wherein a given record of the time-series data for a particular time interval includes:

a timestamp;

information regarding a current head orientation of the user determined during the particular time interval;

a breathing rate of the user;

an indication of whether a breathing interruption was detected during the particular time interval;

an indication of whether snoring by the user was detected during the particular time interval; and an indication of whether the current head orientation of the user is within or outside of the positional sleep therapy alert zone.

26. The positional therapy device of claim 18, further comprising one or more of:

an oximeter;

a set of one or more Electroencephalograph (EEG) electrodes/pads; and a set of one or more Electrooculography (EOG) electrodes/pads.

27. The positional therapy device of claim 18, wherein the instructions further cause the positional therapy device to:

during the sleep session, determine the user is snoring based on vibrations detected by the positional sensor; and after determining the user is snoring, prompt the user to alter their sleep position by providing an alert to the user via the means for alerting.

28. The method of claim 14, wherein the given record of the time-series data for the particular time interval further includes:

information regarding Electroencephalograph (EEG) data including one or more of EEG signals, voltage measurements, electrode channels, and electrical waveforms; and information regarding Electrooculography (EOG) data including one or more of EOG signals, voltage measurements, electrode channels, and electrical waveforms.

29. The method of claim 1, wherein said prompting comprises providing an audible notification to the user, and wherein the audible notification proactively mitigates occurrences of sleep respiratory issues by the user.

30. The method of claim 29, wherein the audible notification comprises a sub-arousal audible notification performed during stage N1 or N2 of sleep.

31. The method of claim 6, further comprising analyzing time-series data collected for the sleep session and based thereon make a recommendation to the user to adjust one or more of the positional sleep therapy alert range, the volume of the audible notification, the rate of repetition of the audible notification, the number of repetitions of the audible notification, the duration of the audible notification, and the type of sound associated with the audible notification.

32. The method of claim 1, wherein the positional therapy device has integrated therein a wireless transmitter though which the positional therapy device communicates with a mobile application associated with the positional therapy device, and wherein the method further comprises, programmatically disabling the wireless transmitter prior to the sleep session.

33. The positional therapy device of claim 25, wherein the given record of the time-series data for the particular time interval further includes:

information regarding Electroencephalograph (EEG) data including one or more of EEG signals, voltage measurements, electrode channels, and electrical waveforms; and information regarding Electrooculography (EOG) data including one or more of EOG signals, voltage measurements, electrode channels, and electrical waveforms.

34. The positional therapy device of claim 18, wherein said providing an alert to the user comprises providing an audible notification to the user, and wherein the audible notification proactively mitigates occurrences of sleep respiratory issues by the user.

35. The positional therapy device of claim 34, wherein the audible notification comprises a sub-arousal audible notification performed during stage N1 or N2 of sleep.

36. The positional therapy device of claim 21, wherein the instructions further cause further cause the positional therapy device to analyze time-series data collected for the sleep session and based thereon make a recommendation to the user to adjust one or more of the positional sleep therapy alert zone, the volume of the audible notification, the rate of repetition of the audible notification, the number of repetitions of the audible notification, the duration of the audible notification, and the type of sound associated with the audible notification.

37. The positional therapy device of claim 18, further comprising a wireless transmitter though which the positional therapy device communicates with a mobile application associated with the positional therapy device, and wherein the instructions further cause the positional therapy device to programmatically disable the wireless transmitter prior to the sleep session.

* * * * *